(12) United States Patent
Sullenger et al.

(10) Patent No.: US 12,398,425 B2
(45) Date of Patent: Aug. 26, 2025

(54) ANTIDOTE-MEDIATED REVERSAL OF EXTRACELLULAR APTAMER STAINING

(71) Applicant: DUKE UNIVERSITY, Durham, NC (US)

(72) Inventors: Bruce Sullenger, Durham, NC (US); Bethany Gray, Durham, NC (US); Michael Nichols, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 0 days.

(21) Appl. No.: 18/128,949

(22) Filed: Mar. 30, 2023

(65) Prior Publication Data

US 2024/0141430 A1 May 2, 2024

Related U.S. Application Data

(62) Division of application No. 16/496,871, filed as application No. PCT/US2018/024075 on Mar. 23, 2018, now Pat. No. 11,634,772.

(60) Provisional application No. 62/475,315, filed on Mar. 23, 2017.

(51) Int. Cl.
    C12N 15/115    (2010.01)
    C12N 5/09      (2010.01)
    C12Q 1/6881    (2018.01)

(52) U.S. Cl.
    CPC ......... *C12Q 1/6881* (2013.01); *C12N 5/0693* (2013.01); *C12N 15/115* (2013.01); *C12N 2310/16* (2013.01); *C12N 2310/3517* (2013.01)

(58) Field of Classification Search
    None
    See application file for complete search history.

(56) References Cited

U.S. PATENT DOCUMENTS

| | | |
|---|---|---|
| 7,741,307 B2 | 6/2010 | Sullenger et al. |
| 7,776,836 B2 | 8/2010 | Sullenger et al. |
| 8,367,627 B2 | 2/2013 | Sullenger et al. |
| 8,790,924 B2 | 7/2014 | Sullenger et al. |
| 9,061,043 B2 | 6/2015 | Sullenger et al. |
| 9,687,529 B2 | 6/2017 | Sullenger et al. |
| 9,873,727 B2 | 1/2018 | Sullenger et al. |
| 9,958,448 B2 | 5/2018 | Halbert et al. |
| 10,144,926 B2 | 12/2018 | Levy |
| 10,350,158 B2 | 7/2019 | Lee et al. |
| 10,758,573 B2 | 9/2020 | Joly et al. |
| 2009/0130650 A1 | 5/2009 | Tan et al. |
| 2010/0076060 A1 | 3/2010 | Sullenger et al. |
| 2010/0184822 A1 | 7/2010 | Sullenger et al. |
| 2010/0249217 A1 | 9/2010 | Sullenger et al. |
| 2010/0267802 A1 | 10/2010 | Sullenger |
| 2011/0160443 A1 | 6/2011 | Sullenger et al. |
| 2012/0183564 A1 | 7/2012 | Sullenger |
| 2014/0296095 A1 | 10/2014 | Lin et al. |
| 2014/0342918 A1 | 11/2014 | Berezovski et al. |
| 2014/0348755 A1 | 11/2014 | Weng |
| 2015/0276750 A1 | 10/2015 | Zu |
| 2015/0307883 A1* | 10/2015 | Yarden ................. C12N 15/115 536/23.1 |
| 2017/0037544 A1 | 2/2017 | Sullenger |
| 2018/0117182 A1 | 5/2018 | Sullenger et al. |
| 2020/0095636 A1 | 3/2020 | Sullenger |

FOREIGN PATENT DOCUMENTS

| | | |
|---|---|---|
| JP | 2007-319153 | 12/2007 |
| WO | 2004/081021 | 9/2004 |
| WO | 2009/045545 | 4/2009 |
| WO | 2010/120518 | 10/2010 |
| WO | 2014/121256 | 8/2014 |
| WO | 2014/169049 | 10/2014 |
| WO | 2015/048173 | 4/2015 |
| WO | 2015/066027 | 5/2015 |
| WO | 2015/188839 | 12/2015 |
| WO | 2016/025804 | 2/2016 |
| WO | 2018/119422 | 6/2018 |

OTHER PUBLICATIONS

Allerson, C. R. et al. "Fully 2'-Modified Oligonucleotide Duplexes with Improved in Vitro Potency and Stability Compared to Unmodified Small Interfering RNA." J. Med. Chem 48 (2005): 901-904.

Becker et al., "Nucleic acid aptamers in therapeutic anticoagulation. Technology, development and clinical application," (2005) Thromb. Haemost. 93:1014-1020.

Bompiani et al., "A high affinity, antidote-controllable prothrombin and thrombin-binding RNA aptamer inhibits thrombin generation and thrombin activity," (2012) J Thromb Haemost 10:870-80.

Bonner, W. A., et al. "Fluorescence activated cell sorting." Review of Scientific Instruments 43.3 (1972): 404-409.

Burmeister, P. E., et al. "Direct in vitro selection of a 2'-O-methyl aptamer to VEGF." Chemistry & biology 12.1 (2005): 25-33.

Champlin, R. E. et al. T-cell depletion of bone marrow transplants for leukemia from donors other than HLA-identical siblings: advantage of T-cell antibodies with narrow specificities. Blood. 2000;95: 3996-4003.

Chan et al. "Phase 1b Randomized Study of Antidote-Controlled Modulation of Factor IXa Activity in Patients With Stable Coronary Artery Disease" (2008) Circulation 117:2865-2874.

(Continued)

*Primary Examiner* — Sean McGarry

(74) *Attorney, Agent, or Firm* — Quarles & Brady, LLP

(57) ABSTRACT

Provided herein are compositions and methods for sorting and/or identifying live cells. The compositions and methods provide for staining of live cells with aptamer so particular cells can be identified within or sorted from a heterogeneous population of live cells and subsequent reversal of the staining to prepare sorted and/or identified cells in their native state.

9 Claims, 28 Drawing Sheets

Specification includes a Sequence Listing.

(56) References Cited

OTHER PUBLICATIONS

Chan et al., "A randomized, repeat-dose, pharmacodynamic and safety study of an antidote-controlled factor IXa inhibitor," (2008) Journal of Thrombosis & Haemostasis 6:789-796.

Copelan, E. A. "Hematopoietic stem-cell transplantation." New England Journal of Medicine 354.17 (2006): 1813-1826.

Dyke et al., "First-in-human experience of an antidote-controlled anticoagulant using RNA aptamer technology: a phase 1a pharmacodynamic evaluation of a drug-antidote pair for the controlled regulation of factor IXa activity," (2006) Circulation 114:2490-2497.

Ellington et al., "In vitro selection of RNA molecules that bind specific ligands." (1990) Nature 346:818-22.

Extended European Search Report dated Oct. 22, 2020 for European Application No. 18770523.1 (11 pages).

Farokhzad, O.C. et al. "Nanoparticle aptamer bioconjugates: A new approach for targeting prostate cancer cells," (2004) Cancer Research 64:7668-7672.

Franciscis et al., "Nucleic Acid Aptamers for In Vivo Molecular Imaging," (2012) Molecular Imaging Chapter 5.

Guo, K-T. et al A New Technique for the Isolation and Surface Immobilization of Mesenchymal Stem Cells from Whole Bone Marrow Using High-Specific DNA Aptamers, Stem Cells 2006 24:220-2231.

Handgretinger, R. "Negative depletion of CD3+ and TcRaß+ T cells." Current opinion in hematology 19.6 (2012): 434-439.

Handgretinger, R., et al. "Isolation and transplantation of autologous peripheral CD34+ progenitor cells highly purified by magnetic-activated cell sorting." Bone marrow transplantation 21.10 (1998): 987-993.

Herdewijn P, "Heterocyclic modifications of oligonucleotides and antisense technology," (2000) Antisense Nucleic Acid Drug Development 10:297.

Herzenberg, L. A. et al. "The history and future of the fluorescence activated cell sorter and flow cytometry: a view from Stanford." Clinical chemistry 48.10 (2002): 1819-1827.

Heslop, H. E. et al. "Long-term restoration of immunity against Epstein-Barr virus infection by adoptive transfer of gene-modified virus-specific T lymphocytes." Nature medicine 2.5 (1996): 551-555.

Hoffman et al., "A Rapid Method to Isolate Platelets from Human Blood by Density Gradient Centrifugation," (1992) Am. J. Clin. Pathol. 98:531-533.

Holliger, P., et al. (2005). Engineered antibody fragments and the rise of single domains. Nature biotechnology, 23(9), 1126-1136.

Hwang, W. Y. K., et al. (2005). Immunogenicity of engineered antibodies. Methods, 36(1), 3-10.

International Searching Authority, International Search Report and Written Opinion for application PCT/US2018/024075. Mailed on Jun. 21, 2018.

James et al., "A molecular imaging primer: modalities, imaging agents, and applications," (2012) Physiol Rev 92(2):897-965.

Joachimi, A. et al., "A new anticoagulant-antidote pair: Control of thrombin activity by aptamers and porphyrins," (2007) Journal of the American Chemical Society 129(11):3036-3037.

June, C. H. "Adoptive T cell therapy for cancer in the clinic." The Journal of clinical investigation 117.6 (2007): 1466-1476.

Kandimalla, E.R. et al. "Design, biochemical, biophysical and biological properties of cooperative antisense oligonucleotides." Nucleic Acids Res. Sep. 11, 1995; 23(17): 3578-3584.

Kaufman, E. N., et al. (1992). Effect of bivalent interaction upon apparent antibody affinity: experimental confirmation of theory using fluorescence photobleaching and implications for antibody binding assays. Cancer research, 52(15), 4157-4167.

Labib, M. et al., "Aptamer and Antisense-Mediated Two-Dimensional Isolation of Specific Cancer Cell Subpopulations," J.Am. Chem. Soc. 2016; 138:2476-2479.

Li, N., et al. "Inhibition of cell proliferation by an anti-EGFR aptamer." PloS one 6.6 (2011): e20299.

Locatelli, F., et al. "Negative depletion of a/ß+ T cells and of CD19+ B lymphocytes: a novel frontier to optimize the effect of innate immunity in HLA-mismatched hematopoietic stem cell transplantation." Immunology letters 155.1-2 (2013): 21-23.

Mackensen, A., et al. "Phase I study of adoptive T-cell therapy using antigen-specific CD8+ T cells for the treatment of patients with metastatic melanoma." Journal of Clinical Oncology 24.31 (2006): 5060-5069.

Maier, K. E., et al. (2016). A new transferrin receptor aptamer inhibits new world hemorrhagic fever mammarenavirus entry. Molecular Therapy-Nucleic Acids, 5, e321.

Masui, H., et al. (1993). Consumption of EGF by A431 cells: evidence for receptor recycling. The Journal of cell biology, 120(1), 85-93.

Mattanovich, D. et al. "Applications of cell sorting in biotechnology." Microbial cell factories 5.1 (2006): 1-11.

Nimjee et al., "A novel antidote-controlled anticoagulant reduces thrombin generation and inflammation and improves cardiac function in cardiopulmonary bypass surgery," (2006) Mol. Ther. 14:408-45.

Nimjee et al., "Aptamers as Therapeutics," (2017) Annual review of pharmacology and toxicology 57:61-79.

Nimjee, S.M. et al. "Aptamers: an emerging class of therapeutics," (2005) Annual review of medicine 56:555-83.

Nimjee et al., "Rapidly regulating platelet activity in vivo with an antidote controlled platelet inhibitor," (2012) Molecular therapy : the journal of the American Society of Gene Therapy 20:391-7.

Office Action for U.S. Appl. No. 16/496,871 mailed Nov. 5, 2021.

Oney, et al., "Antidote-controlled platelet inhibition targeting von Willebrand factor with aptamers," (2007) Oligonucleotides 17(3):265-274—Abstract.

Oney, S. et al., "Development of universal antidotes to control aptamer activity," (2009) Nature Medicine, 15(10):1224-1229.

Padilla, R. et al. "A Y639F/H784A T7 RNA polymerase double mutant displays superior properties for synthesizing RNAs with non-canonical NTPs." Nucleic acids research 30.24 (2002): e138-e138.

Padilla, R. et al. "Efficient synthesis of nucleic acids heavily modified with non-canonical ribose 2'-groups using a mutant T7 RNA polymerase (RNAP)." Nucleic acids research 27.6 (1999): 1561-1563.

Ray, P. et al. "Aptamer-mediated delivery of chemotherapy to pancreatic cancer cells." Nucleic acid therapeutics 22.5 (2012): 295-305.

Riddell, S. R. et al. "Principles for adoptive T cell therapy of human viral diseases." Annual review of immunology 13.1 (1995): 545-586.

Rusconi, C.P. et al., "Antidote-mediated control of an anticoagulant aptamer in vivo," (2004) Nature Biotechnology 22(11):1423-1428.

Rusconi, C.P. et al., "RNA aptamers as reversible antagonists of coagulation factor IXa," (2002) Nature 419(5):90-94.

Sako, Y. et al. "Single-molecule imaging of EGFR signalling on the surface of living cells." Nature cell biology 2.3 (2000): 168-172.

Schlessinger, J. "Autoinhibition control." Science 300.5620 (2003): 750-752.

Schlessinger, J. "Common and distinct elements in cellular signaling via EGF and FGF receptors." Science 306.5701 (2004): 1506-1507.

Schmidt-Ullrich, R. K., et al. "Radiation-induced proliferation of the human A431 squamous carcinoma cells is dependent on EGFR tyrosine phosphorylation." Oncogene 15.10 (1997): 1191-1197.

Soutschek, J., et al. "Therapeutic silencing of an endogenous gene by systemic administration of modified siRNAs." Nature 432.7014 (2004): 173-178.

Steen-Burrell et al., "Development of an Antidote-Controlled RNA Probe for Molecular Thrombi Imaging," Abstract submitted to Arteriosclerosis, Thrombosis and Vascular Biology (ATVB) Meeting. May 2015.

Sykes, M. et al. "Treatment of severe autoimmune disease by stem-cell transplantation." Nature 435.7042 (2005): 620-627.

Tuerk et al., "Systematic evolution of ligands by exponential enrichment: RNA ligands to bacteriophage T4 DNA polymerase," (1990) Science 249:505-10.

(56) References Cited

OTHER PUBLICATIONS

White, R. et al., "Generation of Species Cross-reactive Aptamers Using Toggle SELEX," (2001) Molecular Therapy 4(6):567-573.
Wong et al., "A double-filter method for nitrocellulose-filter binding: application to protein-nucleic acid interactions," (1993) Proc Natl Acad Sci USA 90(12): 5428-5432.
Drolet et al., "An enzyme-linked oligonucleotide assay," (1996) Nat. Biotechnol. 14:1021-1025.
Fahmy et al, "Surface modification of biodegradable polyesters with fatty acid conjugates for improved drug targeting," Biomaterials, 2005, 26, 5727-5736.

\* cited by examiner

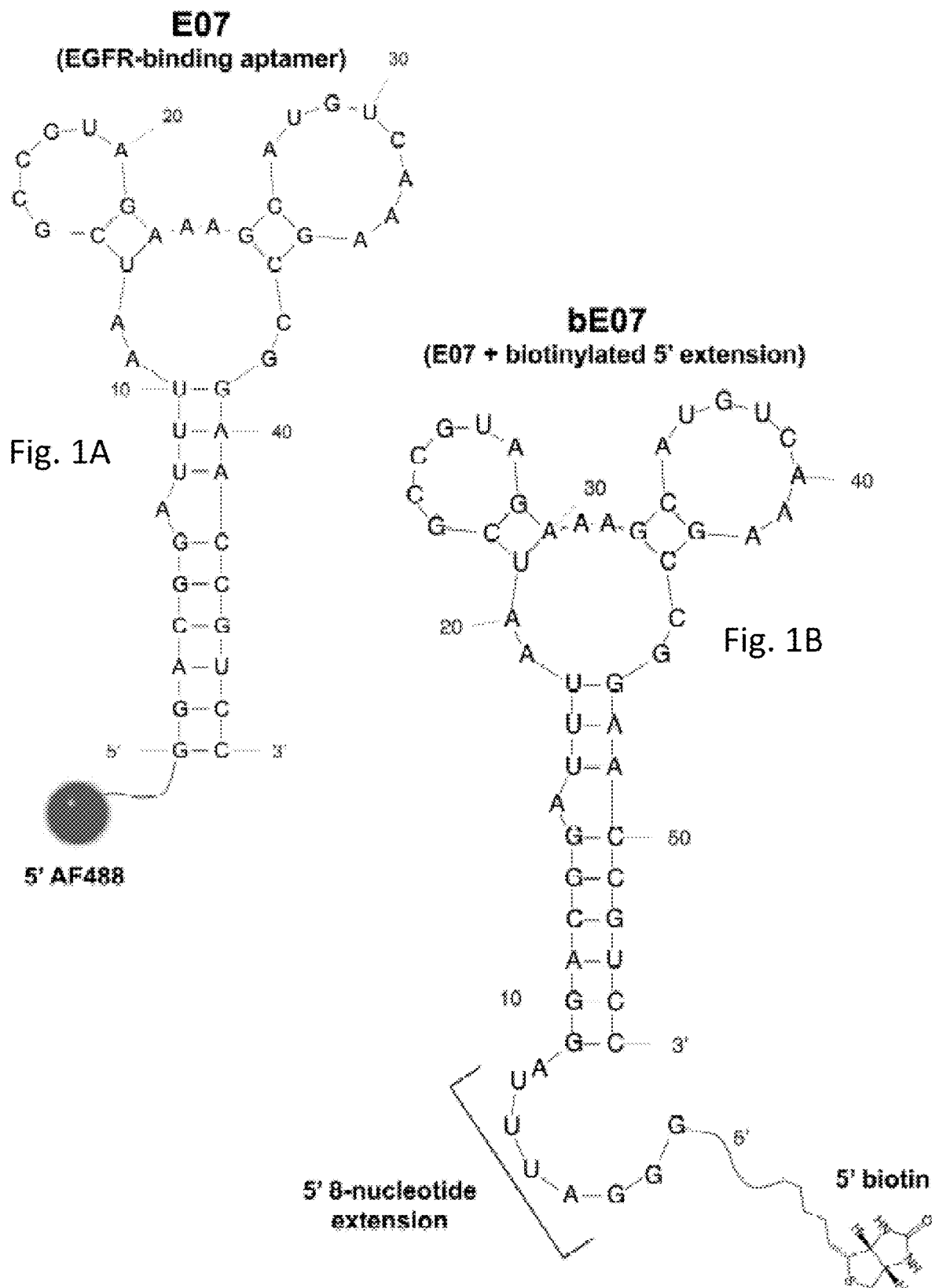

ANTIDOTE-MEDIATED REVERSAL OF EXTRACELLULAR APTAMER STAINING

CROSS-REFERENCE TO RELATED APPLICATIONS

This patent application is a divisional of U.S. patent application Ser. No. 16/496,871, filed Sep. 23, 2019, which is a national stage filing under 35 U.S.C. 371 of International Application No. PCT/US2018/024075, filed Mar. 23, 2018, which claims the benefit of and priority to U.S. Provisional Patent Application No. 62/475,315, filed Mar. 23, 2017, each of which are incorporated herein by reference in their entirety.

STATEMENT OF GOVERNMENT SUPPORT

This invention was made with government support under R21EB017868 awarded by the National Institutes of Health. The government has certain rights in the invention.

REFERENCE TO A SEQUENCE LISTING

This application is being filed electronically via Patent Center and includes an electronically submitted Sequence Listing in .xml format. The .xml file contains a sequence listing entitled "155554.00689.xml" created on May 30, 2023 and is 36,434 bytes in size. The Sequence Listing contained in this .xml file is part of the specification and is hereby incorporated by reference herein in its entirety.

FIELD OF INVENTION

The technology is generally related to compositions and methods for cell identification and/or sorting. More specifically, the technology is related use of aptamers and antidotes for positive cell identification and/or sorting of cells.

BACKGROUND

Selective purification of cells is routinely performed and critical for numerous clinical and basic research applications. Clinically, CD34+ cell enrichment is required for the 45,000+ hematopoietic stem cell transplantations performed annually and CD8+ cell purification required for the rapidly growing field of adoptive T-cell therapy. Popular basic research purification schemes such as fluorescence-activated cell sorting (FACS) and magnetic-activated cell sorting (MACS) traditionally rely on antibodies for selective labeling and subsequent isolation of target cell populations. However, antibody labeling is irreversible, reducing the utility of isolated cells in downstream applications. The inherent immunogenicity of antibodies strongly contraindicates their use in purification of cellular therapeutics, and antibodies that bind antagonistically to receptors disrupt native signaling pathways, potentially compromising the usefulness of isolated cells. Strategies to circumvent these well-recognized issues include negative depletion, in which undesired cells are labeled and discarded, and the use of antibodies engineered to lack the immunogenic Fc region. However, neither of these approaches guarantees a pure population of functionally uninhibited cells for basic research or clinical use.

BRIEF SUMMARY OF THE INVENTION

Provided herein are compositions and methods for sorting and/or identifying live cells. The compositions and methods provide for staining of live cells with aptamer so particular cells can be identified within or sorted from a heterogeneous population of live cells and subsequent reversal of the staining to prepare sorted and/or identified cells in their native state.

Methods for live cell identification comprise providing a heterogeneous population of live cells, the heterogeneous population of live cells comprising a cell having a surface-bound molecular target, contacting the surface-bound molecular target with a sorting aptamer having a binding affinity for the molecular target, the sorting aptamer comprising an oligonucleotide and a sorting label, identifying the cell having the surface-bound molecular target amongst the heterogeneous population of cells using the sorting label, and removing the sorting aptamer from the surface-bound molecular target to prepare a sorted cell in its native state. The method may further comprise sorting the cell having the surface-bound molecular target from at least a portion the heterogeneous population of cells using the sorting label.

Methods for live cell sorting comprise providing a heterogeneous population of live cells, the heterogeneous population of live cells comprising a cell having a surface-bound molecular target, contacting the surface-bound molecular target with a sorting aptamer having a binding affinity for the molecular target, the sorting aptamer comprising an oligonucleotide and a sorting label, sorting the cell having the surface-bound molecular target amongst the heterogeneous population of cells using the sorting label, and removing the sorting aptamer from the surface-bound molecular target to prepare a sorted cell in its native state. The method may further comprise identifying the cell having the surface-bound molecular target from at least a portion the heterogeneous population of cells using the sorting label.

In either of the methods described above, removing the sorting aptamer from the surface-bound molecular target may comprise contacting the sorting aptamer with an oligonucleotide antidote, the oligonucleotide antidote comprising a sequence at least partially complementary to a portion of the sorting aptamer. In some embodiments, the aptamer is a multivalent aptamer comprising a multiplicity of binding motifs. The binding motifs may be the same or different. In some embodiments, the aptamer is an aptamer conjugate. The removing step may also be accomplished by modulating the temperature and/or the concentration of a divalent ion alone or in combination with contacting the sorting aptamer with an oligonucleotide antidote.

The sorting label may comprise a reporter label, a magnetic label, a binding label, or any combination thereof. In some embodiment, the reporter label comprises a fluorophore moiety. In another embodiment, the magnetic label comprises a magnetic bead. In yet another embodiment, the binding label is selected from the group consisting of biotin, avidin, streptavidin, and digoxigenin.

Sorting or identification of the cells may be accomplished by any method suitable for live cells. Examples of sorting techniques for live cells include fluorescence-activated cell sorting and magnetic-activated cell sorting.

The methods described above may further comprise removing exogenous material. The exogenous material may comprise the staining aptamer, the antidote, and/or any other foreign material.

Aptamer conjugates are also provided herein. The aptamer conjugate may comprise a sorting aptamer comprising a binding label complexed to a linker, the linker comprising a reporter label and/or a magnetic label. In some embodiments, the binding label comprises biotin and the linker comprises streptavidin. The aptamer conjugate may comprise multiplicity of sorting aptamers each comprising a binding label. In particular embodiments, the aptamer conjugate comprises two sorting aptamers each comprising a binding label complexed to the linker.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

FIGS. 1A and 1B illustrate aptamer secondary structure with differing end modification: E07 5'-labeled with AlexaFluor 488 (SEQ ID NO: 1; FIG. 1A) and bE07 5'-labeled with an oligonucleotide extension and biotin (SEQ ID NO: 5; FIG. 1B).

FIG. 3B shows fluorescence counts at the 2 min. time-point at 37° C., FIG. 3C shows fluorescence counts at the 10 min. time point at 37° C., and FIG. 3D shows the time-course comparison. Label colors for FIGS. 3B-3C: Cells only (grey), E07→no antidote (green), E07→25 µM sA9 (orange), E07→25 µM A9 (purple), and E07→25 µM mA9 (red). Label colors for FIG. 3D: E07→no antidote (green), Control aptamer (C36) (grey), E07→SA9 (orange), E07→A9 (purple), and E07→mA9 (red).

FIG. 3E shows the fluorescence counts when A9 is provided at difference concentrations, FIG. 3F shows fluorescence counts when mA9 is provided at difference concentrations, and FIG. 3G shows the a relative comparison of A9 and mA9 at different concentrations. Label colors for FIGS. 3E-3F: Cells only (grey), E07→no antidote (red), E07→50 nM antidote (pink), E07→125 nM antidote (purple), E07→250 nM antidote (teal), E07→500 nM antidote (magenta), E07→1 µM antidote (orange), E07→1 µM antidote (light green), and E07→1 µM antidote (dark green).

FIGS. 4B-5D show cell viability was maintained after sorting with E07-SA and destaining with antidote mA9. Live/dead assays indicated that viability was not affected by sorting or cell-label reversal. FIG. 4B shows unstained, sorted cells that were untreated or heat-treated (65° C. for 15 min), respectively, and served as live and dead controls.

FIG. 4E shows AF488 (top) and AF647 (bottom) fluorescence for untreated cells (grey) and E07-SA-AF488 treated cells (blue). FIG. 4F shows AF488 (top) and AF647 (bottom) fluorescence for untreated cells (grey), E07-SA-AF488 treated cells (purple), and E07-SA-AF488+mA9 treated cells (orange). FIG. 4G shows AF488 (top) and AF647 (bottom) fluorescence for untreated cells (grey), E07-SA-AF488+E07-SA-AF647 treated cells (magenta), and E07-SA-AF488+mA9+E07-SA-AF647 treated cells (green).

FIG. 4H shows FITC (top) and AF647 (bottom) fluorescence for untreated cells (grey) and FITC EGFR Ab treated cells (blue). FIG. 4I shows FITC (top) and AF647 (bottom) fluorescence for untreated cells (grey), FITC EGFR Ab treated cells (purple), and FITC EGRF Ab+mA9 treated cells (orange). FIG. 4J shows FITC (top) and AF647 (bottom) fluorescence for untreated cells (grey), FITC EGRF Ab+AF647 2° Ab treated cells (magenta), and FITC EGRF Ab+mA9+AF647 2° Ab treated cells (green).

FIGS. 7C (bE07) and 7D (bC36) show the intensities of bands corresponding to each conjugate size quantified with software and then normalized to the combined intensity of all conjugates for that sample.

FIG. 10B) vs. (500 nM; FIG. 10C) effectively removed the bound conjugate mixture over 30 min. Label colors for FIGS. 10B-10C: E07, media (light blue), E07, 500 nM mA9 or E07, 5 µM mA9 (dark blue), E07-SA media (light green), and E07-SA, 500 nM mA9 or E07-SA, 5 µM mA9 (dark green).

DETAILED DESCRIPTION OF THE INVENTION

Figure 1C:
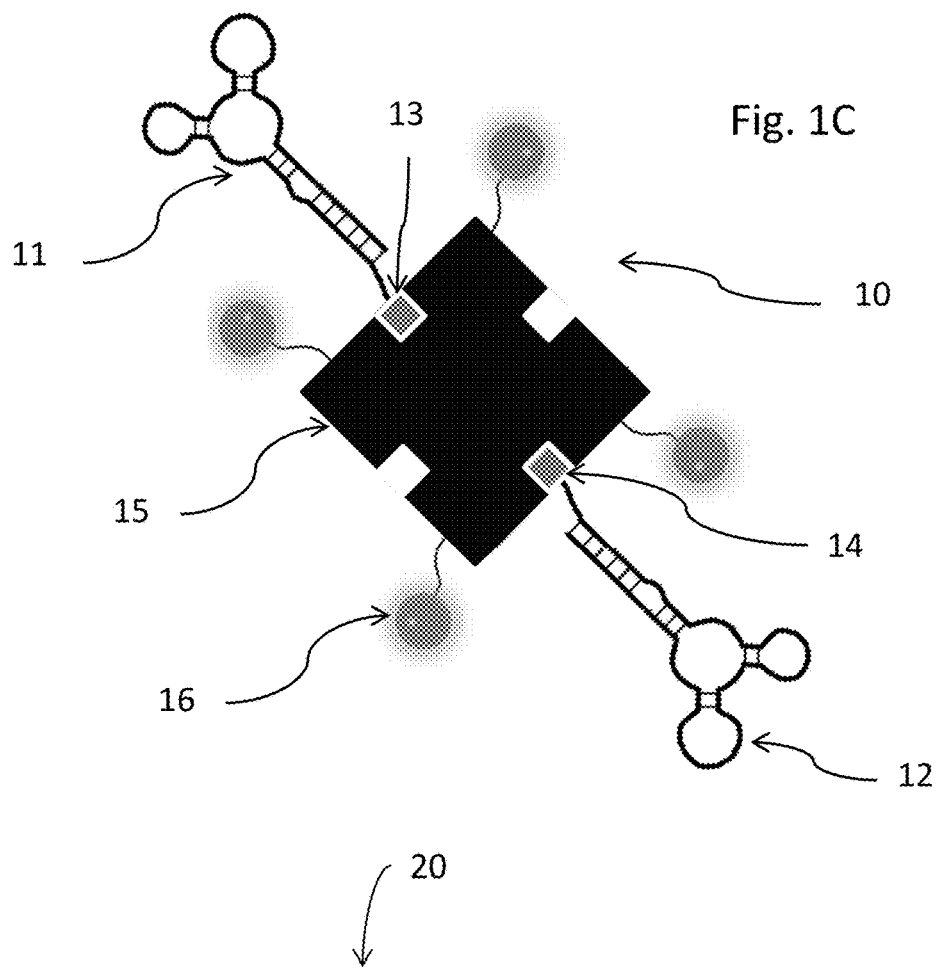
FIG. 1C illustrates a fluorescently labeled multivalent aptamer E07-SA.

The ability to reversibly label cells without compromising their viability or function is a valuable and versatile tool for the sorting or identification of cells within heterogeneous populations of cells. This technology serves as an adaptable platform that may be tailored by the selection of aptamer-antidote pairs to suit a myriad of research and clinical applications. Here, we demonstrate that aptamers may be used to identify and/or sort cells by binding with molecular targets while also retaining the aptamer-exclusive benefit of antidote-mediated reversibility. As a result, this technology allows for the positive sorting and/or identification of cells within a heterogeneous population and, afterward, returning the cells to their native state.

Aptamers

As used herein, the term "aptamer" refers to single-stranded DNA or RNA oligonucleotides that bind specifically to molecular targets with high affinity. The aptamer may bind a molecular target with a $K_d<1$ µM, 500 nM, 250 nM, 100 nM, 50 nM, 10 nM, 1 nM, 0.5 nM or 0.1 nM. Molecular targets may include, without limitation, proteins, lipids, carbohydrates, other types of molecules, or any specified binding site thereof. The molecular targets may be surface bound to a membrane. A "surface-bound molecular target" may be any molecular target associated with a membrane, including, without limitation, integral or peripheral membrane proteins, glycoproteins, lipoproteins, glycolipids. As shown in the Examples below, the aptamers used herein bind to a surface-bound molecular target that is a cell surface receptor.

Aptamers may have a secondary structure characterized by loop and/or stem regions. A "loop region" indicates that the nucleotides in this region are not expected to base pair with any other nucleotides in the aptamer. A "stem region" indicates that the nucleotides in this particular region of the aptamer are expected to be paired and aligned with the nucleotides in a corresponding region of the aptamer that is a reverse complement, stabilizing the secondary structure of the aptamer. As is well known in the art, adenine forms hydrogen bonds with uracil or thymine and cytosine and guanine also form hydrogen bonds with each other in both DNA and RNA molecules. The bases align with their reverse complement either on separate nucleic acid strands or on the same nucleic acid strand.

Aptamers have at least one binding motif. A "binding motif" is a portion of the oligonucleotide sequence that binds specifically to a molecular target with high affinity and may be characterized by particular loop and/or stem regions or particular nucleotides or bases in the aptamer.

The aptamers described herein may be monovalent or multivalent aptamers. A "monovalent" aptamer has one binding motif. A "multivalent" aptamer has two or more binding motifs on either the same oligonucleotide strand or different oligonucleotide strands. In some cases, the multivalent aptamer is a "bivalent" aptamer having 2 binding motifs, a "trivalent" aptamer having 3 binding motifs, or a "tetravalent" aptamer having 4 binding motifs. For some multivalent aptamers, all of the binding motifs may be the same. In other words, the binding motifs may each comprise the same oligonucleotide sequence that binds specifically to the same molecular target. Alternatively, at least one of the binding motifs may be different from another binding motif and, in particular cases, all of the binding motifs are different from any other binding motif. In other words, the binding motifs comprise differing oligonucleotide sequences capable of specifically binding different molecular targets.

Aptamers can be generated against target molecules by screening combinatorial oligonucleotide libraries for high affinity binding to the target (See, e.g., Ellington and Szostak, Nature 1990; 346: 8 18-22 (1990), Tuerk and Gold, Science 249:505-10 (1990)). The aptamers disclosed herein may be synthesized using methods known in the art. For example, the disclosed aptamers may be synthesized using standard oligonucleotide synthesis technology employed by various commercial vendors including Integrated DNA Technologies, Inc. (IDT), Sigma-Aldrich, Life Technologies, or Bio-Synthesis, Inc.

A person skilled in the art would also recognize that while the aptamers provided herein are RNA aptamers, the aptamers may be made of modified nucleotides or may include some deoxyribonucleotides, 2'-fluoro (2'-F), 2'-O-methyl (2'-OMe), 2'hydroxyl groups (2'-OH), or 3'-inverted deoxythymidine (idT) residues or other modifications in the RNA. Residue modifications may be added to increase stability from nuclease degradation. The aptamers may also be protected from RNase degradation by 3' or 5' modifications to the aptamer or by inclusion of modified bases such as locked nucleic acids (LNAs) or peptide nucleic acids (PNAs).

A "sorting aptamer" comprises an aptamer that binds specifically to molecular targets with high affinity useful for sorting and/or identifying cells associated with the molecular target. The staining aptamer comprises an oligonucleotide having 3D structure and a sorting label. A "sorting label" may include any suitable chemical or substance that may be used to sort a heterogeneous population of cells into subpopulations of cells or to identify a subpopulation of cells within a heterogeneous population of cells. The sorting label may be a reporter label, a magnetic label, or a binding label.

As used herein, a "heterogeneous population of cells" is a population of cells that may be subdivided into subpopulations possessing or lacking a distinguishing characteristic such as the presence of absence of a molecular target associated with a cell. Heterogeneous populations of cells may be prepared from biological samples, including biological fluids comprising cells or tissues, but need not be. Biological fluids may be used with or without processing prior to the cells within the fluid being contacted with any of the sorting aptamers described herein. Tissues may be used with processing to prepare cell suspensions, such as a single cell suspension, prior to cells being contacted with any of the sorting aptamers described herein.

A "reporter label" may include any suitable chemical or substance that may be detected as a signal or contrast using imaging techniques. Reporter moieties are well known in the art and have been summarized in, for example, James and Gambhir, *Physiol Rev* 92: 897-965 (2012). In some embodiments, a reporter label may include a fluorophore moiety, an optical moiety, a magnetic moiety, a radiolabel moiety, an X-ray moiety, an ultrasound imaging moiety, a photoacoustic imaging moiety, a nanoparticle-based moiety, or a combination of two or more of the listed moieties. A reporter label may also include a therapeutic reporter such as a radionuclide used in radiotherapy or a porphyrin used in photodynamic therapy.

A "fluorophore moiety" may include any molecule capable of generating a fluorescent signal. Various fluorophore moieties are well-known in the art and/or commercially available. Exemplary fluorophore moieties include, without limitation, fluorescein; FITC; Alexa dyes such as Alexa Fluor 488 (Af488), Alexa Fluor 660 (AF660), Alexa Fluor 680 (AF680), Alexa Fluor 750 (AF750), and Alexa Fluor 790 (AF790) (Life Technologies); Cy dyes such as Cy2, Cy3, Cy3.5, Cy5, Cy5.5 and Cy7 (GE Healthcare); DyLight dyes DyLight 350, DyLight 488, DyLight 594, DyLight 650, DyLight 680, DyLight 755 (Life Technologies); IRDye dyes such as IRDye 800CW, IRDye 800RS, and IRDye 700DX (Li-Cor); VivoTag dyes such as VivoTag680, VivoTag-S680, and VivoTag-S750 (PerkinElmer).

An "optical moiety" may include but are not limited to any agents that may be used to produce contrast or signal using optical imaging such as luminescence or acousto-optical moieties.

A "magnetic moiety" may include a chelating agent for magnetic resonance agents. Chelators for magnetic resonance agents may be selected to form stable complexes with paramagnetic metal ions, such as Gd(III), Dy(III), Fe(III), and Mn(III).

Other exemplary reporter moieties include "radiolabel moieties." Exemplary radiolabel moieties include, without limitation, $^{99m}$Tc, $^{64}$Cu, $^{67}$Ga, $^{186}$Re, $^{188}$Re, $^{153}$Sm, $^{177}$Lu, $^{67}$Cu, $^{123}$I, $^{124}$I, $^{125}$I, $^{11}$C, $^{X}$3N, $^{15}$O, and F. Exemplary reporter moieties may also include therapeutic radiopharmaceuticals including, without limitation, $^{186}$Re, $^{188}$Re, $^{153}$Sm, $^{57}$Cu, $^{105}$Rh, $^{m}$Ag, and $^{192}$Ir.

An "x-ray moiety" may include any agents that may be used to produce contrast or signal using X-ray imaging such as iodinated organic molecules or chelates of heavy metal ions.

An "ultrasound imaging moiety" may include any agents that may be used to produce contrast or signal using ultrasound targeted microbubbles such as Levovist, Albunex, or Echovist.

A "photoacoustic imaging moiety" may include photoacoustic imaging-compatible agents such as methylene blue, single-walled carbon nanotubes (SWNTs), and gold nanoparticles.

A reporter label may also be a nanoparticle-based moiety. A "nanoparticle-based moiety" may include a nanoparticle that is capable of generating a signal. For example, silicon containing nanoparticles may be used to produce fluorescence, luminescence, or other type of signal. Other exemplary nanoparticle-based moieties include, for example, nanospheres such as Kodak X-SIGHT 650, Kodak X-SIGHT 691, Kodak X-SIGHT 751 (Fisher Scientific); metal oxide nanoparticles; and quantum dots such as Evi-Tags (Evident Technologies) or Qdot probes (Life Technologies).

A "magnetic label" may comprise any ferromagnetic, super paramagnetic, or paramagnetic solid phase such as a colloidal particle, microsphere, nanoparticle, or bead. The magnetic label may comprise iron oxides of magnetite $Fe_3O_4$ or maghemite $\gamma$-$Fe_2O_3$; ferromagnetic metals such as Fe, Ni and Co; oxide ferrites of the form MeO·$Fe_2$O where Me may be Mg, Zn, Mn, Ni, or Co; platinum compounds such as CoPt3 or FePt; or any combination thereof. The magnetic label may have a diameter of 1 nm to 100 micron. Magnetic labels having a diameter of 1 nm to 100 nm or 10 nm to 50 nm may be used where a high number of magnetic labels are intended to be bound to a cell whereas magnetic labels having a diameter of 1 micron to 100 microns or 1 micron to 10 microns may be used where a low number of magnetic labels are intended to be bound to a cell.

A "binding label" comprises any label capable of binding another agent with a high affinity. Several binding labels are well-known in the art and include, without limitation, biotin, avidin, streptavidin, NeutrAvidin, digoxigenin, or anti-digoxigenin antibodies. In some embodiments, the sorting aptamer may be modified at either the 5' or 3' end to include biotin. Alternatively, the aptamer may be modified at either the 5' or 3' end to include streptavidin or avidin.

The aptamer and sorting label may be "linked" either covalently or noncovalently. Additionally, the aptamer and sorting label may be linked using a linker or spacer moiety. Useful linker or spacer moieties include peptides, amino acids, nucleic acids, as well as homofunctional linkers or heterofunctional linkers. Particularly useful conjugation reagents that can facilitate formation of a covalent bond between an aptamer and reporter label may comprise an N-hydroxysuccinimide (NHS) ester and/or a maleimide or using click chemistry. The aptamer and sorting label may be linked at the 5' end or the 3' end of the aptamer or may be linked at any nucleotide internally if the nucleotide is first modified with the required functional group.

The aptamer and the sorting label may be linked using a tag system. A "tag system" may include any group of agents capable of binding one another with a high affinity. Several tag systems are well-known in the art and include, without limitation, biotin/avidin, biotin/streptavidin, biotin/NeutrAvidin, or digoxigenin (DIG) systems. In some embodiments, said tag system comprises biotin/avidin or biotin/streptavidin. In such embodiments, the aptamer may be modified at either the 5' or 3' end to include biotin while the reporter label may be modified to include streptavidin or avidin. Alternatively, the aptamer may be modified at either the 5' or 3' end to include streptavidin or avidin while the sorting label may be modified to include biotin.

Different binding motifs may be linked either covalently or noncovalently by similar chemistries to those described above for linking an aptamer to a sorting label.

A variety of aptamers are described and used in the Examples herein. E07 is an epidermal growth factor receptor (EGFR) antagonizing aptamer. As used herein, and throughout the Examples, "E07" means an RNA oligonucleotide (SEQ ID NO: 1) that may comprise 2'fluoro (2'F) pyrimidines and modified at the 3'-end with an inverted thymidine (idT). Depending on context "E07" may be modified with a reporter label at the 5'-end with an Alexa Fluor 488 (AF488) or Alexa Fluor 647 (AF647) fluorescent dye (FIG. 1A). "bE07" means an RNA oligonucleotide (SEQ NO: 5) modified with a biotin binding label at the 5'-end (FIG. 1B). "C36" (SEQ ID NO: 2) and "bC36" (SEQ ID NO: 8) are unrelated, nonbinding controls for E07 and bE07, respectively.

Monovalent or multivalent aptamer conjugates may also be prepared. An "aptamer conjugate" comprises an aptamer comprising a binding label noncovalently or covalently associated with a linker capable of binding one or more binding labels with a high affinity. The linker may further comprise a reporter label and/or a magnetic label. FIG. 1C illustrates a bivalent aptamer-conjugate 10 comprising a first aptamer 11 and a second aptamer 12 linked via binding labels 13 and 14, respectively, to a linker 15. As shown, the linker 15 comprises reporter labels such as reporter label 16. As shown, the first aptamer 11 and the second aptamer 12 are the same, but one of ordinary skill will recognize that they need not be. In some embodiments, the number of aptamers linked to the linker 15 may be any number between 1 and the number of binding sites of the linker 15 such as 1, 2, 3, or 4.

As used herein, "E07-SA" is an aptamer conjugate comprising bE07 and streptavidin linker and "C36-SA" is an aptamer conjugate comprising bC36 and a streptavidin linker, "E07-SA-AF488" and "E07-SA-AF647" are bE07 aptamer-streptavidin conjugates comprising fluorescently labeled streptavidin with AF488 or AF647, respectively.

Oligonucleotide sequences for the aptamers and primer sequences are provided in Table 1.

TABLE 1

Sequences of aptamers and primers

| Oligo | Nucleic Acid Type | Sequence | SEQ ID NO: | Production | Modification |
|---|---|---|---|---|---|
| E07 | 2'F C/U RNA | 5'-GGA CGG AUU UAA UCG CCG UAG AAA GCA UGU CAA AGC CGG AAC CGU CC idT-3' | SEQ ID NO: 1 | Synthesis | 5' AF488 3' idT |
| C36 | 2'F C/U RNA | 5'- GGC GUA GUG AUU AUG AAU CGU GUG CUA AUA CAC GCC idT-3' | SEQ ID NO: 2 | Synthesis | 5' AF488 3' idT |
| bE07 forward primer | DNA | 5'-GAT AAT ACG ACT CAC TAT AGG GAT TTA GGA CGG ATT TAA TCG CCG TAG AA-3' | SEQ ID NO: 3 | Synthesis | |
| bE07 reverse primer | DNA | 5' -GGA CGG TTC CGG CTT TGA CAT GCT TTC TAC GGC GAT TAA ATC CGT CCT AAA TCC C-3' | SEQ ID NO: 4 | Synthesis | |
| bE07 | 2'F C/U RNA | 5'-GGG AUU UA GGA CGG AUU UAA UCG CCG UAG AAA GCA UGU CAA AGC CGG AAC CGU CC-3' | SEQ ID NO: 5 | Transcription | 5' biotin |
| bC36 forward primer | DNA | 5'-GAT AAT ACG ACT CAC TAT A GGA AAA TA GGC GTA GTG ATT ATG AAT CGT-3' | SEQ ID NO: 6 | Synthesis | |

TABLE 1-continued

Sequences of aptamers and primers

| Oligo | Nucleic Acid Type | Sequence | SEQ ID NO: | Production | Modification |
|---|---|---|---|---|---|
| bC36 forward primer | DNA | 5'- GGC GTG TAT TAG CAC ACG ATT CAT AAT CAC TAC GCC TA TTT TCC-3' | SEQ ID NO: 7 | Synthesis | |
| bC36 | 2'F C/U RNA | 5'-GGA AAA UA GGC GUA GUG AUU AUG AAU CGU GUG CUA AUA CAC GCC-3' | SEQ ID NO: 8 | Transcription | 5'-biotin |

Antidotes

Antidotes are also provided herein. An "antidote" is a DNA or RNA oligonucleotide capable of hybridizing via base complementarity to the aptamer resulting in a secondary structure change of the aptamer and thus preventing and even reversing the binding of an aptamer to its target. An antidote may include a nucleotide sequence having 50%, 60%, 70%, 80%, 90%, 95%, or 100% sequence identity to a sequence reverse complementary to and/or capable of hybridizing to at least 5, 6, 7, 8, 9, 10, 11, 12, 13, 14, 15, 16, 17, 18, 19, or 20 nucleotides present in the aptamers. Those skilled in the art will appreciate that the sequences would be altered to include thymines in place of the uracils when in a DNA form. As shown in the Examples, the antidotes included 2'-O-methyl RNA modified antidotes. Other modified nucleic acids could also be used in the antidotes as described above for the aptamers such as 2'-fluoro modified nucleic acids, LNAs or PNAs.

In some embodiments, the antidote comprises a single oligonucleotide sequence capable of hybridizing via base complementarity to the aptamer resulting in a secondary structure change of the aptamer and thus preventing and even reversing the binding of an aptamer to its target. In other embodiments, the antidote comprises a multiplicity of different oligonucleotide sequences capable of hybridizing via base complementarity to different portions of the aptamer resulting in a secondary structure change of the aptamer and thus preventing and even reversing the binding of an aptamer to its target. In some cases, the multiplicity of different oligonucleotide sequences comprises 2, 3, 4, or more different oligonucleotide sequences. The multiplicity of different oligonucleotide sequences may be a portion of the same oligonucleotide or different oligonucleotides. Different oligonucleotides may be covalently or non-covalently linked by chemistries described above for linking aptamers to sorting labels or other aptamers.

Antidotes can be generated against aptamers by screening complementary oligonucleotides by methods such as those described in the Examples. The antidotes disclosed herein may be synthesized using methods known in the art. For example, the disclosed antidotes may be synthesized using standard oligonucleotide synthesis technology employed by various commercial vendors including Integrated DNA Technologies, Inc. (IDT), Sigma-Aldrich, Life Technologies, or Bio-Synthesis, Inc.

Oligonucleotide sequences for the screened antidotes are provided in Table 2.

TABLE 2

Screened antidote sequences

| Antidote | Sequence | SEQ ID NO |
|---|---|---|
| A1 | 5'-TAC GGC GAT TAA ATC-3' | SEQ ID NO: 9 |
| A2 | 5'-TCT ACG GCG ATT AAA-3' | SEQ ID NO: 10 |
| A3 | 5'-TTT CTA CGG CGA TTA-3' | SEQ ID NO: 11 |
| A4 | 5'-GCT TTC TAC GGC GAT-3' | SEQ ID NO: 12 |
| A5 | 5'-ATG CTT TCT ACG GCG-3' | SEQ ID NO: 13 |
| A6 | 5'-ACA TGC TTT CTA CGG-3' | SEQ ID NO: 14 |
| A7 | 5'-TGA CAT GCT TTC TAC-3' | SEQ ID NO: 15 |
| A8 | 5'-TTT GAC ATG CTT TCT-3' | SEQ ID NO: 16 |
| A9 | 5'-GCT TTG ACA TGC TTT-3' | SEQ ID NO: 17 |
| mA9 | 5'-GCU UUG ACA UGC UUU-3' | SEQ ID NO: 18 |
| A10 | 5'-CGG CTT TGA CAT GCT-3' | SEQ ID NO: 19 |
| A11 | 5'-TCC GGC TTT GAC ATG-3' | SEQ ID NO: 20 |
| A12 | 5'-GTT CCG GCT TTG ACA-3' | SEQ ID NO: 21 |
| A13 | 5'-CGG TTC CGG CTT TGA-3' | SEQ ID NO: 22 |
| A14 | 5'-GCG ATT AAA TCC GTC-3' | SEQ ID NO: 23 |
| A15 | 5'-CGG CGA TTA AAT CCG-3' | SEQ ID NO: 24 |
| A16 | 5'-GAC GGT TCC GGC TTT-3' | SEQ ID NO: 25 |
| A17 | 5'-AGG ACG GTT CCG GCT-3' | SEQ ID NO: 26 |
| sA9 | 5'-ATC TAT TGT GTT CGC-3' | SEQ ID NO: 27 |

* Antidotes were comprised of DNA except for 2'-O-methyl RNA-based mA9

Methods of Using Sorting Aptamers

The aptamers and antidotes described herein may be used to reversibly stain live cells. The cells to be stained may be any type of cell. The cells to be stained may be obtained from a biological sample, such as a biological fluid or tissue, but need not be. As used herein "stain" means to associate a sorting label via the binding of a sorting aptamer with a molecular target on the surface of the cell, enhancing the ability to identify the cell within a heterogeneous population of cells or to sort a cell from a heterogeneous population of cells. The stain is "reversible" in that it prepares a sorted cell in its native state after the sorting aptamer is removed or unbound from the molecular target.

As used herein, "native state" means a live cell having cellular function substantially similar to its cellular function prior to binding the sorting aptamer and/or the cell is substantially free of surface-bound staining aptamer. A cell having substantially similar cellular function may mean that the cell has measurable cellular function within ±20%, ±15%, ±10% ±5%, ±4%, ±3%, ±2%, ±1%, or within a statistically relevant measure of error (e.g., a standard measure of error (SEM) or a standard deviation) of its measurable cellular function prior to binding the sorting aptamer. A cell substantially free of surface-bound sorting aptamer may mean that at least 80%, 85%, 90%, 95%, 96%, 97%, 98%, or 99% of the surface bound aptamer is removed. A cell substantially free of surface-bound sorting aptamer may mean that at least 80%, 85%, 90%, 95%, 96%, 97%, 98%, or 99% of the surface bound aptamer is removed. Native state may also mean that the cell is substantially free of combination with another article, such as an antidote, except for water, a crystalloid, a sterilizing agent, a preserving agent, or storage agent. Substantially free in this context may mean that any modulation of cellular function attributable to the agent is less than ±20%, ±15%, ±10% ±5%, ±4%, ±3%, ±2%, ±1%, or within a statistically relevant measure of error (e.g., a standard measure of error (SEM) or a standard deviation) of its measurable cellular function prior to binding the sorting aptamer. Native state may also mean that the cell is minimally manipulated or has not been subjected to substantial manipulation. "Minimal manipulation" means processing that does not alter the original relevant characteristics of the tissue relating to the tissue's utility for reconstruction, repair, or replacement or processing that does not alter the relevant biological characteristics of cells or tissues. Manipulations such as cutting, grinding, shaping, centrifugation, soaking in antibiotic or antimicrobial solution, sterilization, irradiation, cell separation, cell concentration, cell purification, filtering, lypophilization, freezing, cryopreservation, or vitrification are not substantial manipulations.

The cells after use in the methods described herein may be implanted, transplanted, infused, or transferred into a subject. As used herein, a "subject" may be interchangeable with "patient" or "individual" and means an animal, which may be a human or non-human animal, in need of treatment. A "subject in need of treatment" may include a subject having a disease, disorder, or condition that is responsive to cell-based therapy with a cell sorted or isolated by the methods and compositions described herein.

Figure 2A:
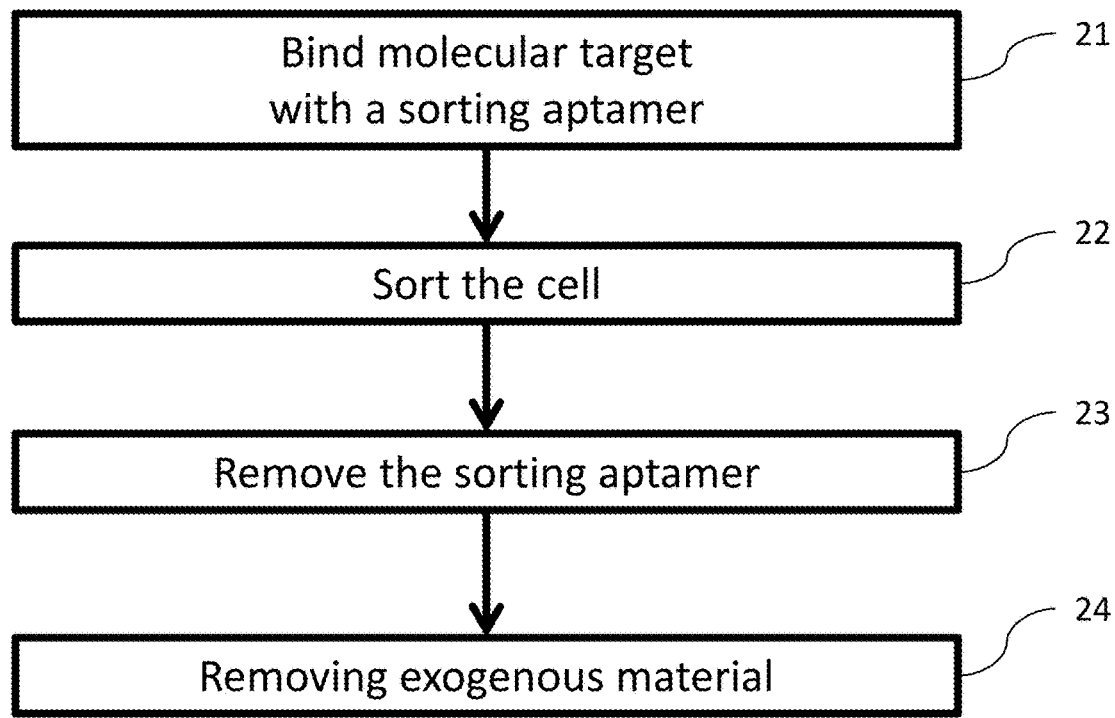
FIG. 2A illustrates an overview of sorting aptamer-stained target cells followed by antidote treatment to remove the aptamer and restore native cell function.

The method 20 of using the sorting aptamer is generally illustrated in FIG. 2A. As shown in FIG. 2A, the method comprises binding a molecular target associated with a cell within a heterogeneous cell population with a sorting aptamer 21, sorting the cell from the heterogeneous population 22, and removing the sorting aptamer from the molecular target 23. Alternatively, the sorting step 23 may be an identification step where the cell is identified within the heterogeneous population or the sorting step 23 may be a combination of identification and sorting steps. Optionally, the method may further comprise removing exogenous material 24.

The alternatives described may be implemented by different means and/or for different purposes. As used herein "sorting" generally means physically separating cells within the heterogeneous population into subpopulations based on a distinguishing characteristic, e.g., a molecular target associated with the cell. As used herein "identifying" means detecting a distinguishing characteristic possessed by a subpopulation within a heterogeneous population. Some sorting techniques require identifying the distinguishing characteristic before sorting. Even if the sorting technique does not require identification, an optional identification step may be desirable to confirm the presence or absence of the distinguishing characteristic.

The method for sorting may be any suitable cell sorting technology. Numerous cell sorting techniques are known in the art, and a person of ordinary skill will understand how to modify a sorting aptamer based on the selection of the appropriate sorting label to implement the sorting technology. An example of a sorting technology, which is employed in the Examples described below, is fluorescence-activated cell sorting (FACS). FACS provides for a method for sorting cells within a heterogeneous population of cells into two or more containers, one cell at a time, based on identifying scattered light and/or fluorescence and then modulating an electric field in response to sort the cells into an appropriate container. When a sorting aptamer comprising a reporter label, such as a fluorophore moiety, binds to a cell associated molecular target, FACS may be used to identify light scattered and/or fluorescence from the reporter label and thereby sort the sorting aptamer and its associated cell.

Another example of a sorting technology that may be implemented with the technology described herein is magnetic-activated cell sorting (MACS) or other magnet label sorting technology. MACS provides for a method for sorting cells within heterogeneous population of cells by the application of a magnetic field to sequester magnetic materials. When a sorting aptamers comprising a magnetic label, such as a magnetic bead, binds to a cell associated molecular target, MACS may be used to sort the sorting aptamer and its associated cell. Identification of a distinguishing characteristic is not required prior to sorting, but may be optionally performed before or after sorting.

Another example of sorting technology that may be implemented with the technology described herein is cell capture techniques based on binding affinity. Capture techniques provide for a method of sorting cells by physically sequestering cells by specifically binding them to materials or substrates or, alternatively, by specifically binding to materials capable of being used in other sorting techniques. As an example of the latter type, a sorting aptamer comprising a binding label may be specifically bound to material comprising a reporter-type material, e.g., a biotinylated aptamer bound a fluorescently labeled streptavidin, to be separated by FACS. As another example, a sorting aptamer comprising a binding label may be specifically bound to material comprising a magnetic material, e.g., a biotinylated aptamer bound a streptavidin coated magnetic bead, to be separated by MACS.

The removing of the sorting aptamer may be accomplished in a number of different ways. As used herein "removing" the sorting aptamer means significantly reducing the number of sorting aptamers bound to molecular targets. In some cases, a significant reduction in the number of sorting aptamers bound to molecular targets means at least a 50%, a 60%, a 70%, a 80%, a 85%, a 90%, a 95%, a 96%, a 97%, a 98%, or a 99% reduction in the number of sorting aptamers bound to molecular targets. Removing the sorting aptamer may be accomplished by contacting any of the antidotes described herein with a sorting aptamer. When a suitable antidote is provided, the sorting aptamer and the antidote may fully or partially hybridize via base complementarity, resulting in a secondary structure change of the aptamer and thus preventing and even reversing the binding of an aptamer to its target. In addition, or possibly as an alternative to contacting the sorting aptamer with an antidote, the method may also comprise modulating the temperature to increase the effectiveness of removing the sorting aptamer. In some cases, temperature is increased by at least 1K, 5K, 10K, 15K, 20K, 25K, or 30K. The temperature may also be modulated by cycling the temperature between a mean maximum and minimum separated by at least 1K, 5K, 10K, 15K, 20K, 25K, or 30K. Because an object of the invention is to be able to provide for cells in their native state after use in the method, temperature modulation should be performed such that cellular function is not irreversibly harmed or results in an inactivated or killed cell. In addition, or possibly as an alternative to contacting the sorting aptamer with an antidote, the method may also comprise modulating a concentration of a divalent ion to increase the effectiveness of removing the sorting aptamer. The divalent ion may be a divalent cation such a $Mg^{2+}$, $Ca^{2+}$, or $Mn^{2+}$. In addition, or possibly as an alternative to contacting the sorting aptamer with an antidote, the method may also comprise providing a material comprising a polycationic polymer to increase the effectiveness of removing the sorting aptamer. Examples of materials comprising polycationic polymers include those described in U.S. Patent Pub. Nos. US 2010/0184822, US 2012/0183564, and US 2017/0037544 as well as International Patent Pub. Nos. WO/2014/169043 and WO/2017/079638 and International Patent Appl. No. PCT/US2017/068262.

The method 20 may further comprise removing exogenous material 24. "Exogenous material" may include any foreign material such as a sorting aptamer and/or an antidote. The removal step may be accomplished by washing the sorted cells with a solution or a cell culture medium. In some embodiments, the removal step assists in the dissociation of the sorting aptamer and/or antidote from the cell.

Figure 2B:
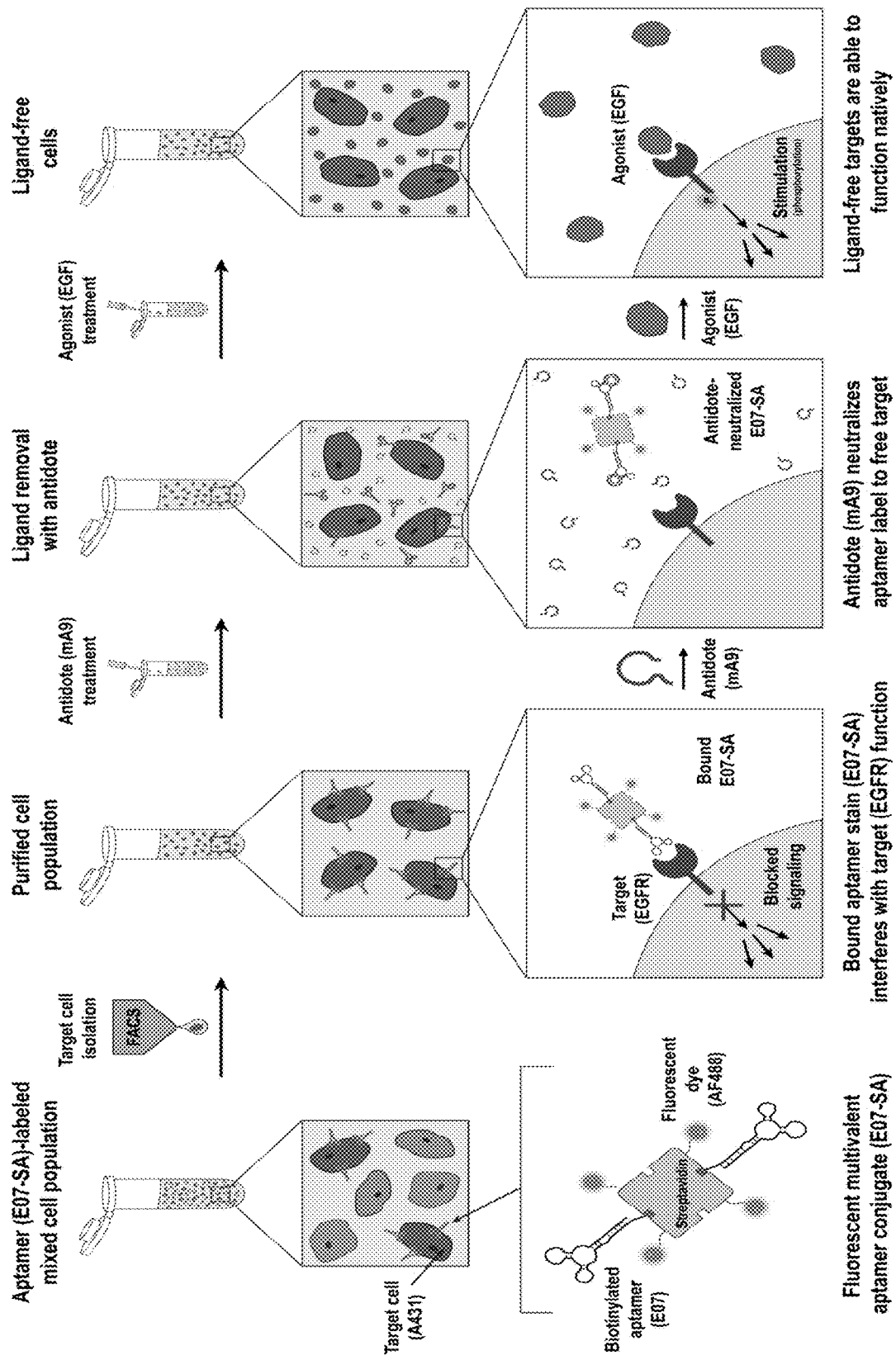
FIG. 2B illustrates an overview of sorting aptamer-stained target cells followed by antidote treatment to remove the aptamer and restore native cell function with a multivalent aptamer conjugate comprising bE07 complexed with a fluorescently-labeled streptavidin linker.

FIG. 2B illustrates an overview of sorting aptamer-stained target cells followed by antidote treatment to remove the aptamer and restore native cell function. Target cells of an initially heterogeneous population are selectively labeled with an aptamer and then isolated using a conventionally antibody-based purification scheme such as fluorescence-activated cell sorting (FACS). However, the utility of purified target cells may be compromised as residual ligand on purified cells can interfere with their native functions. Unlike antibody-based stains, treatment of aptamer-stained cells with matched antidotes allows sorting-ligand removal, enabling cells to function normally in downstream research and clinical applications. As shown in the Examples, the disclosed technology using a fluorescently labeled multimer of the EGFR-antagonizing aptamer E07 (E07-SA) and a matched antidote (mA9) to stain, sort and "destain" epidermoid carcinoma (A431) cells ahead of probing targeted receptor function.

The methods described above may be extended to include a multiplicity of different sorting aptamers. In one embodiment, sub-subpopulations may be sorted from a heterogeneous population of cells by the serial application of the methods described above. A first sorting aptamer may be bound to cells within a heterogeneous population, allowing the cells to be sorted for the presence or absence of a first distinguishing characteristic into a second heterogeneous population. A second sorting aptamer may be bound to cells within the second heterogeneous population, allowing the cells to be sorted for the presence or absence of a second distinguishing characteristic. Depending on the sorting techniques employed, the first aptamer may be removed before or after the introduction of the second aptamer. Those of skill in the art will readily recognize that the serial application can be extended for any number of sorting aptamers. The sorting aptamers used in this embodiment may have the same sorting labels or different sorting labels.

In an alternative embodiment, sub-subpopulations may be sorted from a heterogeneous population of cells by the simultaneous application of a multiplicity of sorting aptamers or by multivalent aptamers having differing binding motifs and the sequential application of antidotes specific for individual sorting aptamer. A first sorting aptamer and a second sorting aptamer or a multivalent aptamer may be bound to cells within a heterogeneous population, allowing the cells to be sorted into a second heterogeneous population. An antidote specific for the first sorting aptamer or first binding motif may reverse the staining for that aptamer or binding motif, allowing for the cells of the second heterogeneous population to be sorted again. Those of skill in the art will readily recognize that method may be extended for any number of sorting aptamers or binding motifs.

Conclusions

The ability to reversibly stain cells without compromising their viability or function is a valuable, versatile tool with important implications for both the lab and clinic. The Examples presented herein demonstrate the utility of this technology. Even more promising is the prospect of using purified multivalent aptamer constructs, which are predicted to perform at least as well as monoclonal antibodies while retaining the aptamer-exclusive benefit of antidote-mediated reversibility. This methodology serves as an adaptable platform for other aptamer-antidote pairs that are able to suit a myriad of research and clinical applications.

Aptamers and matched antidotes for non-destructive, reversible cell staining offer an unrivaled cell purification platform. This technique is impactful because of the uncompromised utility of cells purified using it. The staining-sorting-destaining workflow was successful in removing nearly all of the aptamer and had no negative impact on cell viability or function. Multivalent aptamers, even in the form of a heterogeneous mixture containing a large fraction of monomer, offered near-antibody stability but were also completely reversible via antidote treatment. Imperfect destaining does not contraindicate aptamer-sorted cells for therapeutic use in vivo as they are not immunogenic like antibodies. Since aptamers can be raised against various molecular targets using systematic evolution of ligands by exponential enrichment (SELEX) and matched antidote libraries may be designed based on the aptamer sequence, the present technology is extendable to virtually any cell type.

This method could also be useful for serially sorting a cell population for multiple biomarkers using a single fluorophore. Research environments with limited resources may only have a single-laser (color) sorter but need to purify a specific subpopulation of cells defined by a set of surface markers. Using antibodies, cells could only be sorted for one marker as the stain is permanent and sorting the population again with another antibody possessing the same fluorophore would be messy or impossible. However, sets of aptamer-antidote pairs all labeled with the same fluorophore would provide a clean slate after each sort to allow sequential sorts in the same channel and eventually allow the population of interest to be isolated.

Reversible cell staining technology is also useful for enhancement of targeted in vivo imaging. Administering labeled aptamer intravenously enables its concentration in targeted tissues for imaging. A follow-up treatment with antidote treatment to neutralize the aptamer more readily removes non-specifically bound aptamer contributing to background signal and improves contrast to better visualize the targeted tissue of interest.

Miscellaneous

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference in their entirety, unless explicitly indicated otherwise. The present disclosure shall control in the event there are any disparities between any definitions and/or description found in the cited references.

Unless otherwise specified or indicated by context, the terms "a", "an", and "the" mean "one or more." For example, "a protein" or "an RNA" should be interpreted to mean "one or more proteins" or "one or more RNAs," respectively.

The following examples are meant only to be illustrative and are not meant as limitations on the scope of the invention or of the appended claims.

EXAMPLES

Materials and Methods

General

Buffers, reagents and experimental samples were maintained at 4° C. either on ice or in refrigerated centrifuges during all procedures unless otherwise stated. Care was taken to minimize ambient light exposure of fluorescent samples. Media supplemented only with 1% bovine serum albumin ("Media+") was universally used for staining and antidote solutions, washes and as a flow cytometry buffer. All phosphate-buffered saline (PBS+/+) contained $Ca^{2}+$ and $Mg^{2}+$ unless otherwise noted.

Cell Culture

A431 epidermoid carcinoma cells sourced from the American Type Culture Collection (ATCC) were obtained through the Duke Cell Culture Facility. A431 cells were maintained at 37° C. and 5% $CO_2$ in growth media (Sigma, high-glucose Dulbecco's Modified Eagle's Medium containing L-glutamine, sodium pyruvate, and sodium bicarbonate with 4.5 g/L glucose) supplemented with 10% non-heat inactivated FBS (Gibco), 100 U/mL penicillin and 100 µg/mL streptomycin per ATCC recommendations. Cells were passaged at 70-90% confluency using 0.25% trypsin-EDTA (Gibco) and split 1:2-1:4 into new tissue culture flasks. Experiments utilized A431 cells between passage numbers 32 and 38.

Chemical Synthesis of Aptamers

E07 and non-specific control C36 RNA aptamers (sequences in Table 1) were synthesized by solid phase synthesis on an Expedite 8909 DNA synthesizer (Biolytic Lab Performance). Briefly, all aptamers were synthesized with 2'fluoro (2'F) pyrimidines, 2'OH purines and 5' thiols (using a C6 S—S phosphoramidite) on an inverted dT CPG column. Aptamer sequences are provided in Table 1. Synthesis reagents were purchased from Glen Research and Chemgenes. The aptamers were reversed-phase HPLC purified using a linear gradient of acetonitrile in 0.1 M TEAA, pH 7.5, on a 10×50 mm Xbridge C18 column (Waters) at 65° C.

To prepare for dye conjugation, 5' thiol-aptamers were reduced in 0.1 M TEAA with 500 mM TCEP by heating at 70° C. for 3 min and incubating at RT for 57 min. After confirming thiol reduction by HPLC, TCEP was removed by buffer exchanging into PBS (without $Ca^{2}+$ and $Mg^{2+}$) +2 mM EDTA using Amicon Ultra 10 kD spin columns (Millipore) The reduced aptamers were then 5' labeled with Alexa Fluor 488 (AF488) or Alexa Fluor 647 (AF647) using the thiol-reactive AF488-05-maleimide or AF647-C2-maleimide dyes (Invitrogen). The dyes were dissolved in DMSO to a concentration of 20 mM and added to the reduced aptamers at 5-10 fold molar excess. Labeling efficiency was determined by analytical HPLC and routinely proceeded to 99%. Free dye was removed by washing labeled aptamers with 10 mM Tris-EDTA pH 7.5 (TE) in Amicon Ultra 10 kD spin columns. The concentration of dye-labeled aptamer was quantitated using a NanoDrop spectrophotometer (Thermo Scientific).

Biotinylated Aptamer Transcription and Aptamer-Streptavidin Conjugate Preparation E07 and C36 (sequences in Table 1) with 5'-biotinylated eight-nucleotide extensions (5'-biotin-GGA AAC UA-E07 or C36-3') were transcribed to enable conjugation to AF488 or AF647-labeled streptavidin (AF488-SA or AF647-SA; Thermo Fisher). The nucleotide extension was designed to ensure that the predicted secondary structure of E07 (mfold software) was not impacted (FIG. 1B). Double-stranded DNA (dsDNA) templates for both extended, biotinylated E07 (bE07) and C36 (bC36) containing T7 RNA polymerase (RNAP) promoters were generated by annealing purchased primers (Table 1; Integrated DNA Technologies, IDT) and using Klenow Fragment (NEB) to fill in the single-stranded overhangs. The dsDNA templates for bE07 and bC36 were subsequently transcribed using Y639F mutant T7 RNAP along with 2'F pyrimidine and 2'OH purine nucleotides doped with a 10-fold molar excess of 5'-biotin-G-monophosphate (TriLink Biotechnologies). Aptamers were purified on denaturing 12% polyacrylamide gels, extracted overnight at 4° C. into TE, pH 7.5, desalted in Amicon Ultra 10 kD spin columns (Millipore) and quantitated via absorbance at 260 nm on a spectrophotometer (Thermo Scientific).

Aptamers were folded in PBS+/+ by denaturation at 65° C. for 5 min followed by passive cooling to ambient temperature for 3 min. Aptamer-streptavidin conjugates (E07-SA or C36-SA) were then prepared by incubating folded bE07 or bC36 with AF488-SA or AF647-SA at a 2:1 molar ratio (RNA:SA) in PBS+/+ for 20 min at RT. The conjugates were directly used without further purification.

Staining Cells with Aptamers or Antibodies

All aptamers were folded in PBS+/+ by denaturation at 65° C. for 5 min followed by passive cooling to ambient temperature for 3 min. In general, 500 nM aptamer solutions were used for staining, but this concentration varied as noted in some assays. For aptamer-SA staining solutions, 2:1 aptamer conjugates were prepared with 1 µM aptamer and 500 nM AF488-SA or AF647-SA. All staining solutions were prepared in Media+ and contained 1 mg/mL salmon sperm DNA to mitigate non-specific binding. All antibodies were used as 1:50 dilutions in Media+ with 1 mg/mL salmon sperm DNA. Both FITC-conjugated ICR10 (Abcam) and PE-conjugated D1D4J (Cell Signaling Technologies) monoclonal EGFR antibodies were used for staining.

Flow Cytometry

Experiments utilized cells at 75-90% confluency that had been plated 48-72 hours in advance. Trypsin was used to harvest cells and immediately neutralized with growth media upon cell detachment. Cells were washed once with Media+, counted with a hemocytometer, and then $5\times10^5$ cells per sample were partitioned into chilled 1.5 mL microcentrifuge tubes. Staining was performed by resuspending cells in 100 µL of the appropriate antibody- or aptamer-staining solution (5 million cells per mL) and incubating for 30 min on ice. Stained cells were washed once with 500 µL Media+ and analyzed on BD FACSCalibur or BD FACSCanto II flow cytometers (BD Biosciences).

Apparent Binding Affinity Determination

The apparent binding affinities of E07 and E07-SA were computed from saturation cell binding curves. Cells were stained with 25, 50, 125, 250 or 500 nM E07 or E07-SA, washed and then analyzed by flow cytometry to obtain mean fluorescence intensities (MFI). Apparent dissociation constants ($K_D$) and saturation binding intensities ($B_{max}$) were determined by performing a non-linear regression in GraphPad Prism software to fit flow data to the single-site saturation binding equation $MFI=(B_{max}[aptamer])/(K_D+[aptamer])$.

Fluorescence Activated Cell Sorting (FACS)

Stained samples were filtered through 40 µm cell strainers, resuspended to 10 million cells per mL and kept on ice prior to sorting. Samples were separate, pure populations of treated cells. Sorting was performed at 30 psi and a rate of $5\times10^3$ cells per second on a BD DiVa (BD Biosciences) utilizing refrigeration to maintain both the sample and collection tubes at 4° C. Collection tubes contained 3 mL Media+ and approximately 1 mL sheath fluid (PBS without $Ca^{2+}$ or $Mg^{2+}$) was added per 0.5 million sorted cells. Sorting-associated losses were assessed by independently analyzing samples immediately prior to and after sorting on a BD FACSCalibur or BD FACSCanto II (BD Biosciences).

Antidote Screening Experiments

Single-stranded DNA antidotes 15 bases in length were designed to target various regions of E07 (SEQ ID 1) and purchased from IDT. Targeted regions were offset by two bases and together the antidotes probed the entirety of the E07 sequence. Antidote sequences were complementary to these targeted regions and are provided in Table 2. The 2'OMethyl (2'OMe) RNA antidote was purchased from Biosynthesis, Inc.

Relative antidote performance was assessed using a flow cytometry blocking assay. Experiments utilized cells at 75-90% confluency that had been plated 48-72 hours in advance. Trypsin was used to harvest cells and immediately neutralized with growth media upon cell detachment. Cells were washed once with Media+, counted with a hemocytometer, and then $5\times10^5$ cells per sample were partitioned into chilled 1.5 mL microcentrifuge tubes. Staining was performed by resuspending cells in 100 uL of 100 nM E07 either in the absence or presence of 100 µM antidote for 30 min at 37° C. Stained cells were washed once with 500 uL Media+ and analyzed by flow cytometry on BD FACSCalibur or BD FACSCanto II flow cytometers (BD Biosciences). The reduction in mean fluorescence intensity of antidote-treated cells relative to an untreated E07-stained control served as a metric for antidote effectiveness.

Destaining Cells

Stained cells maintained on ice were resuspended in 100 µL Media+ with or without antidote A9 DNA, 2'OMethyl RNA A9 (mA9) or scrambled control antidote sA9 DNA and incubated in a water bath at 37° C. for durations up to 30 min. Immediately after destaining, samples were placed back on ice. Cells were then washed once with Media+ and either analyzed by flow cytometry or subsequently used in EGF stimulation assays.

Cell Viability Assays

Viability of cells that had been stained, sorted and then destained was evaluated by using a LIVE/DEAD Fixable Near-IR Dead Cell Stain Kit (Thermo Fisher) according to the instructions of the manufacturer. Treated samples were then analyzed by flow cytometry on a BD FACSCanto II flow cytometer (BD Biosciences). Unstained sorted cells that had been heated at 65° C. for 20 min served as a positive (dead cell) control for gating.

EGF Stimulation Assays and Western Blotting

Cells were left unstained or stained with AF488 labeled C36-SA or E07-SA or with a PE-labeled D1D4J neutralizing monoclonal antibody against EGFR (Cell Signaling Technologies). Cells were subsequently sorted and then destained with or without 5 µM mA9 for 5 min at 37° C. After destaining, cells were stimulated with 5 nM EGF in Media+ for 15 min on ice and then lysed by resuspension in radioimmuniprecipitation (RIPA) buffer containing phosphatase and protease inhibitor cocktails (ThermoFisher Scientific). Lysate was either used immediately or frozen at −80° C. until use.

The amount of protein in crude lysate was quantified using a bicinchronic acid (BCA) assay kit (Thermo-Fisher Scientific) according to the instructions of the manufacturer. Crude lysate samples containing equal amounts of protein were prepared in Laemmli sample buffer containing 10% (β-mercaptoethanol, boiled for 5 min at 95° C. and then run on 4-15% denaturing polyacrylamide gels (Bio-Rad) in Tris/glycine/SDS buffer at 300V. Electrophoresed samples were blotted onto low-fluorescence polyvinylidene (PVDF) membranes with the Trans-Blot Turbo Transfer System and Transfer Packs (Bio-Rad) using the default setting for transfer of high molecular weight proteins. Membranes were blocked for 1 hour at RT with PBS containing 0.05% Tween 20 (PBST) and 5% bovine serum albumin (blocking buffer). Blocked membranes were incubated overnight at 4° C. in blocking buffer containing 1:1000 dilutions of primary monoclonal antibodies for total EGFR (mouse anti-human; Cell Signaling Technologies 2239S) and pEGFR (rabbit anti-human; Cell Signaling Technologies 4407S). Membranes were next washed 3× for 5 min with PBST on a rocker and then incubated with blocking buffer containing fluorophore-conjugated secondary antibodies for detection of total EGFR (1:10,000 dilution of goat anti-mouse AF546 conjugate; Life Technologies A11030) and pEGFR (1:20,000 dilution of goat anti-rabbit AF647 conjugate; Jackson Labs 111-605-144) in separate fluorescent channels without spectral overlap. Blots were washed in the same fashion and then imaged on a Chemidoc MP equipped with green and red LEDs that enabled fluorescent multiplexing (Bio-Rad). Bands corresponding to total EGFR and pEGFR were manually identified using rectangular volumes in Image Lab software (Bio-Rad), and the amount of each protein was taken as the background-adjusted intensity of each specified volume. The pEGFR/total EGFR ratio for each sample was normalized to the average ratio for stimulated unstained cells, which served as the positive control for native, uninhibited stimulation.

Statistics

Data were analyzed by one-way analysis of variance (ANOVA) and the Tukey-Kramer post hoc test in JMP software to establish significant differences between experimental conditions where appropriate. Significance was assumed at $p<0.05$.

Electrophoretic-Mobility Shift Assay (EMSA)

The valencies of aptamer-SA conjugates were characterized by EMSA as previously described (Maier, Jangra et al. 2016). Conjugate samples were prepared as detailed above by varying the amount of aptamer relative to a constant amount of SA. Aptamer-only samples serving as controls contained the same amount of aptamer as the 1:1 conjugate samples. Samples were combined with 2× formamide sample buffer supplemented with 1% SDS and run on an 8% denaturing polyacrylamide gel containing 0.1% SDS at 120V. Aptamer was visualized by staining gels with SYBR Gold (Thermo Fisher) followed by imaging on a ChemiDoc MP (Bio-Rad). Bands corresponding to conjugates of three different molecular weights (smallest, medium and largest) were manually identified using rectangular volumes in Image Lab software (Bio-Rad), and the amount of each aptamer was taken as the background-adjusted intensity of each specified volume. The amount of each size conjugate was normalized to that in the 1:1 conjugate mix for comparison.

Example 1

Aptamers as Reversible Sorting Ligands for Preparation of Cells in Their Native State To evaluate this novel approach, we used a fluorescent multimer of the well-characterized EGFR-antagonizing aptamer E07 (E07-SA) in conjunction with a matched antidote (mA9) to fluorescently label, purify via FACS and then de-stain an epidermoid carcinoma cell line (A431) that highly expresses EGFR (FIG. 2B). The effectiveness of mA9 to both remove E07-SA and restore aptamer-inhibited EGFR signaling to native levels was then evaluated.

An initial screen was performed to identify an effective antidote against monomeric E07 tagged with a 5' Alexa Fluor 488 (AF488) dye. Cells were incubated with E07 (Table 1) and an excess of 15 nucleotide long single-stranded DNA antidote candidates complementary to different regions of the aptamer sequence (Table 2), washed and then analyzed by flow cytometry. The most effective antidotes greatly reduced cell fluorescence by neutralizing E07 binding to cells (FIG. 3A), with antidote A9 emerging as the most effective antidote.

Figure 3A:
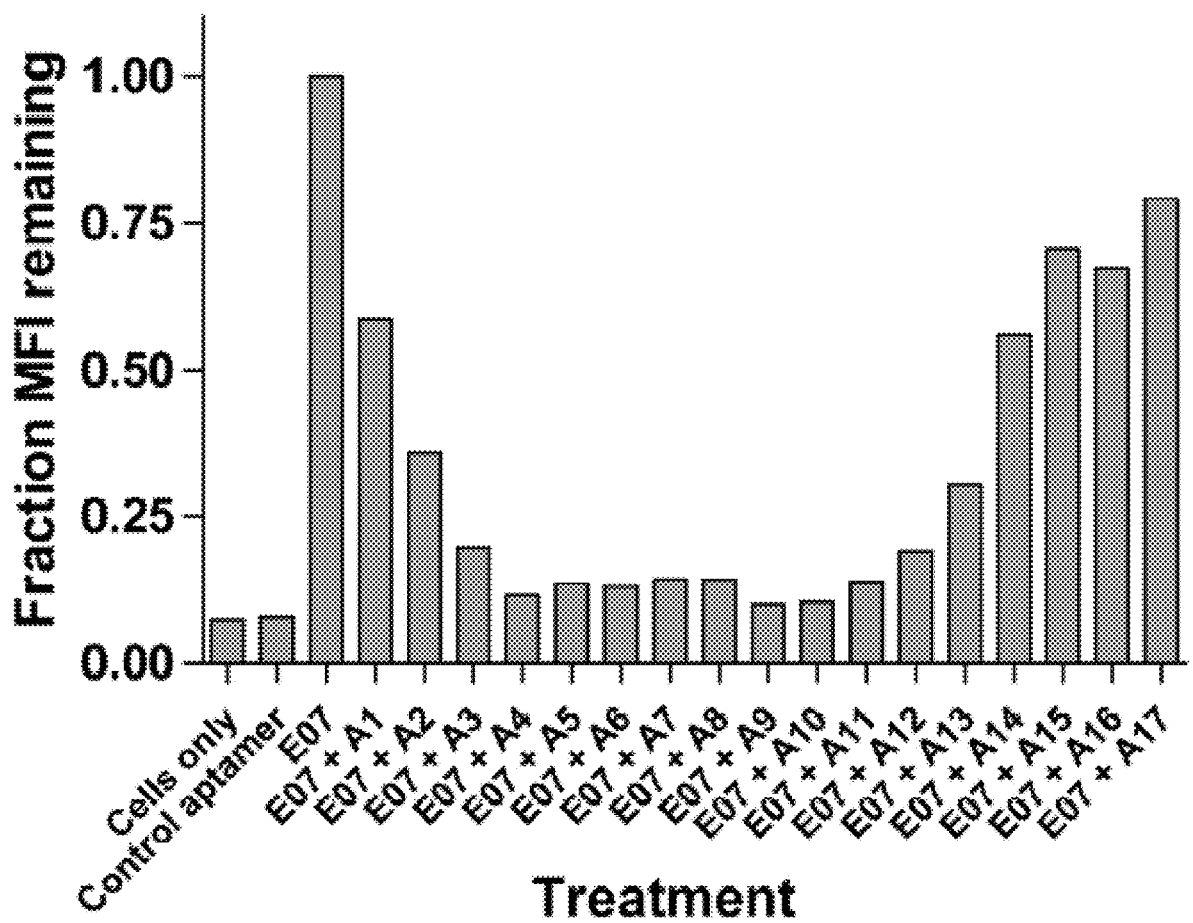
FIG. 3A shows the mean fluorescence intensity (MFI) detected in a screening assay to identity antidotes most capable of blocking E07 binding normalized by the MFI of cells treated with E07 alone. A431 cells were stained with AF488-E07 (or control aptamer AF488-C36)+/−a 1000-fold excess of each of the DNA antidote candidates and analyzed by flow cytometry.
Figures 3B, 3C:
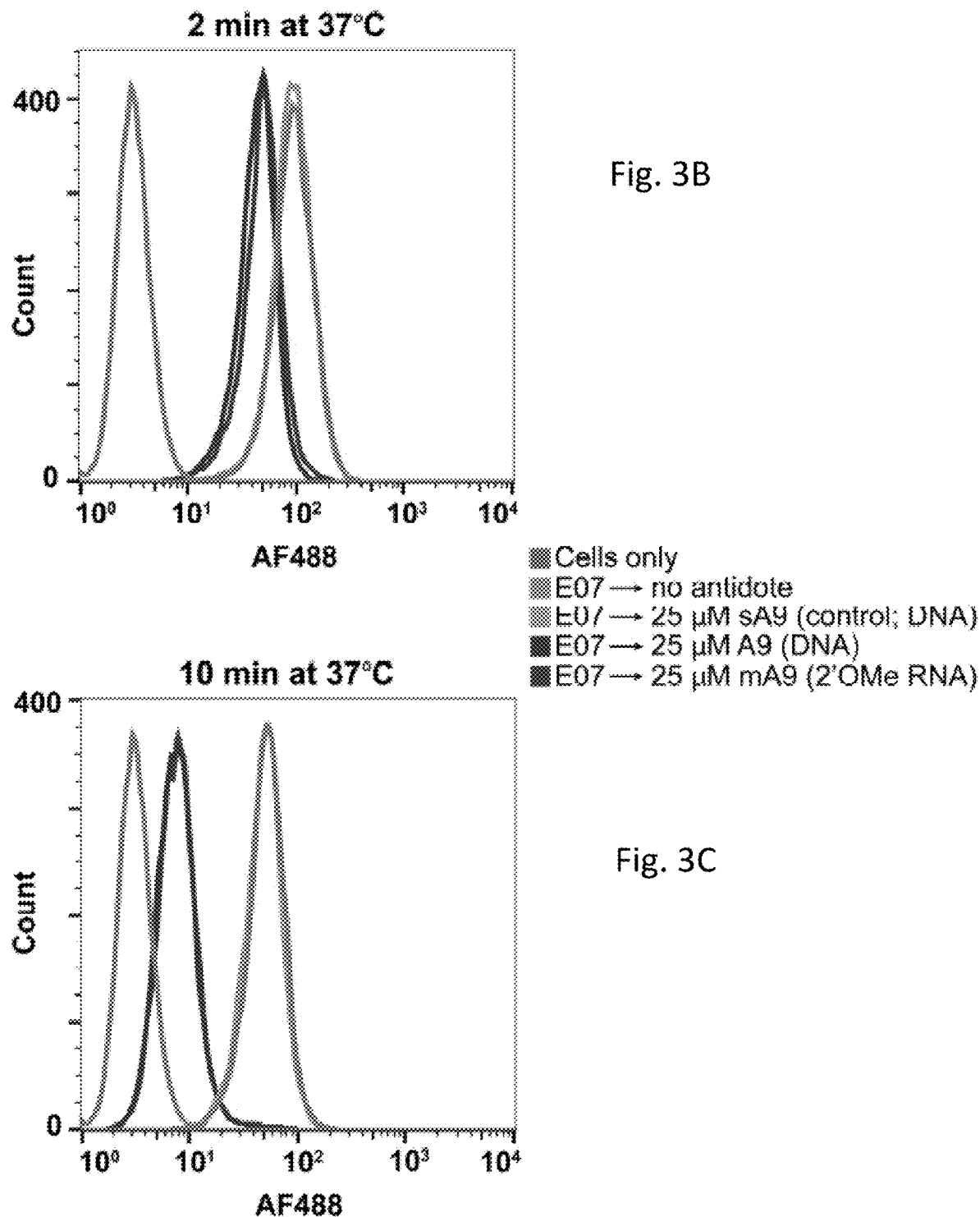
FIGS. 3B-3D show that both DNA-based A9 and its 2'OMe RNA analog mA9, but not a scrambled-sequence control antidote (sA9), enhanced removal of cell-bound E07 over time as analyzed by flow cytometry.
Figure 3D:
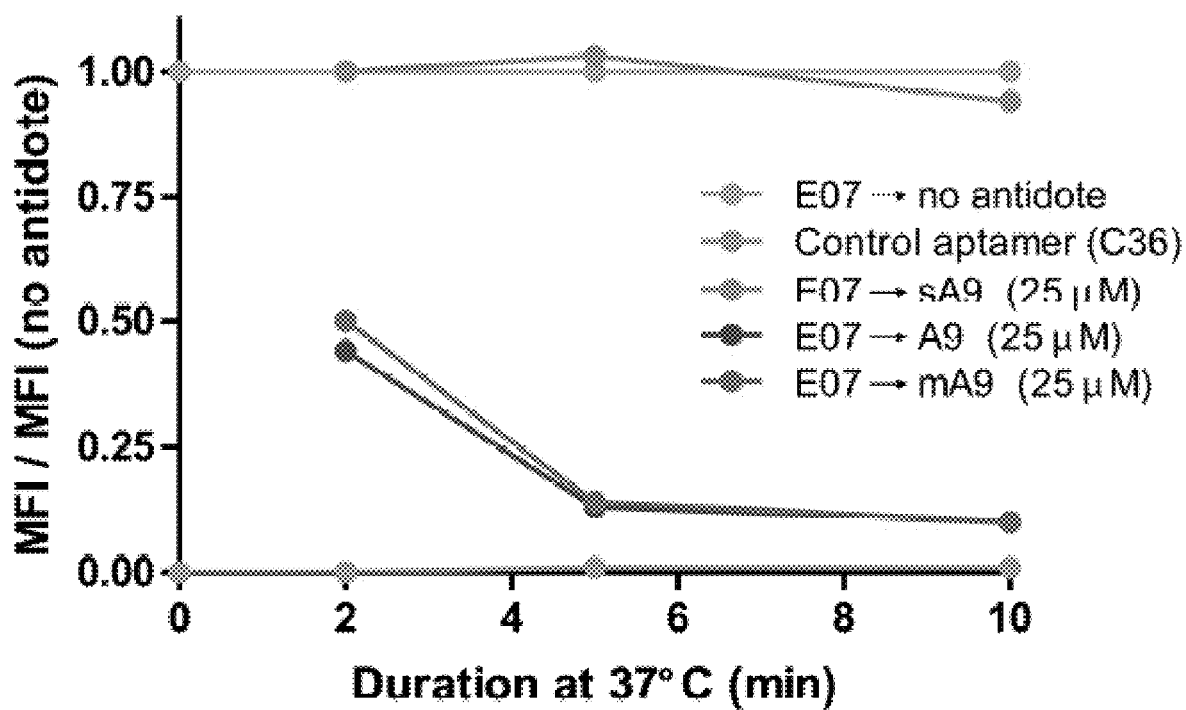
Figures 3E, 3F:
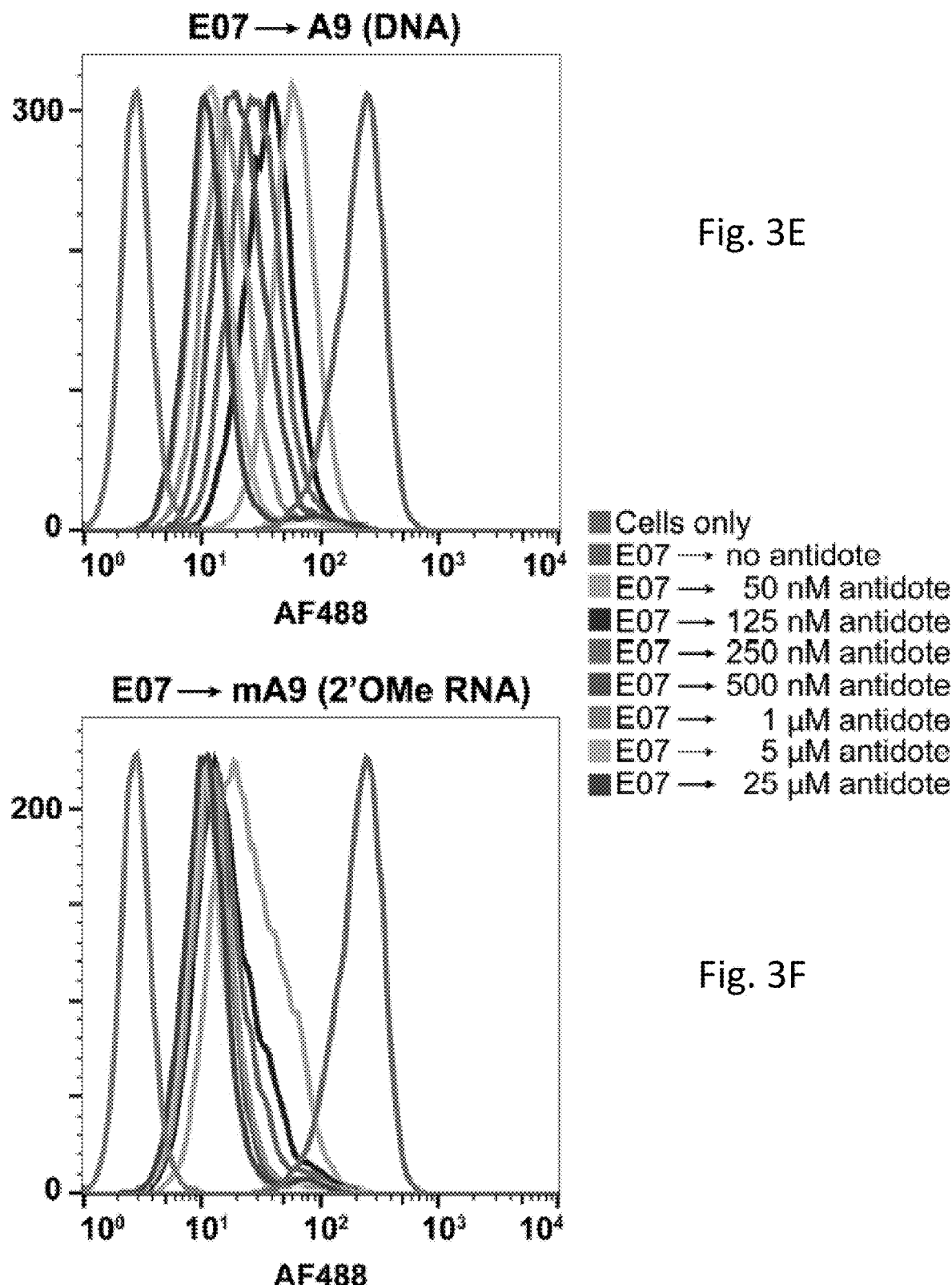
FIGS. 3E-3G show that both DNA and 2'OMe RNA antidotes were similarly effective at concentrations ≥5 µM, but the 2'OMe RNA version was more potent at lower concentrations as analyzed by flow cytometry. All flow cytometry data represent ≥$10^4$ gated events.
Figure 3G:
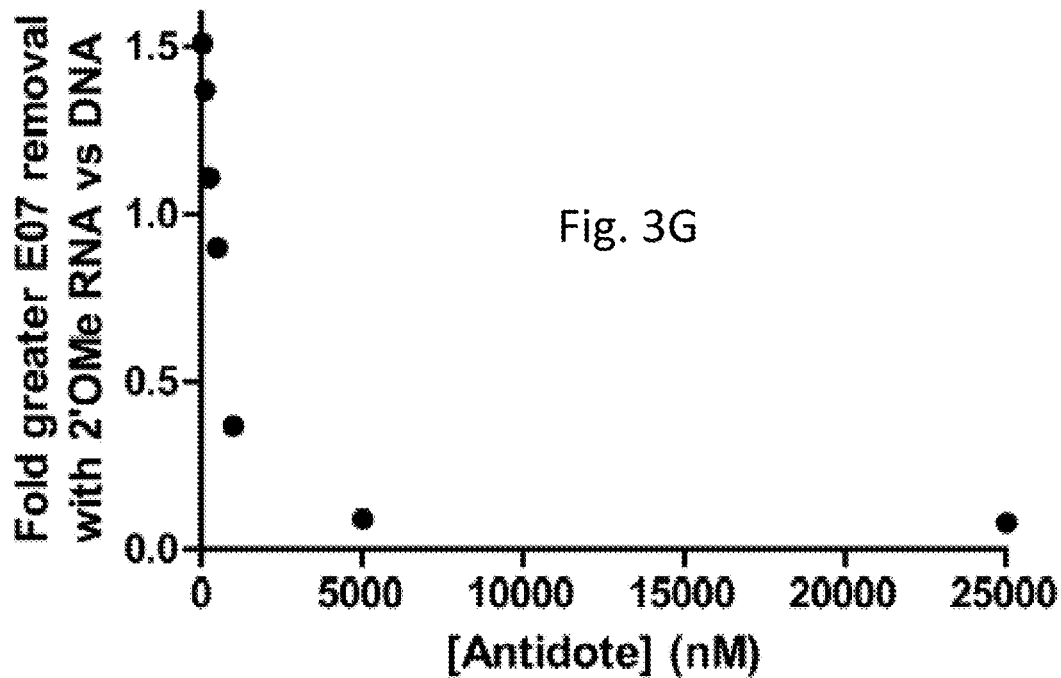

The abilities of antidote A9, its 2'O-methyl RNA analog (mA9) and a sequence-scrambled DNA-based control (sA9) to reverse E07 staining over time were then evaluated. Cells were stained with E07, washed, and then treated with a molar excess of A9, mA9 or sA9 at 37° C. for various durations before being analyzed by flow cytometry. E07-specific antidotes A9 and mA9 both stripped similar amounts of bound E07 from cells over time, reducing E07 staining to the background levels seen with a control non-targeting aptamer (C36). The scrambled control sA9 did not enhance removal of E07 relative to a no antidote treatment control (FIGS. 3B-3D). While A9 and mA9 performed similarly at the relatively high concentration of 25 mA9 was more potent at lower concentrations (<5 µM) due to the higher affinity of 2'O-methyl RNA versus DNA; consequently, mA9 was utilized in all subsequent experiments (FIGS. 3E-3G).

Multivalent E07 (E07-SA) was then substituted for monomeric E07 to provide a better comparison with antibodies, which are typically bivalent. E07-SA was formed by labeling 5'-biotinylated E07 (bE07) with AF488-labeled streptavidin (AF488-SA), creating a multivalent E07 with up to 4 aptamers per SA-dye. To limit steric effects that might impact aptamer function upon conjugation to SA, the 5' end of E07 was extended by 8 nucleotides.

Figure 4A:
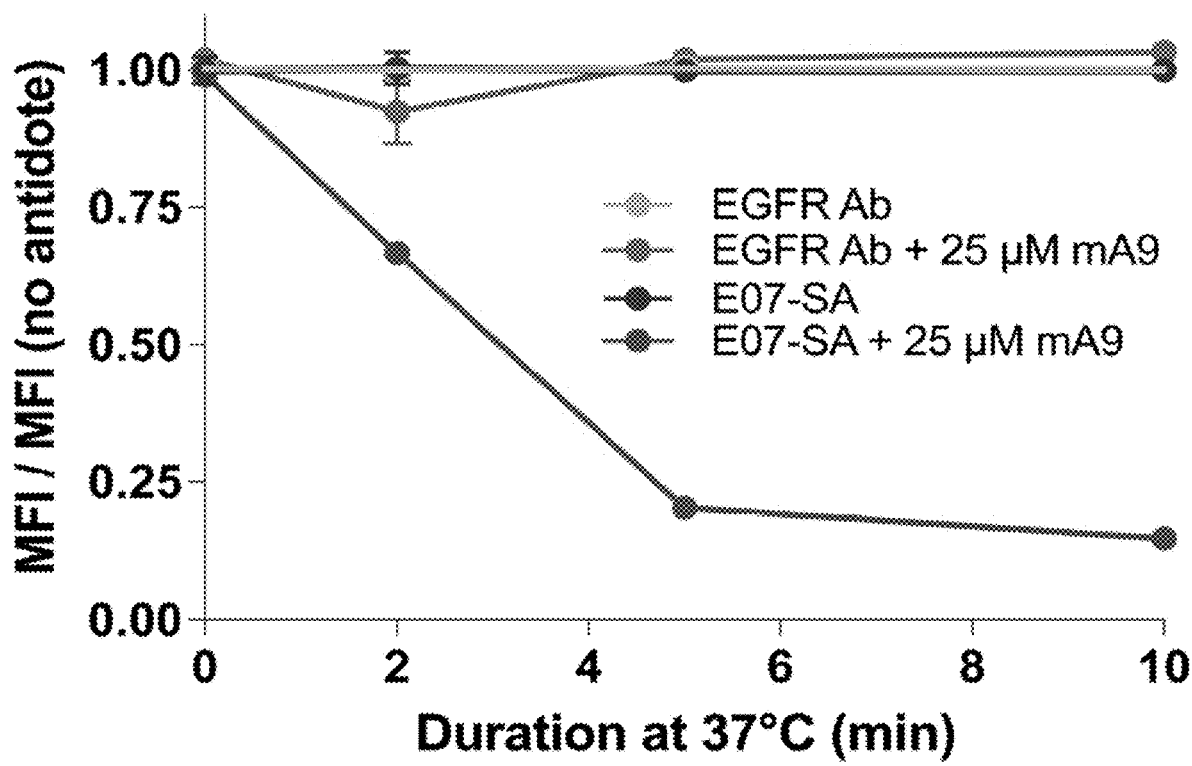
FIG. 4A shows mA9 enhanced the removal of E07-SA from cells over time but did not affect the EGFR-binding antibody ICR10 as evidenced by flow cytometry analysis of stained A431 cells (n=3). Label colors for FIG. 4A: EGFR Ab (orange), EGFR Ab+25 µM mA9 (purple), E07-SA (blue), and E07-SA+25 µM mA9 (green).
Figure 4B:
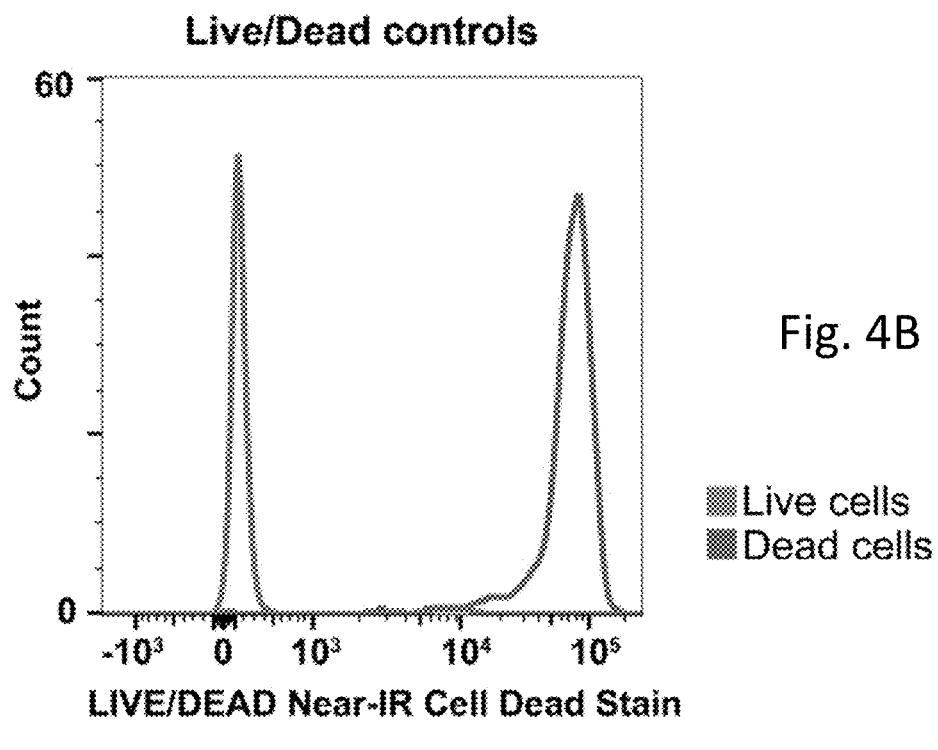
Figure 4C:
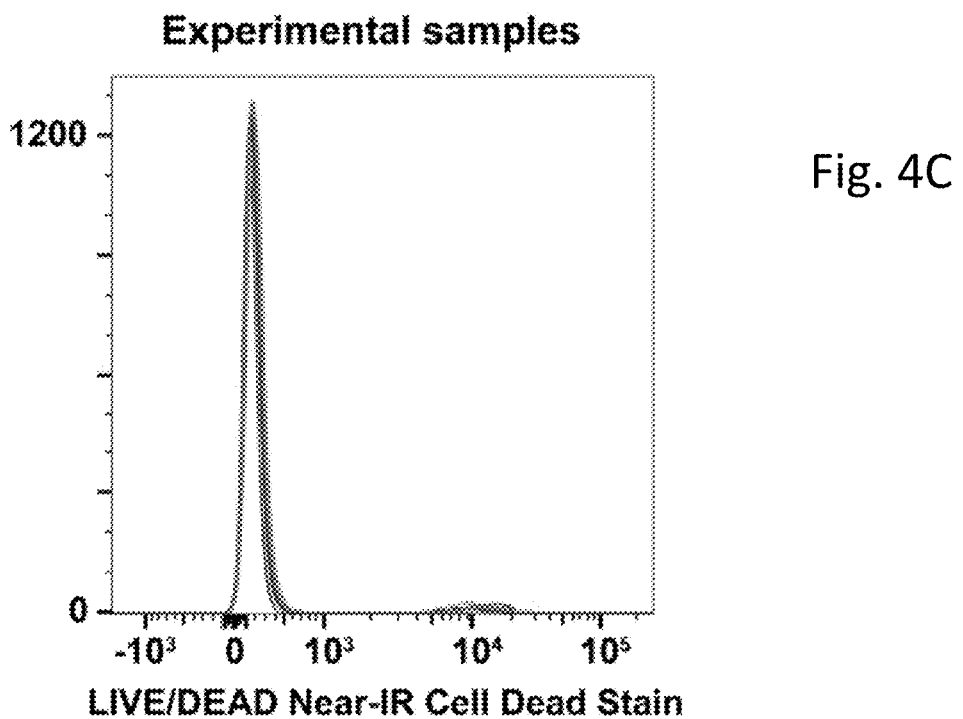
FIGS. 4C-4D shows neither E07-SA, EGFR-antagonizing antibody (D1D4J) or mA9 treatment significantly impacted viability relative to the live control (FIG. 4C), with all conditions sustaining viabilities ≥95% (n≥4) against comparison to the control (FIG. 4D). Flow cytometry data represent ≥$10^4$ gated events. Label colors for FIG. 4B: live cells (green) and dead cells (red).
Figure 4D:
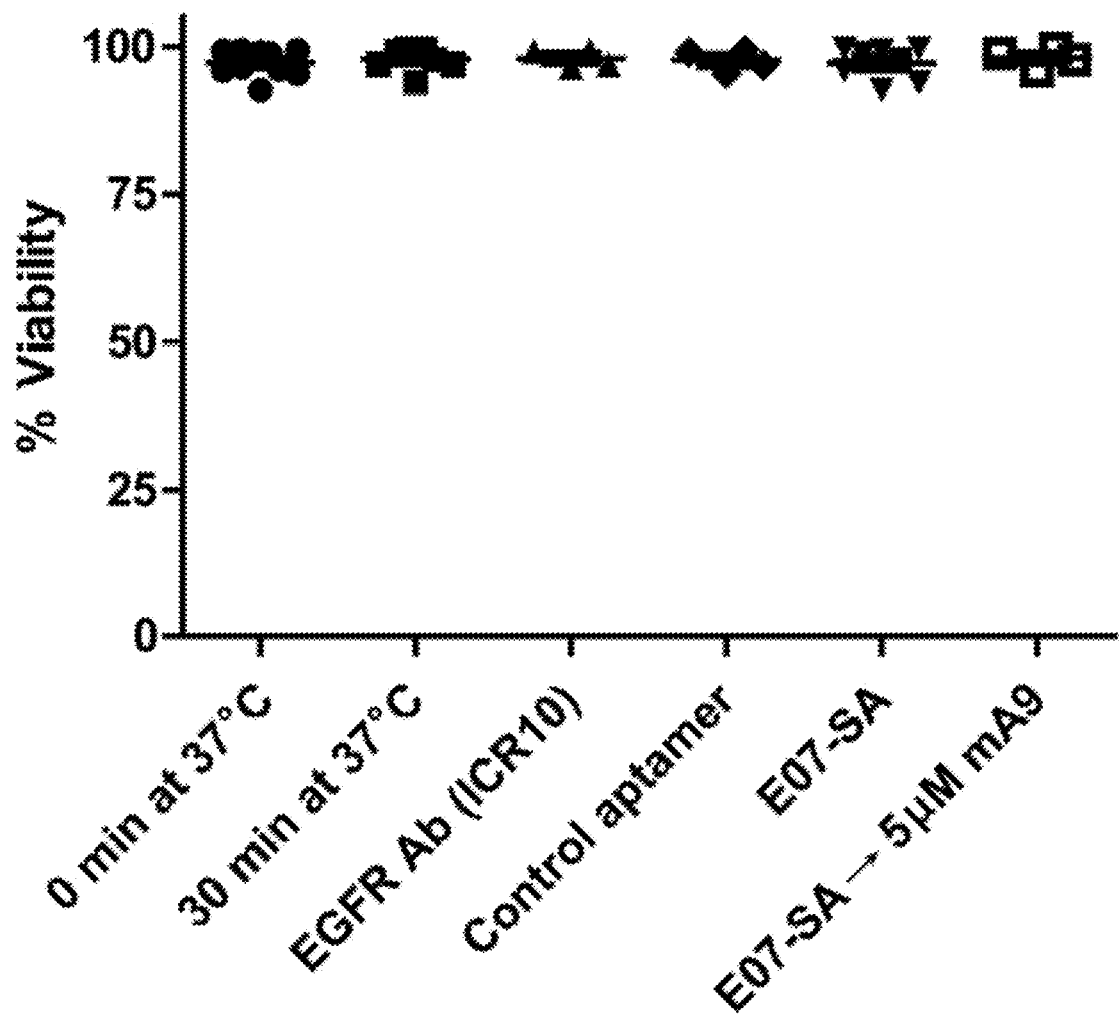
Figure 4E:
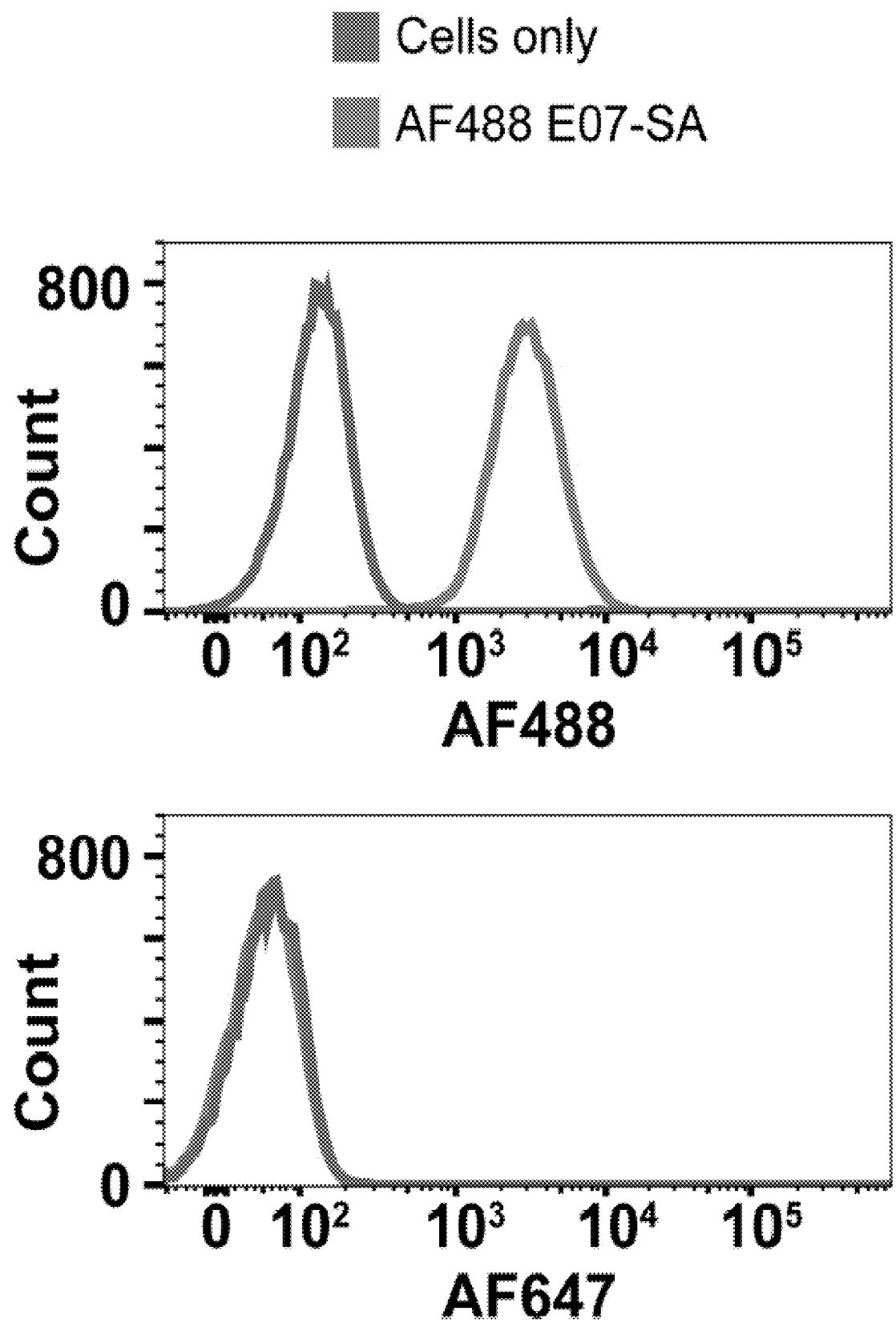
FIGS. 4E-4G shows treatment with mA9 removed E0A-SA-AF488 staining from A431 cells, enabling subsequent restaining with E07-SA-AF647 as analyzed by flow cytometry (n=3; representative curves shown).
Figure 4F:
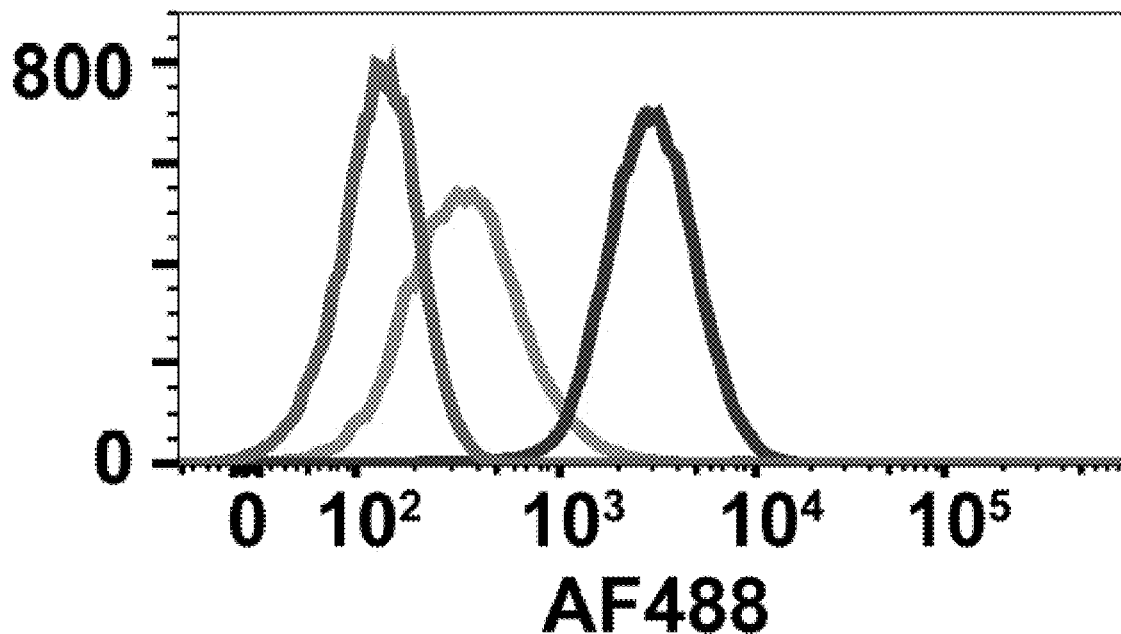
Figure 4F:
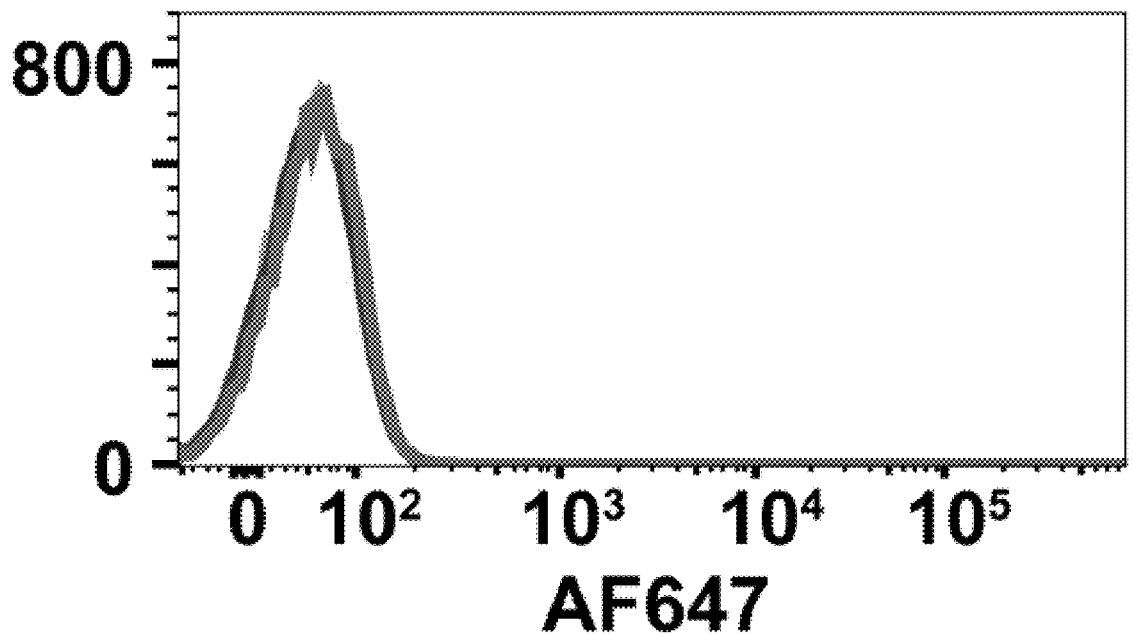
Figure 4G:
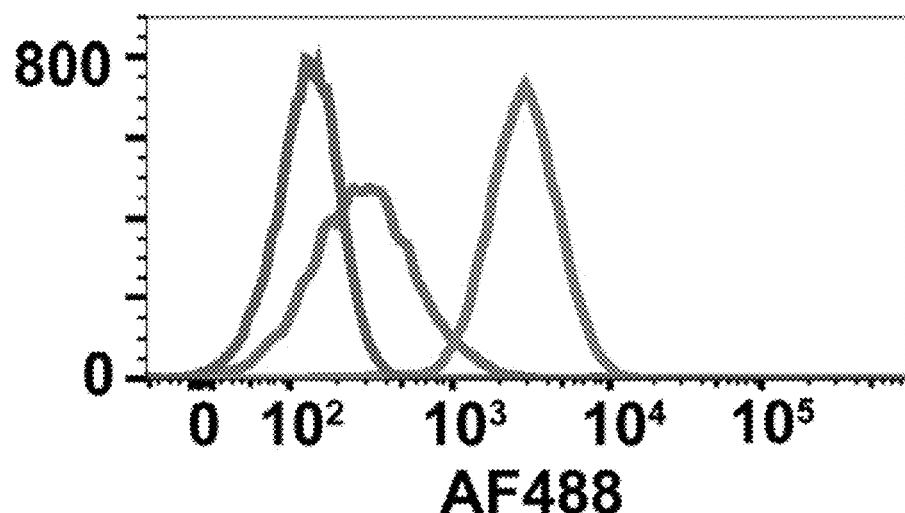
Figure 4G:
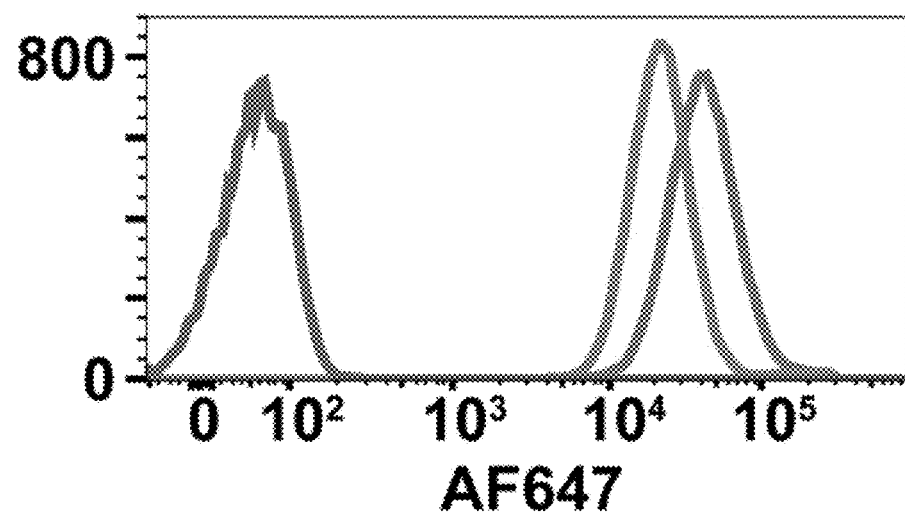

To validate E07-SA as a reversible alternative to antibodies, cells were stained with either E07-SA or an EGFR-binding antibody (ICR10) and then treated with or without mA9 to destain. E07-SA and ICR10 each exhibited robust cell-staining and stability at 37° C. in the absence of antidote. In contrast, treatment with 25 µM mA9 readily removed bound E07-SA but did not remove bound ICR10 as antibodies are not sensitive to antidote treatment (FIG. 4A). Importantly, the gentle nature of this sequential method maintained cell viability (FIGS. 4B-4D).

Successful antidote reversal of E07-SA staining restored the cells to their native state, presenting the option of restaining the cells. Such a method would allow the flexibility to serially sort a cell population for multiple biomarkers using a single fluorophore or fluorophores with overlapping spectral profiles. Additionally, a reversible cell-staining ligand could serve as a molecular switch that can be toggled on and off. To demonstrate this concept, we stained cells with E07-SA-AF488, sorted for E07/AF488+ signal and then destained with or without mA9 before restaining with E07-SA labeled with the fluorophore AF647 (E07-SA-AF647). Successful antidote reversal of the E07-SA-AF488 stain should strip E07 from EGFR on the cell surface turning the molecular switch "off" and leaving the receptor available to turn "on" again by restaining with E07-SA-AF647. E07-SA-AF488 staining did not saturate all EGFR binding sites, allowing subsequent cell staining with E07-SA-AF647 without loss of E07-SA-AF488 signal (FIGS. 4E-5G). Conversely, antidote mA9 treatment switched "off" the EGFR staining by removing ~90% of the initial aptamer AF488 stain. Subsequent labeling with E07-SA-AF647 turned back "on" the EGFR switch, staining antidote-treated cells with ~80% more AF647 compared to the control, non-antidote treated cells.

Figure 4H:
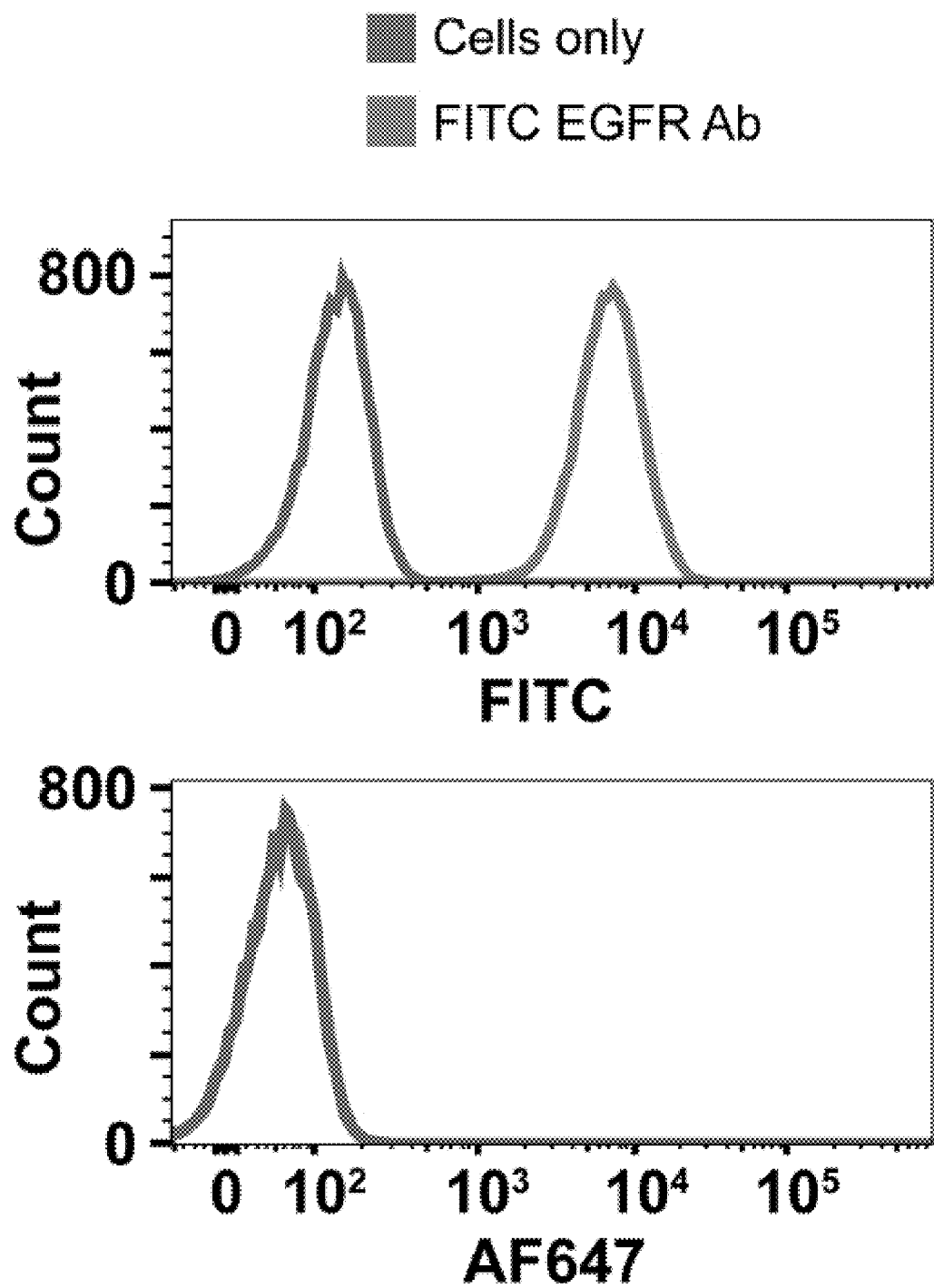
FIGS. 4H-4J shows irreversibility of antibodies prohibits their use in restaining applications as analyzed by flow cytometry (n=3; representative curves shown).
Figure 4I:
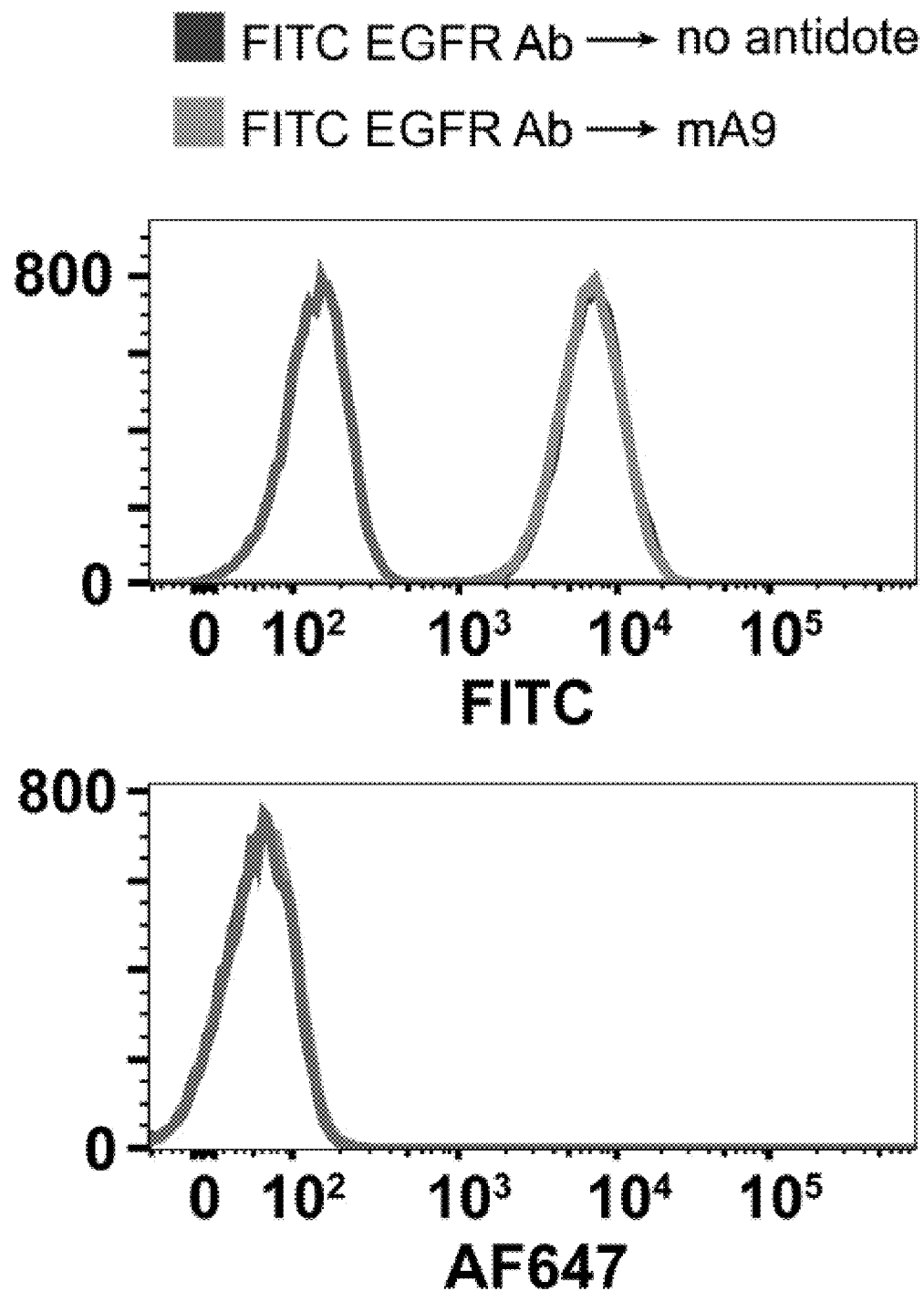
Figure 4J:
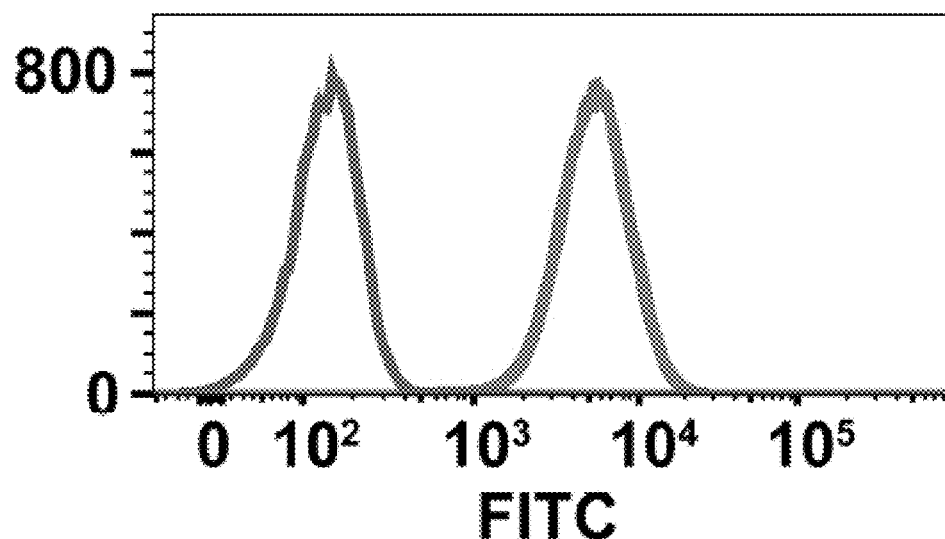
Figure 4J:
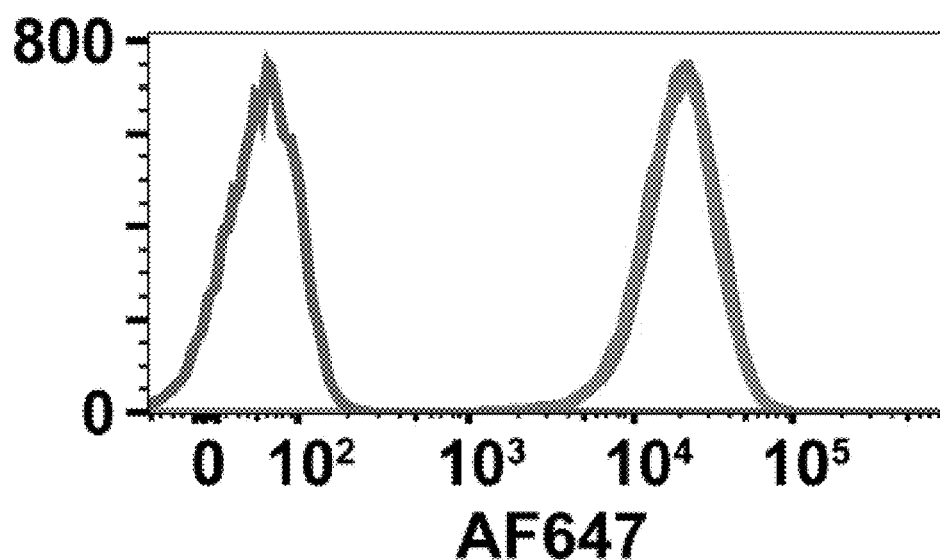

This method is not applicable to antibody labels due to their irreversibility (FIGS. 4H-4I). In contrast to aptamer-based cell labels, antibody was not removable from cells upon antidote treatment. This is shown here by the consistent fluorescence levels of a primary EGFR-binding antibody (ICR10) both prior to and after antidote mA9 treatment and by the ability of a corresponding secondary antibody to bind the EGFR antibody at the same level both before and after antidote treatment.

Figure 4K:
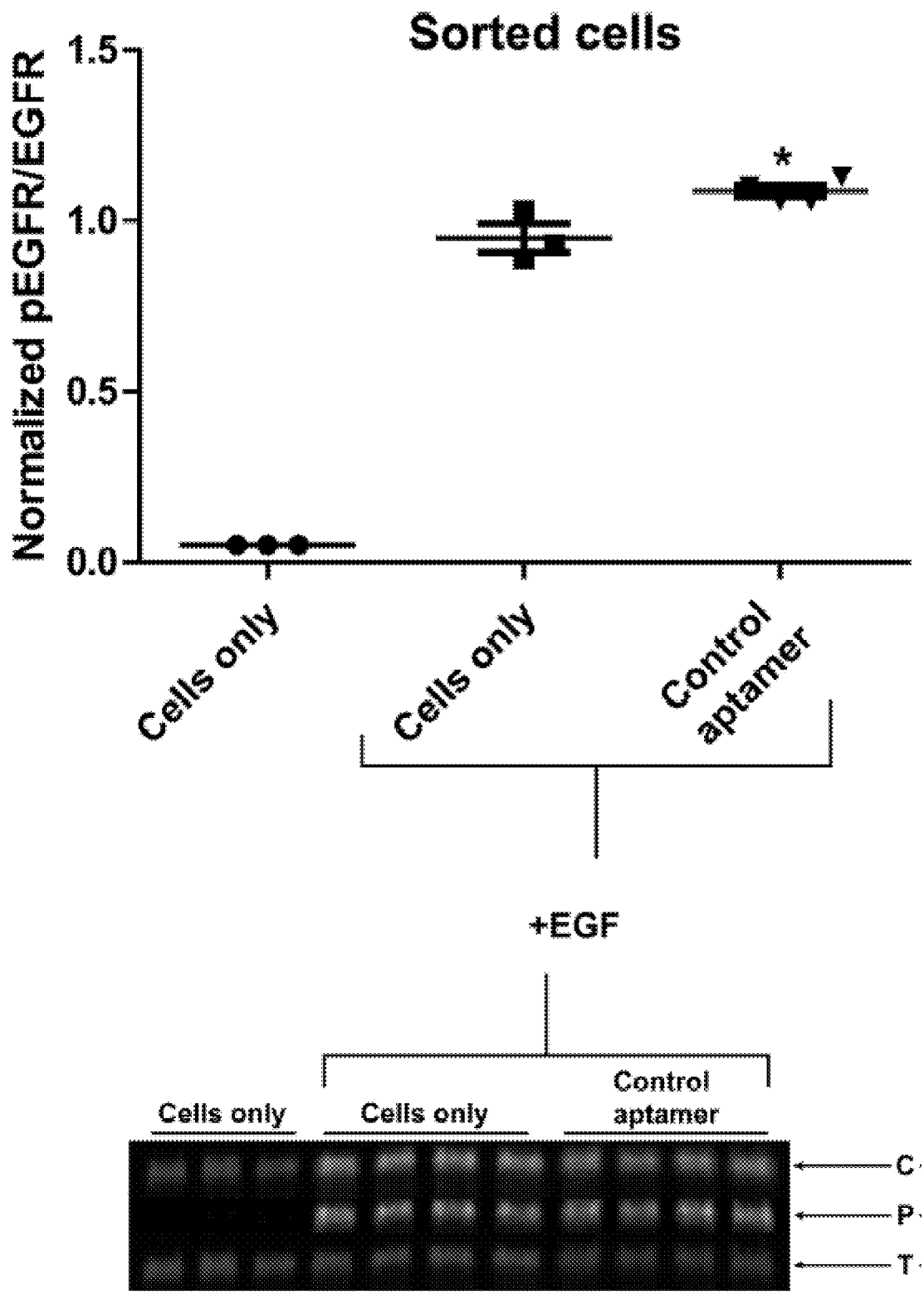
FIGS. 4K-4M show quantitative western blots of A431 cells probed for both phosphorylated EGFR (pEGFR; red; "P") and total EGFR (green; "T") after stimulation with EGF (indicated by "+EGF"). The composite overlay is labeled "C". Cells were sorted for EGFR expression after staining with either E07-SA or an EGFR-antagonizing antibody (D1D4J). While EGF stimulated EGFR phosphorylation in both unstained cells and cells stained with the control C36 aptamer (FIGS. 4K-4M), staining both unsorted (FIG. 4L) and sorted (FIG. 4M) cells with either E07-SA or an EGFR-antagonizing antibody suppressed stimulation of EGFR by EGF, indicating compromised receptor function. Subsequent treatment with 5 µM mA9 for 5 min sufficiently removed E07-SA to restore EGFR stimulation to native levels. In contrast, irreversibly bound antibody permanently inhibited stimulation of EGFR (n≥3). One-way ANOVAs followed by Tukey-Kramer post-hoc tests were used to determine significance as indicated by * (p=0.012) and **** (p<0.0001). Data are mean±SEM, and flow cytometry data represent ≥10 4 gated events.
Figure 4L:
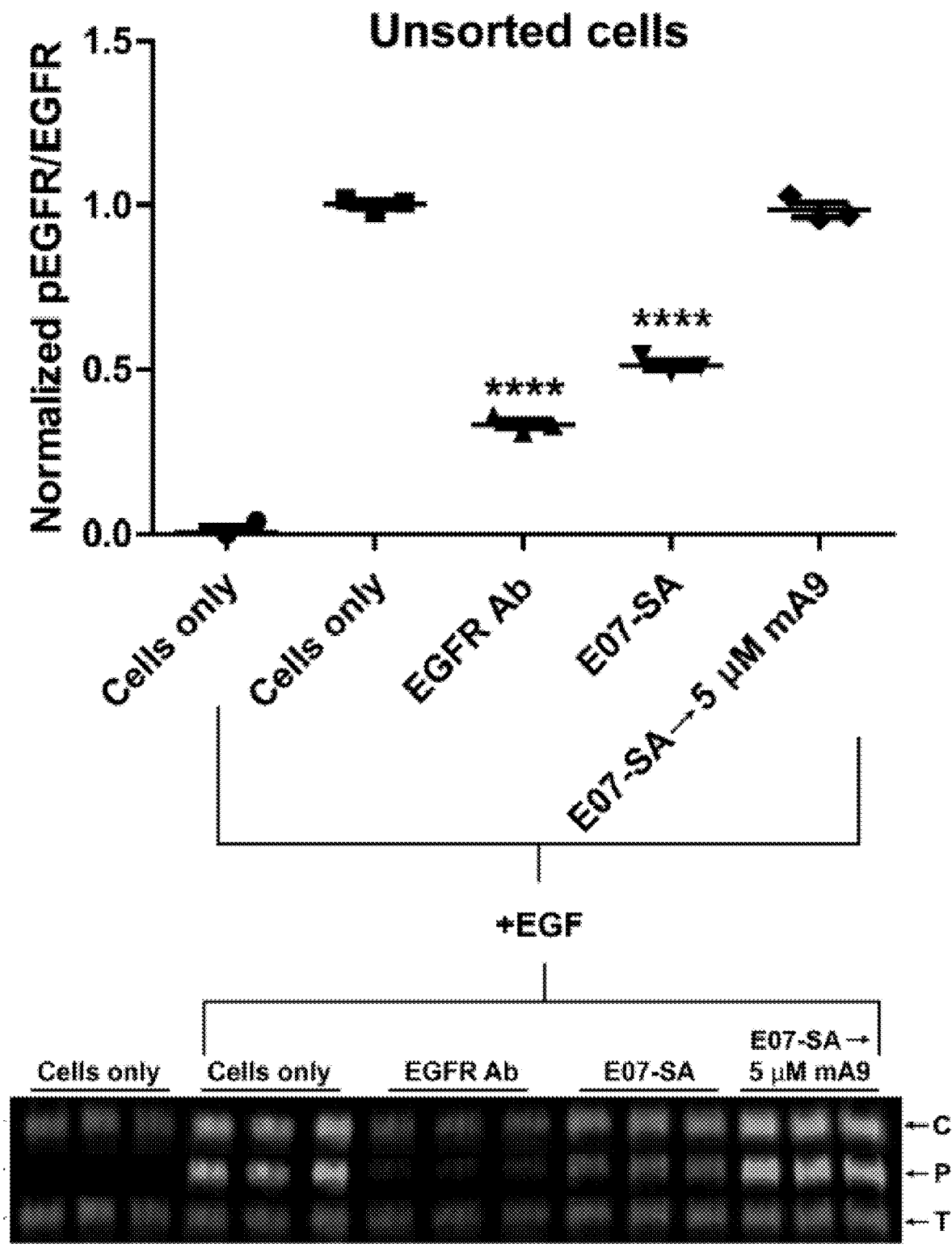
Figure 4M:
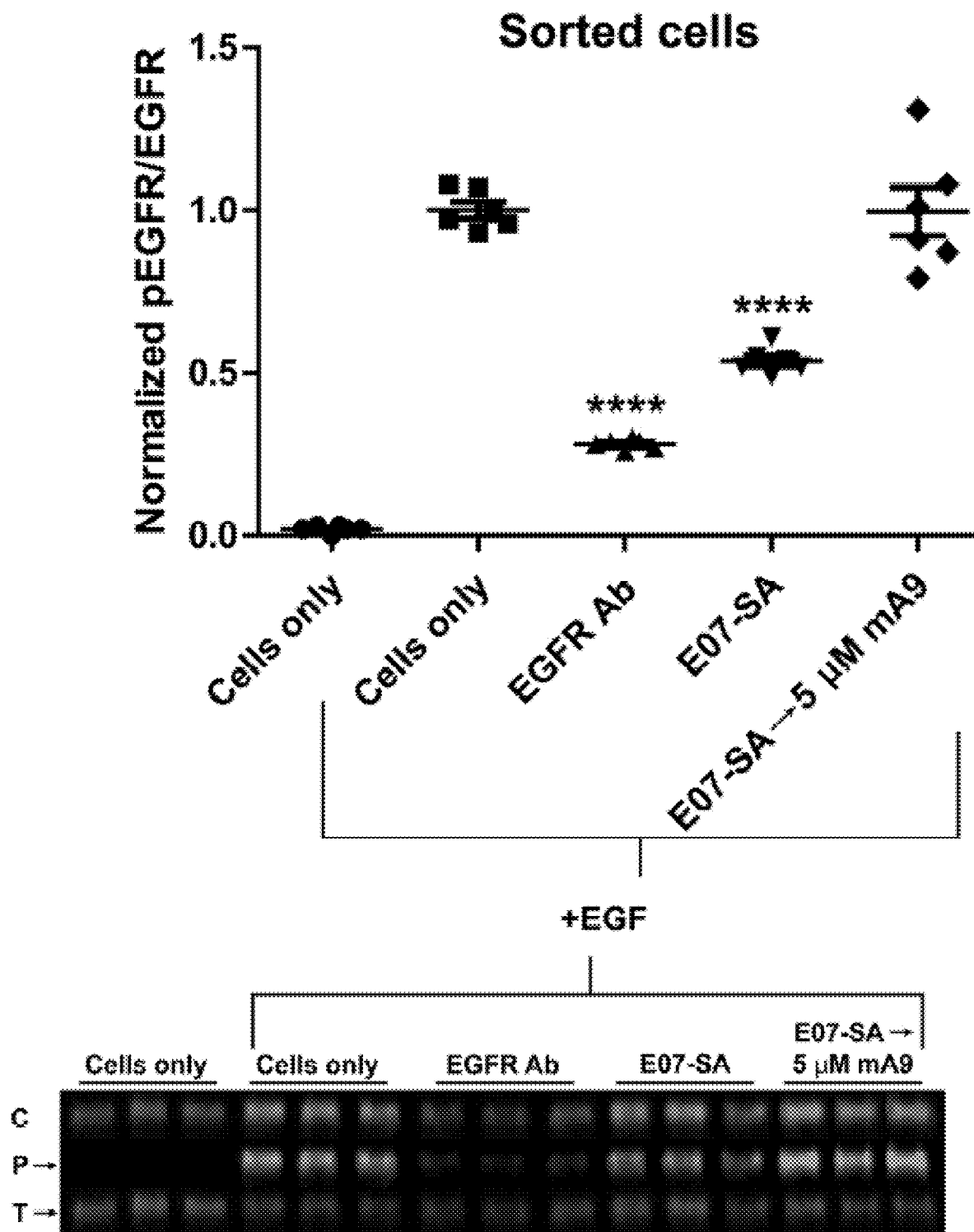
Figure 5A:
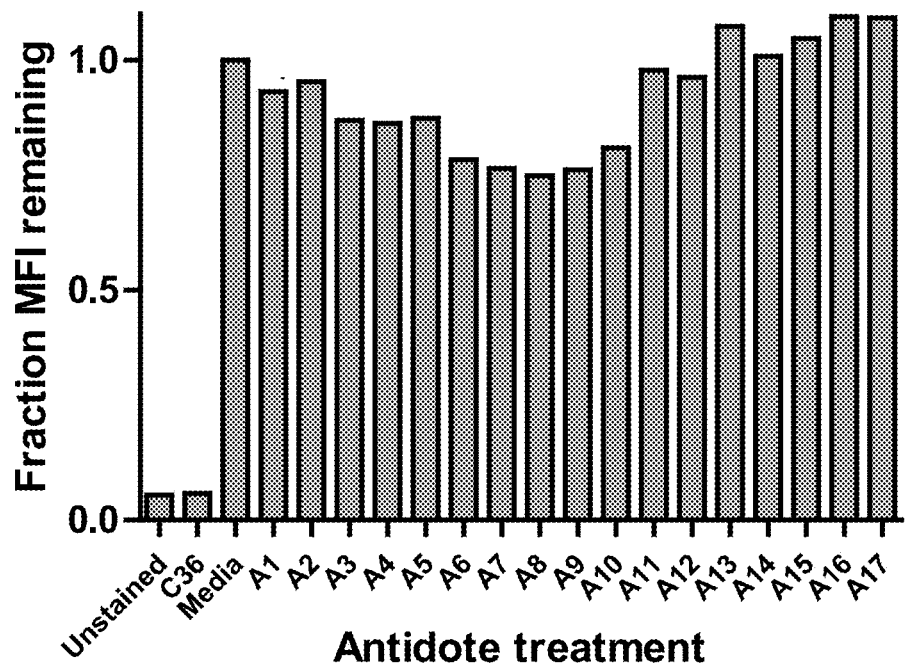
FIGS. 5A and 5B show a reduction in MFI indicated by antidote-mediated blocking of aptamer binding (FIG. 5A) or removal of bound aptamer (FIG. 5B). Staining both in the (FIG. 5A) presence and (FIG. 5B) absence of antidote at 4° C. only modestly reduced the amount of bound E07, with antidotes targeting predicted loop region being most effective.
Figure 5B:
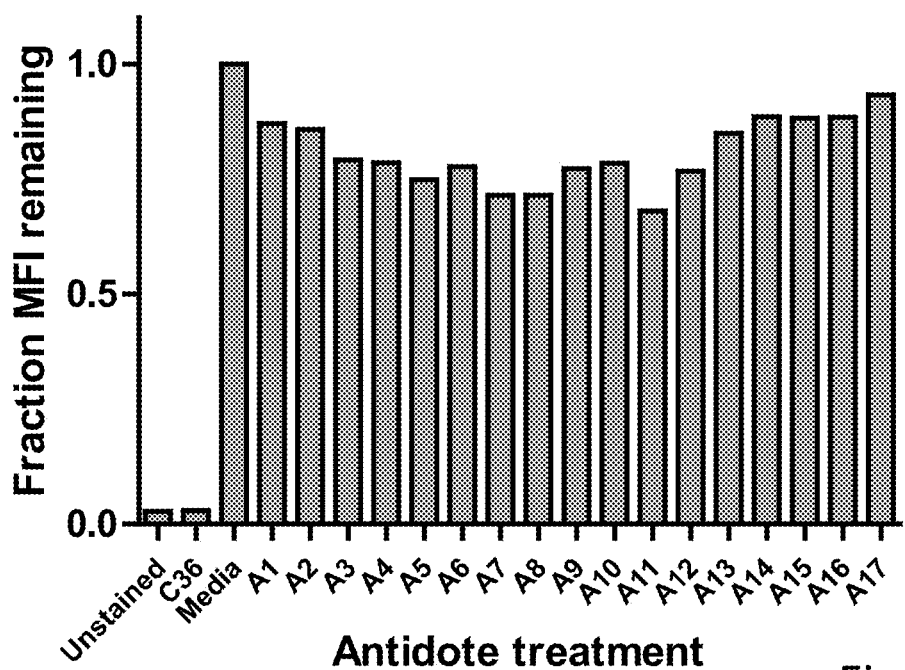

The ability of reversible cell-ligands to return cells to a native functional state was next explored by using mA9 to rescue EGFR function of cells stained with either E07-SA or with a neutralizing EGFR antibody (D1D4J). This approach was assessed by stimulating cells with EGF, a native agonist for EGFR that, upon binding, promotes phosphorylation of the receptor's intracellular domain, consequently initiating downstream signaling that modulates cellular function. E07 and D1D4J are both EGFR antagonists that block EGF-induced stimulation, reducing phosphorylation. Antidote removal of E07-SA from stained cells should thus restore EGFR phosphorylation to native levels, indicating functional recovery of cells previously crippled due to the presence of the EGFR-targeting ligand. This restoration was evaluated using quantitative western blots that probed for total and phosphorylated EGFR (pEGFR) and allowed determination of relative phosphorylation levels (pEGFR/total EGFR) of cells in different treatment groups. For unsorted and sorted samples, both E07-SA and D1D4J-stained cells exhibited significantly reduced stimulation relative to the positive control of native cells stimulated with EGF (FIGS. 4K-4M). However, treatment of E07-SA-stained cells with 5 µM mA9 rescued EGF stimulation to native levels, indicating a complete functional recovery of the targeted receptor. In contrast, D1D4J binding was irreversible and resulted in permanently crippled EGFR signaling (FIGS. 4L and 4M).

The ability to reversibly label cells without compromising their viability or function is a valuable, versatile tool with important implications for both the lab and clinic. Here, we demonstrate that multivalent aptamers can be used to sort cells in place of antibodies while also retaining the aptamer-exclusive benefit of antidote-mediated reversibility. This methodology serves as an adaptable platform for other aptamer-antidote pairs that are able to suit a myriad of research and clinical applications.

Example 2

Best Performing Antidotes Targeted Predicted Loops of E07

When performed at 4° C., staining with E07 in both the presence of antidote (FIG. 5A) and before antidote treatment (FIG. 5B) only slightly reduced the amount of bound aptamer relative to only-stained cells despite excessively high antidote concentrations (100 Even more muted effects were observed conducting these screens at lower antidote concentrations (1 and 10 µM; data not shown). Dramatically improved antidote performance was achieved at 37° C. with significantly decreased fluorescence (FIG. 3A).

A431 cells were stained for 30 min with C36 (random control RNA) or E07 in either the absence or presence of 1000-fold molar excess (100 µM) of antidote at either 4° C. or 37° C. Samples stained in the absence of antidote were subsequently washed and resuspended in antidote under the same conditions as for staining. Unstained, C36-stained and non-antidote treated E07-stained cells served as controls. Washed samples were then analyzed by flow cytometry and the fraction of the mean fluorescence intensity (MFI) relative to the non-antidote treated E07 samples were plotted. A reduction in MFI indicated antidote-mediated blocking of aptamer binding or removal of bound aptamer. Staining both in the (FIG. 5A) presence and (FIG. 5B) absence of antidote at 4° C. only modestly reduced the amount of bound E07, with antidotes targeting predicted loop region being most effective. However, staining in the presence of antidote at 37° C. (FIG. 3A) dramatically reduced the amount of bound E07 using antidotes that targeted predicted loop regions. Antidotes targeting predicted loop regions of E07 were consistently the most effective. One of the best performing antidotes across all assays, A9, was selected for use in further experiments.

Example 3

Antidote Enhanced Removal of Bound E07

Figure 6:
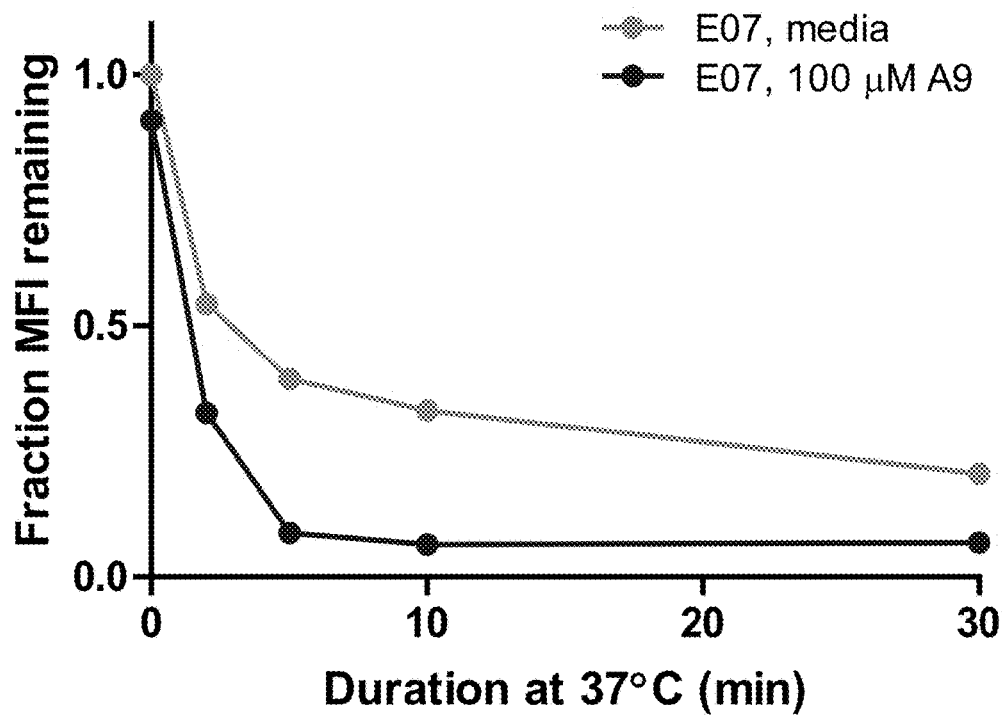
FIG. 6 shows antidote A9 enhances removal of E07 from cells only at 37° C. E07-stained A431 cells resuspended in either media (light blue) or antidote (100 µM A9) (dark blue) incubated at 37° C. removed bound E07.

E07 was relatively stable on stained cells at the temperature of 4° C. maintained during staining and sample handling, but 37° C. treatment readily liberated bound E07 as during antidote screening. Destaining cells to 21% of their initial E07-attributed fluorescent intensity over duration of 30 min was achieved with media+ alone (FIG. 6). However, the rate and degree of E07 removal was greatly enhanced in the presence of 100 µM A9. This concentration of A9 enabled maximal destaining (6.8% of initial value) by 10 min. These results are representative of several other destaining experiments performed with similarly high antidote levels. The originally selected, full-length E07 aptamer (93 bases) was observed to be lost at the same rate in media+ only, indicating that the instability of E07 was not conferred by truncation (data not shown).

Example 4

Formation of Higher Valency Conjugates was Favored by Increased Aptamer to SA Ratios Multivalent aptamer-SA conjugates were formed by reacting E07 and C36 possessing 5' biotinylated tails (bE07 and bC36) with AF488-labeled tetrameric SA. EMSAs revealed that higher aptamer:SA molar ratios resulted in a larger proportion of higher molecular weight conjugates (FIGS. 7A-7D). This presumably corresponded to higher valency conjugates via greater saturation of the four SA sites available for binding.

Figure 7A:
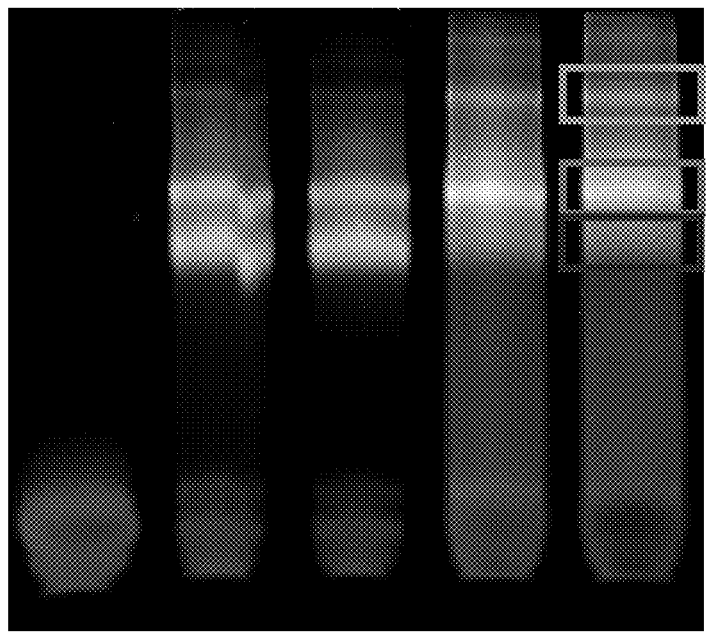
FIGS. 7A-7D show higher valency aptamer-streptavidin conjugates were generated using higher molar ratios of aptamer to streptavidin. bE07 (FIG. 7A) and bC36 (FIG. 7B) RNA was then visualized by staining gels with SYBR Gold followed by imaging. The smallest (blue), middle (green), and largest (orange) MW conjugates were respectfully assumed to be monovalent, bivalent and trivalent.
Figure 7B:
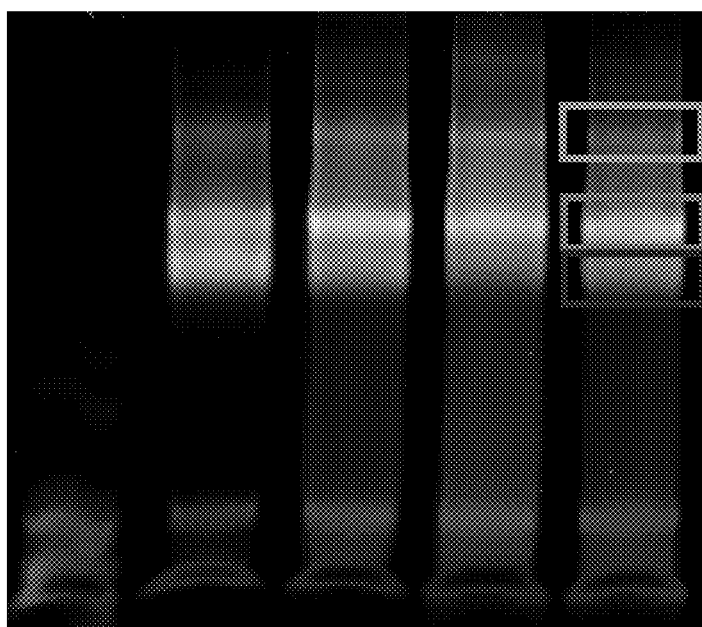
Figure 7C:
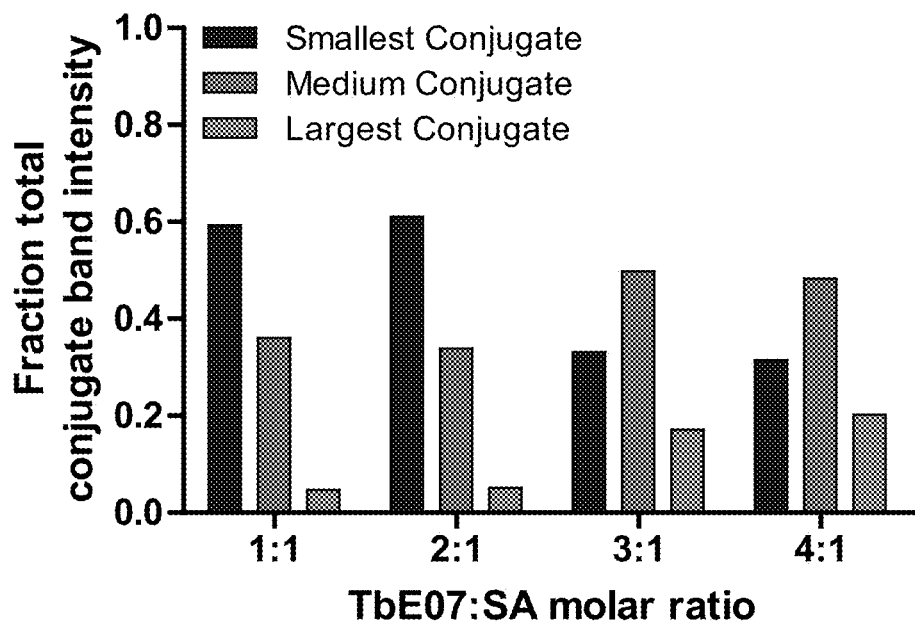
Figure 7D:
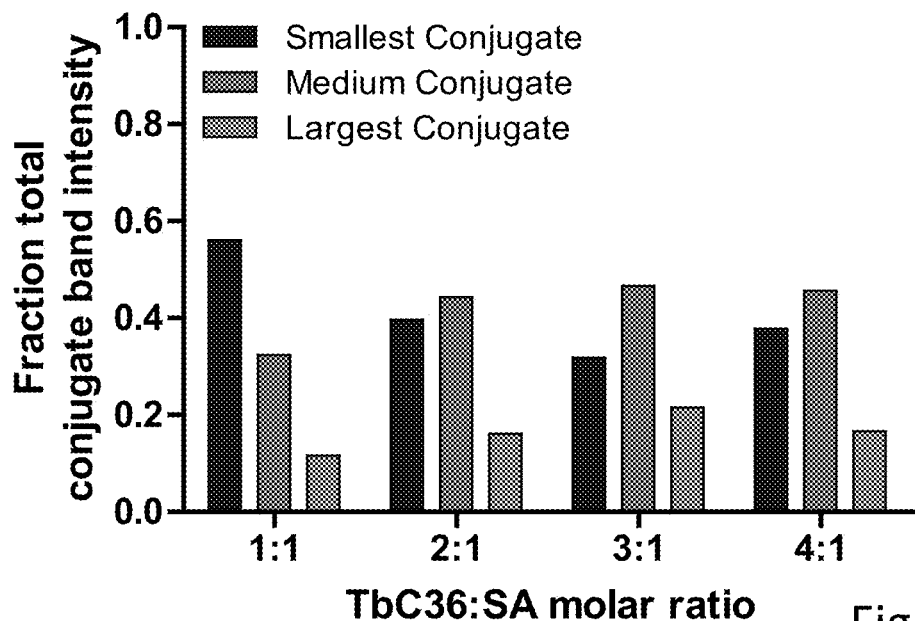

The valency of aptamer-streptavidin (SA) conjugates prepared with different molar ratios of biotinylated aptamer to SA was characterized by electrophoretic mobility shift assays (EMSAs). C36 or E07 with 5' biotinylated tails (bC36 and bE07) were reacted with tetrameric SA with four biotin binding sites in 1:1, 2:1, 3:1 or 4:1 molar ratios of aptamer to tetramer. Free RNA (1:0) and conjugate samples containing equal amounts of SA were then separated by electrophoresis on polyacrylamide gels that denatured the RNA but preserved integrity of the SA tetramers.

bE07-SA samples prepared from 1:1 and 2:1 bE07:SA were virtually the same, with more monovalent than bivalent conjugate and very little trivalent conjugate. Higher ratio bE07-SA samples of 3:1 and 4:1 were also similar, with each having less monovalent conjugate and more bivalent and trivalent conjugates than the lower ratio preparations. bC36-SA samples exhibited a similar trend, although the yield of higher valency conjugates was better at lower ratios and less dramatic at higher ratios of biotinylated aptamer. Smallest, medium and largest conjugates were respectively thought to be monovalent, bivalent and trivalent. E07-SA conjugate mixtures prepared from 1:1 and 2:1 bE07:SA were virtually identical, consisting of ~60% monovalent and ~35% bivalent conjugate (FIG. 7C). Ratios of 3:1 and 4:1 bE07: SA yielded a greater proportion of higher valency multimers, with both reaction mixtures composed of ~32% monovalent, ~49% bivalent and ~18% trivalent conjugates. bC36-SA conjugates paralleled this pattern, but a better yield of higher valency conjugates was obtained at lower ratios (FIG. 7D). Note that all conjugate mixtures also contained unincorporated monomeric tailed aptamer. Subsequent destaining and EGF stimulation experiments utilized unpurified 2:1 aptamer:SA conjugate mixtures for comparison with E07 monomer.

Example 5

Higher Ratio E07:SA Conjugate Mixtures Exhibited Higher Apparent Affinities

Figure 8:
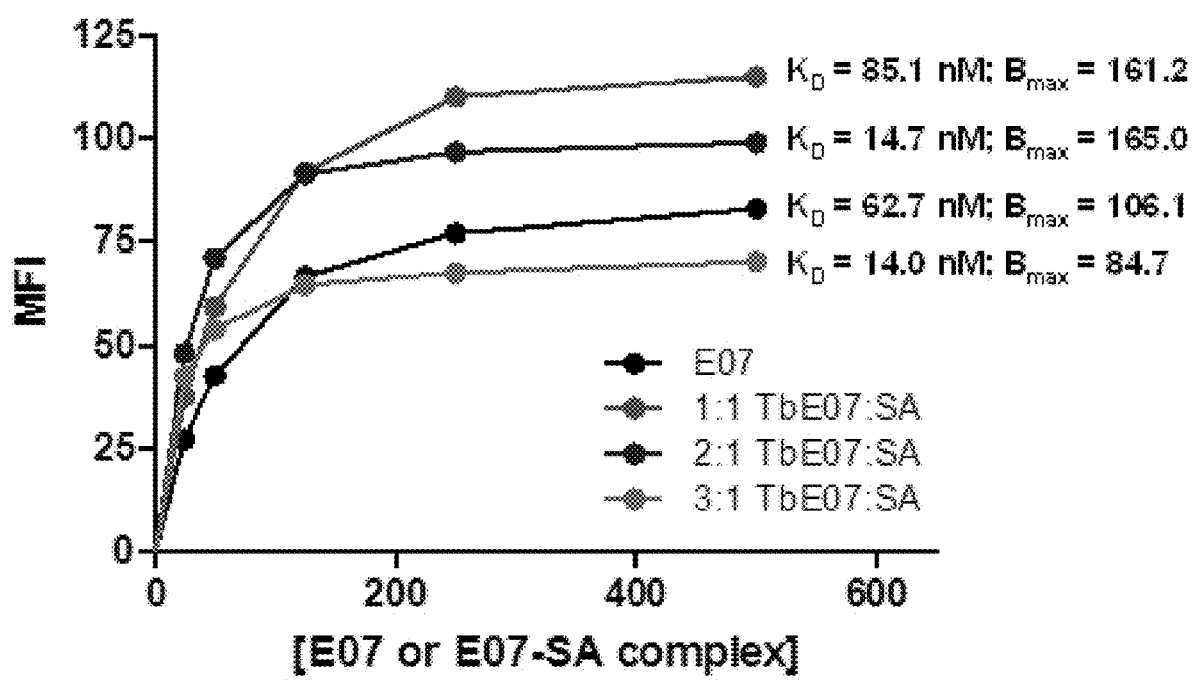
FIG. 8 shows higher ratio E07:SA conjugate mixtures possessed higher apparent affinities but lower apparent saturation. Label colors for FIG. 8: E07 (black), 1:1 TbE07:SA (purple), 2:1 TbE07:SA (blue), and 3:1 TbE07:SA (green).

Apparent affinities of E07-SA conjugate mixtures increased with higher ratios of bE07: SA, but increased affinity was accompanied by a concomitant decrease in apparent saturation (FIG. 8). For comparison, the apparent affinity of E07 (directly labeled monomer; 62.7 nM) was closer to that of the 1:1 conjugate mixture (85.1 nM) than the 2:1 mixture (14.7 nM).

A431 cells were stained with various concentrations (25, 50, 125, 250 or 500 nM) of E07 only or E07-SA conjugate mixtures prepared by reacting 1:1, 2:1 or 3:1 biotinylated E07 with tetrameric streptavidin. Stained cells were washed, analyzed by flow cytometry and their fluorescence corresponding to the amount of bound E07 or E07-SA was plotted to determine apparent binding affinities (dissociation constants; $K_D$) and cell surface saturation (total number of receptors; Bmax). Conjugate mixtures prepared from higher E07:SA ratios had higher apparent affinities, but lower apparent saturation. Unconjugated E07 had a higher affinity than the 1:1 conjugate mixture but lower affinity than the 2:1 and 3:1 mixtures.

Example 6

E07-SA Conjugate Mixtures were More Stable than E07 During Sorting and Destaining The use of E07 and E07-SA conjugate mixtures as reversible stains for cell sorting was validated and compared to different EGFR-binding monoclonal antibodies (ICR10 and D1D4J). All stain types yielded stable fluorescent cell populations distinct from unstained cells using a chiller to maintain samples being sorted at 4° C. Fluorescence of samples being sorted was compared at the beginning and end of each sort, and no drift was detected for any stain type (data not shown).

Figure 9:
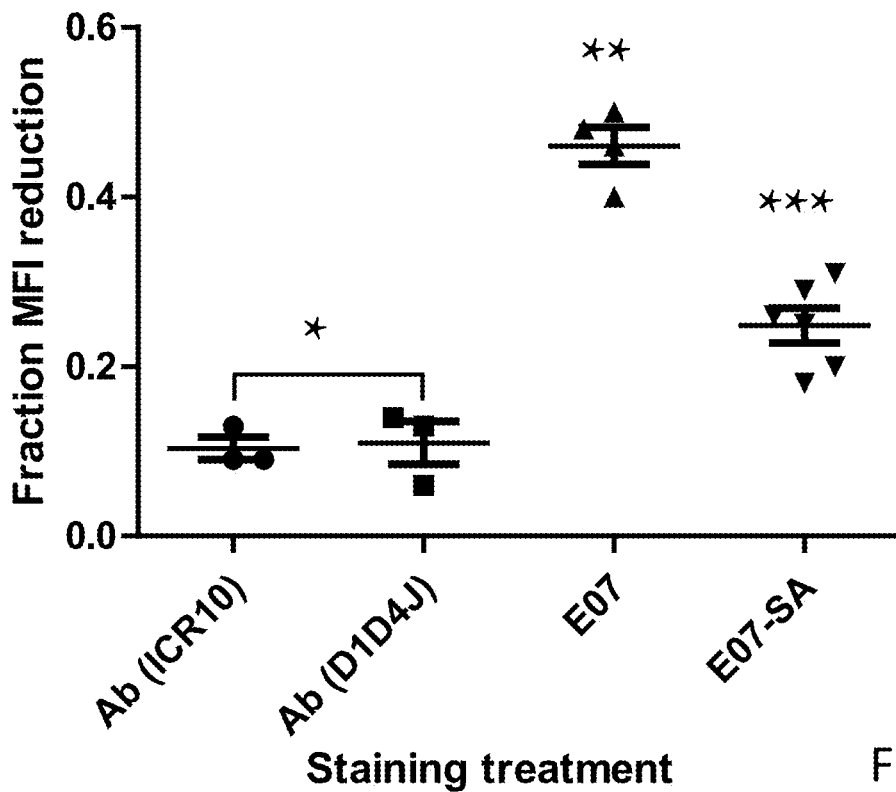
FIG. 9 shows significantly more monomeric E07 than E07-SA conjugate mixture was lost during sorting as analyzed by flow cytometry. Each group is significantly different from all others ($p<0.0001$ for *,  and *)

However, losses did occur during sorting despite actively chilling initially cold sample collection tubes (FIG. 9). Stained A431 cells were analyzed by flow cytometry immediately before and after FACS to examine losses that occurred while sorting. E07 was the least stable with losses of 46%, followed by E07-SA (2:1 E07:SA conjugate mix) with 25% losses and EGFR antibodies with about 11% losses each. Losses attributed to sorting were determined using flow cytometry to analyze samples immediately before and after FACS. E07 losses (46%) were nearly double those of the E07-SA conjugate mixture (25%), while both antibodies were more than twice as stable as the conjugate at ~11% losses each.

Example 7

Destaining Rescued Native Stimulability Of Aptamer-Stained Cells

Figure 10A:
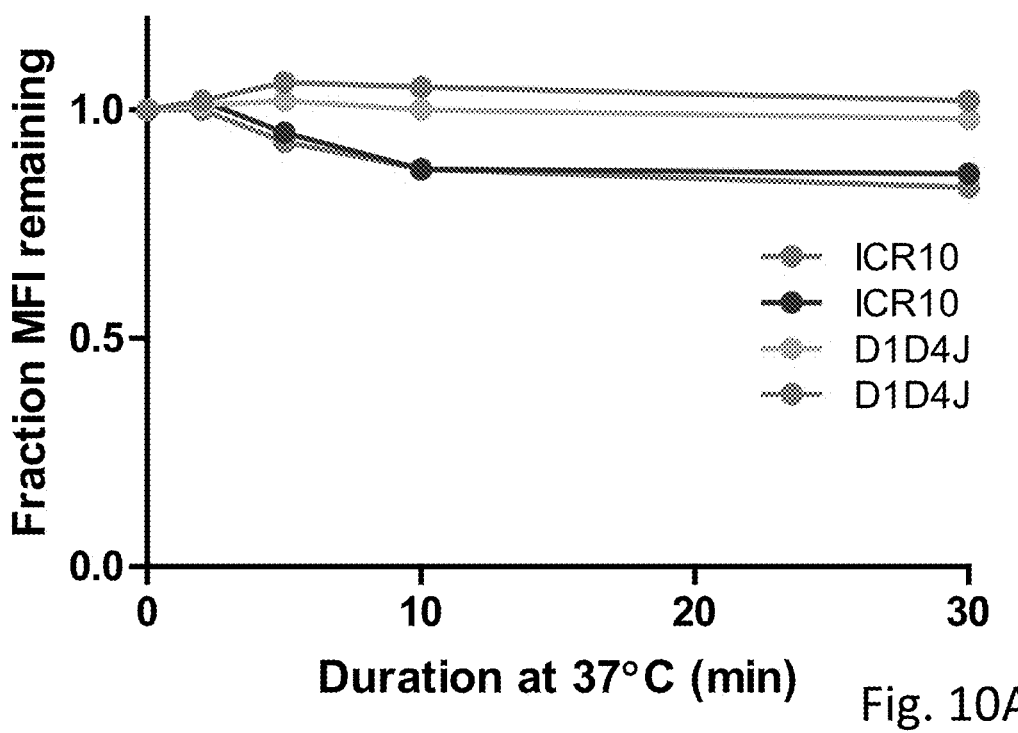
FIGS. 10A-10C show destaining sorted cells highlighted additional stability of E07-SA conjugate over E07 monomer. Cells were then analyzed by flow cytometry and reduction in fluorescence of each stain type corresponding to its removal was plotted. EGFR antibodies ICR10 (light and dark purple) and D1D4J (light and dark orange) were the most stable stains, experiencing only slight losses over 30 min at 37° C. in media (FIG. 10A). E07-SA was substantially more stable than E07 both in media only and in antidote, but higher concentration of antidote (5 µM.
Figure 10B:
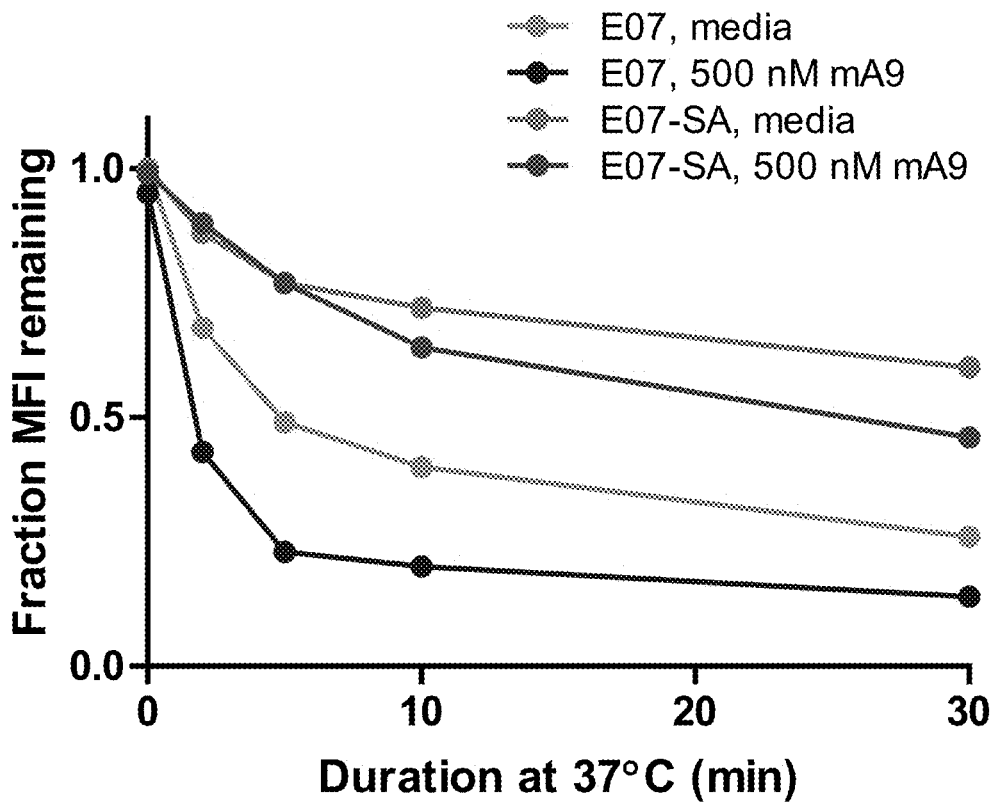
Figure 10C:
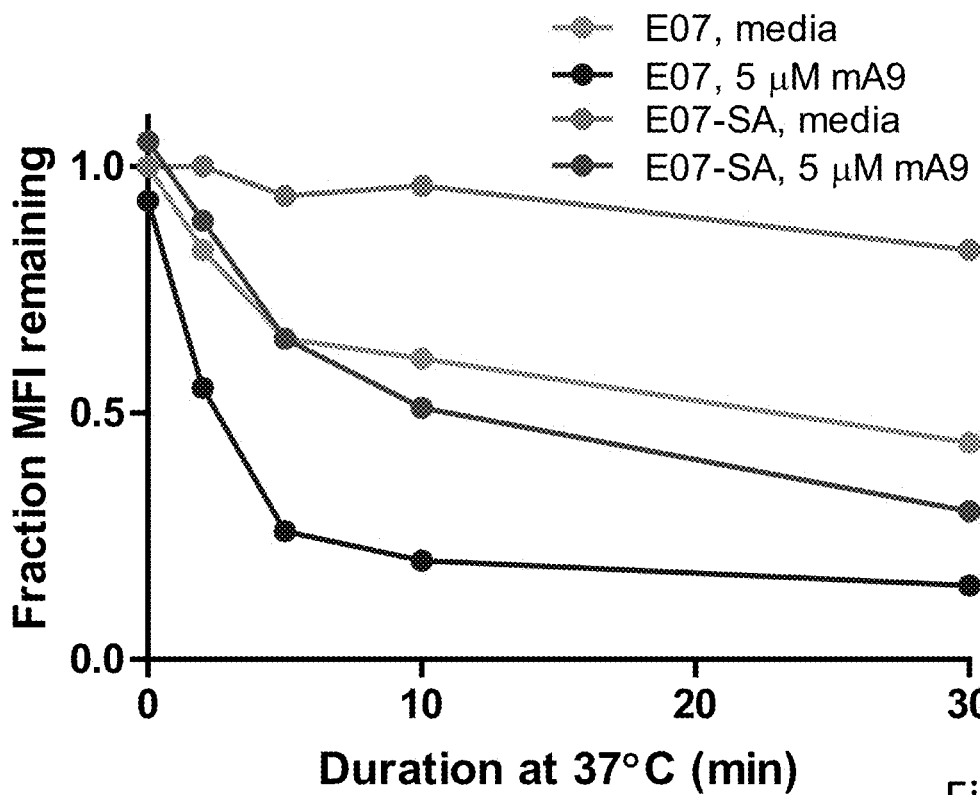

Destaining treatment successfully reversed aptamer-induced inhibition of EGFR stimulation, while antibody-induced inhibition was irreversible. EGF binding to EGFR results in phosphorylation of its intracellular domain to generate pEGFR, and this stimulation event nucleates a series of downstream signals that modulate cellular function. The degree of stimulation caused by EGF was assessed by determining the relative phosphorylation levels (pEGFR/total EGFR) of cells in different treatment Sorted cells were then destained in media+ or antidote mA9 to further assess stability and reversibility (FIGS. 10A-10C). Antibody stains remained highly stable and seemingly irreversible as cells labeled with ICR10 or D1D4J exhibited minimal losses during destaining in media+ (FIG. 10A). E07-SA conjugate mixture was markedly more stable during destaining in both media+ and 500 nM mA9 than E07 monomer (FIGS. 10B-10C). A higher mA9 concentration of 5 μM bridged the gap in removal of E07 and E07-SA conjugate mixture, with only a small fraction of each remaining after destaining for 30 min (FIG. 10C). Overall, these data mirror and corroborate the stability data derived from sorting-attributed stain losses.

Example 8

Figure 11A:
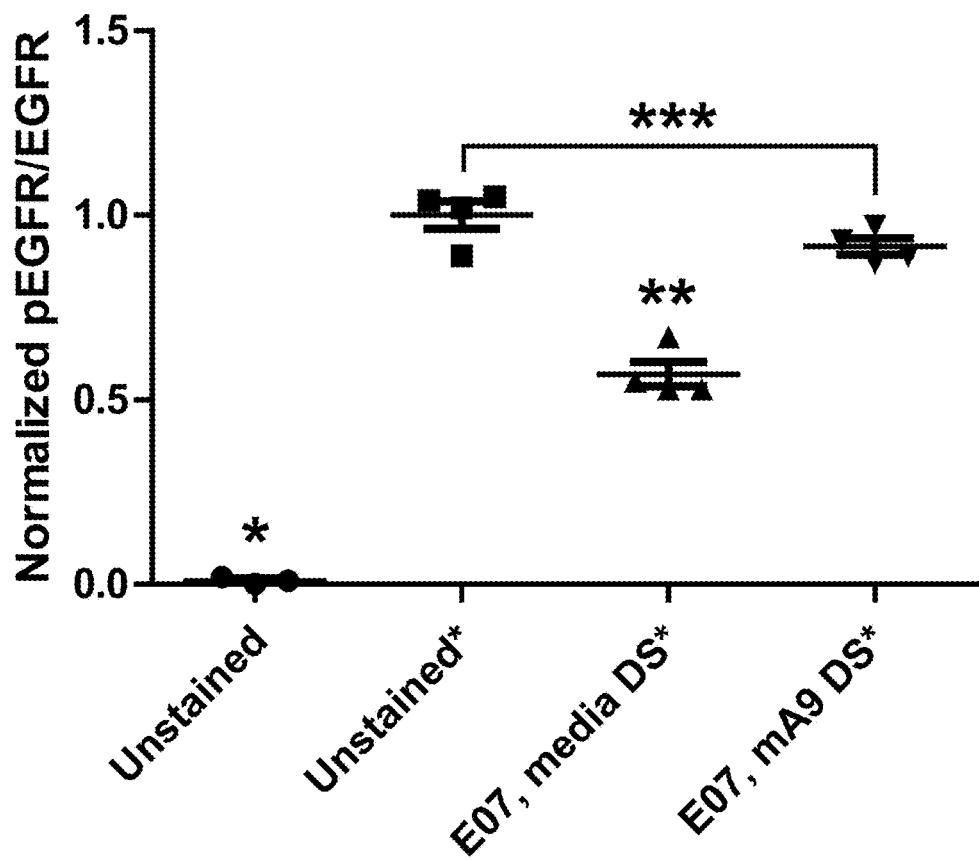
FIG. 11A shows only destaining with antidote restored ability of unsorted aptamer-stained cells to be stimulated with EGF. Quantitative Western blotting enabled quantification of EGF-induced stimulation of A431 cells via probing for phosphorylated (pEGFR; red) and total EGFR (green). * denotes stimulation with EGF; media DS=destained with media only; mA9 DS=destained with 5 µM mA9. Antibody and unstained cells were destained with media only. The degree of stimulation was taken as the ratio of the band intensities of pEGFR and total EGFR, as EGF binding triggers autophosphorylation of EGFR to generate pEGFR.
Figure 11A:
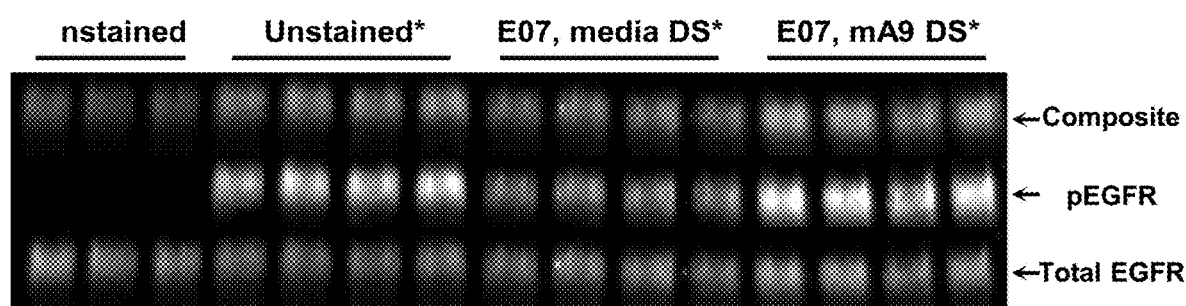

Quantitative Western Blotting Probing for Total EGFR and pEGFR was Used to Evaluate Protein Levels Stimulation of unsorted cells is shown in FIGS. 4L and 11A. EGF stimulation of cells stained with E07 (FIG. 11A), E07-SA conjugate mix or neutralizing antibody D1D4J (FIG. 4L) and destained in media+ for 5 min was significantly reduced compared to an unstained control. Destaining instead with 5 μM mA9 sufficiently removed EGFR-blocking aptamer to restore stimulation to the level of unstained cells. Notably, a two-hour incubation on ice after destaining in media+ only also rescued stimulability of cells stained with E07 but not E07-SA conjugate mixture, additionally implicating reduced stability of the monomer relative to the conjugate mixture (data not shown). In contrast, antibody binding and thus compromised EGFR function was irreversible.

Figure 11B:
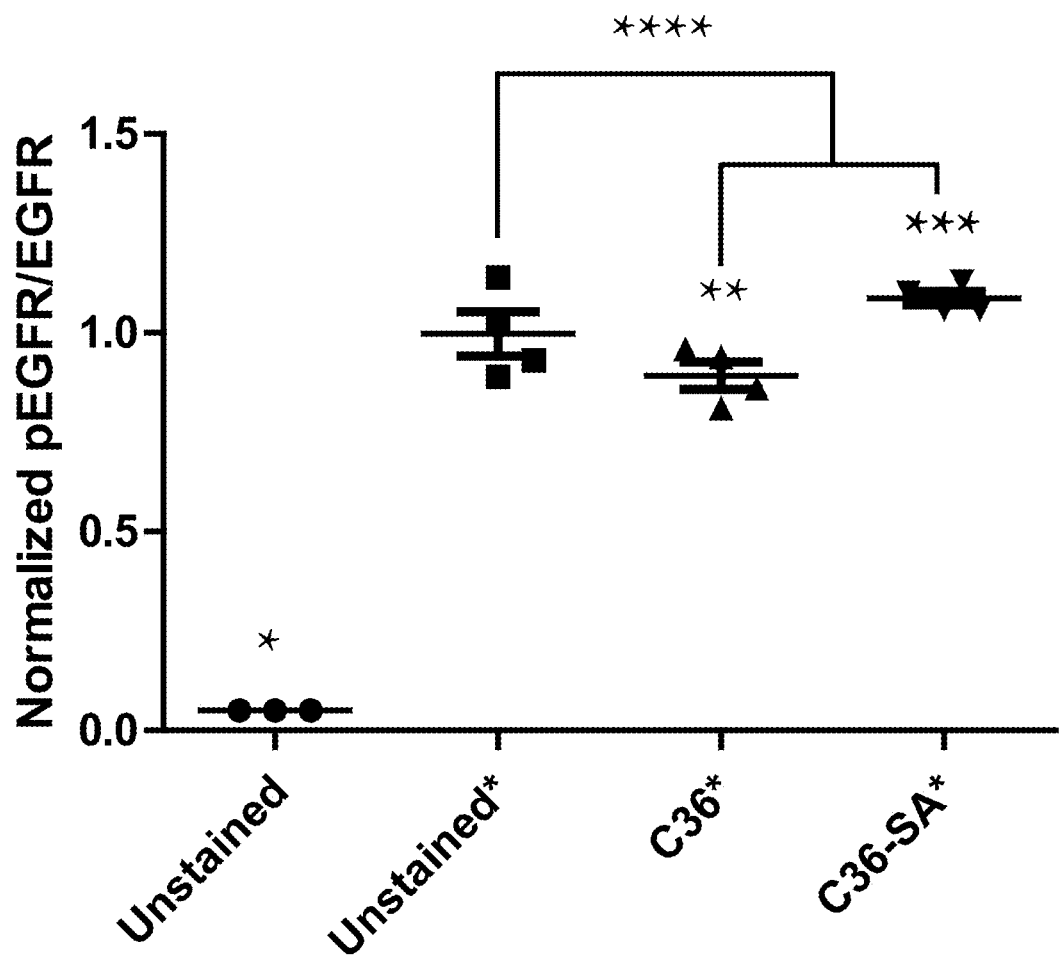
FIGS. 11B-11C show antidote treatment was necessary after sorting for restored EGF stimulability of E07-SA-stained but not E07-stained cells. Quantitative Western blots were also performed on A431 cells that had been sorted via FACS. Destaining, stimulation, lysing and Western blotting procedures to probe for phosphorylated EGFR (pEGFR; red) and total EGFR (green) were identical to those used for unsorted samples. * denotes stimulation with EGF; media DS=destained with media only; mA9 DS=destained with 5 µM mA9. Antibody and unstained cells were destained with media only. Destained C36 and SA-C36 (2:1 C36: SA conjugate mix) samples (FIG. 11B) did not inhibit stimulation of cells relative to the unstained positive control, but C36 and SA-C36 samples did stimulate cells to slightly different degrees ($p=0.012$ for  vs. *). Unlike unsorted samples, destaining sorted E07 samples (FIG. 11C) with media was sufficient to restore stimulation to native levels.
Figure 11B:
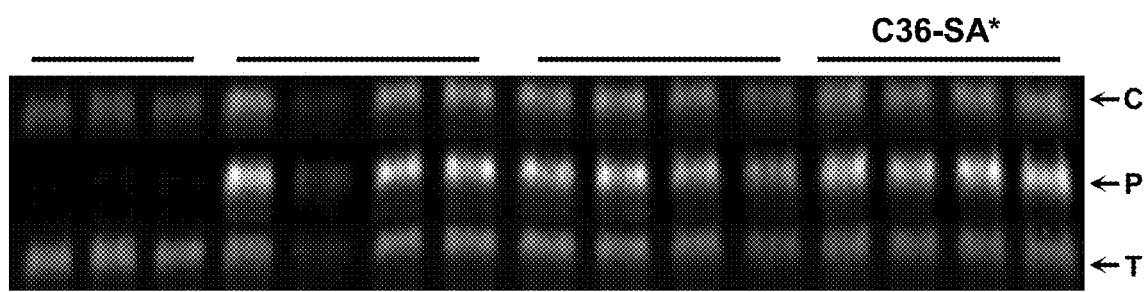
Figure 11C:
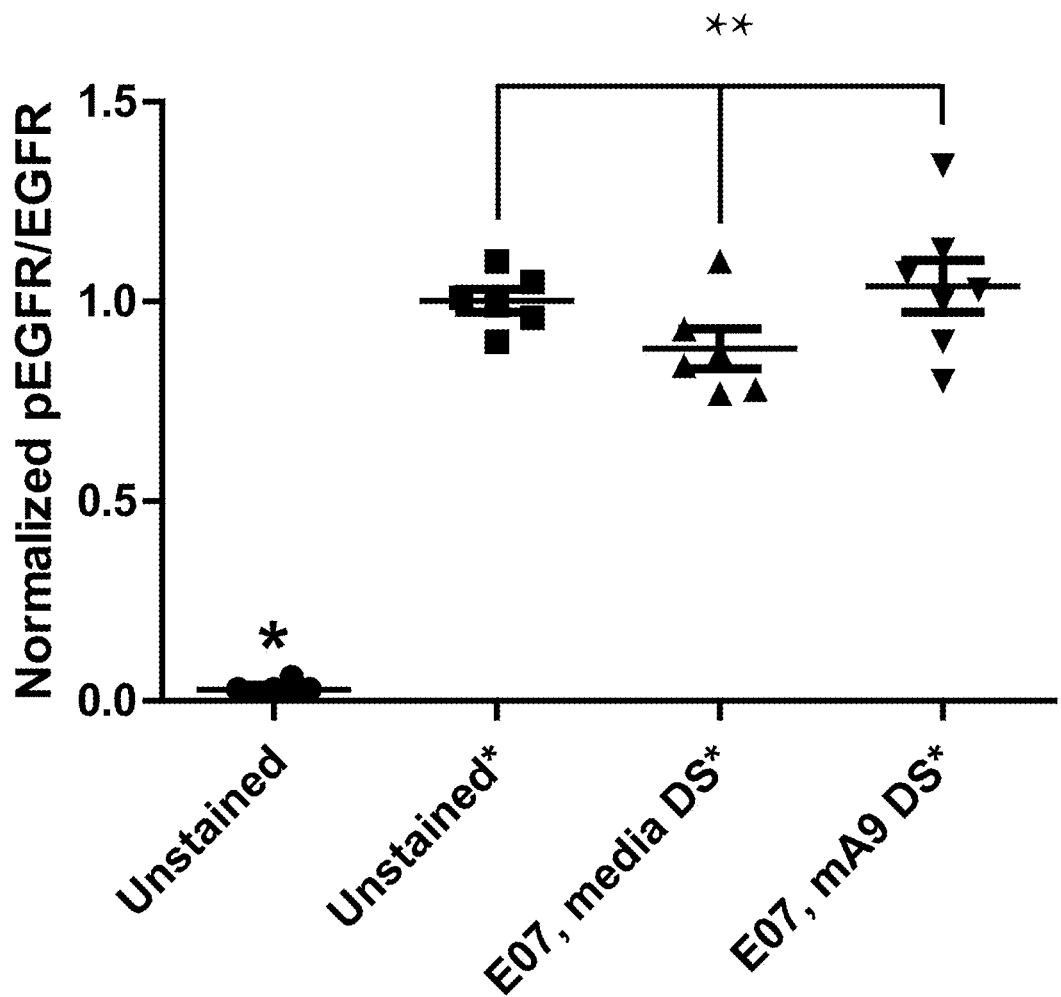
Figure 11C:
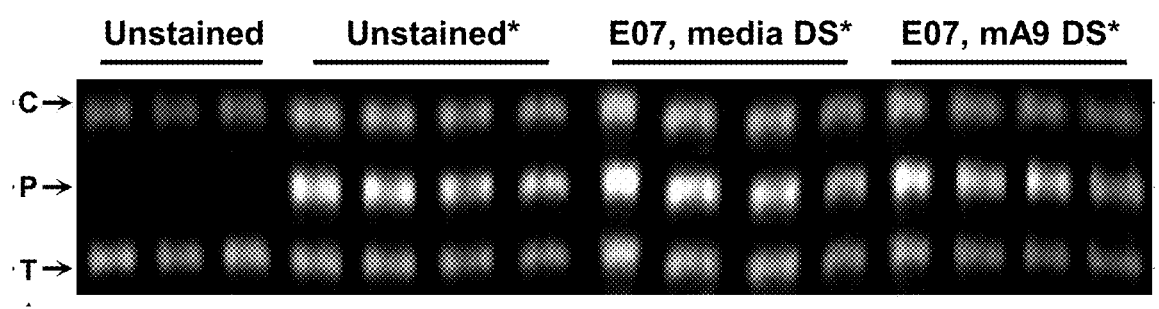

Recoverable stimulability was also demonstrated for sorted cells by conducting the same assay (FIGS. 4M and 11B-11C). Negative controls C36 and C36-SA conjugate mix were included to show that the presence of non-specific aptamer stain and streptavidin did not alter stimulation levels from unstained cells (FIG. 11B). After sorting, sufficient E07 was removed after destaining with media+ only to bring stimulation in line with unstained cells and mA9-destained cells (FIG. 11C). However, samples stained with the relatively stable E07-SA conjugate mix still required destaining with mA9 to rescue stimulation (FIG. 4M).

Quantitative Western blotting enabled quantification of EGF-induced stimulation of A431 cells via probing for phosphorylated (pEGFR; red) and total EGFR (green). * denotes stimulation with EGF; media DS=destained with media only; mA9 DS=destained with 5 µM mA9. Antibody and unstained cells were destained with media only. The degree of stimulation was taken as the ratio of the band intensities of pEGFR and total EGFR, as EGF binding triggers autophosphorylation of EGFR to generate pEGFR. Stained or unstained cells were destained for 5 min at 37° C. in media or 5 µM mA9, stimulated with 5 nM EGF for 15 min on ice and then lysed in the presence of phosphatase and protease inhibitors. Crude lysate samples containing equal amounts of protein were prepared, separated by denaturing polyacrylamide gel electrophoresis and blotted onto a membrane. The membrane was blocked with albumin and incubated overnight at 4° C. with primary antibodies for total EGFR and pEGFR. Secondary antibodies were used for detection and the blots were imaged. Band intensities corresponding to total EGFR and pEGFR were quantified by software and the pEGFR/total EGFR ratio for each sample was normalized to the average ratio for stimulated unstained cells, which served as the positive control for native, uninhibited stimulation. Destaining (FIG. 11A) E07 and (FIG. 4L) E07-SA (2:1 E07: SA conjugate mix) with media yielded significantly reduced stimulation compared with unstained cells. However, destaining with mA9 removed enough (FIG. 11A) E07 and (FIG. 4L) E07-SA to enable native stimulation levels in line with those of unstained cells. The neutralizing EGFR antibody D1D4J irreversibly suppressed stimulation to a greater degree than any other treatment (FIG. 4L). Each group is significantly different from all others ($p<0.0001$ for *, , * and ****).

Quantitative Western blots were also performed on A431 cells that had been sorted via FACS. Destaining, stimulation, lysing and Western blotting procedures to probe for phosphorylated EGFR (pEGFR; red) and total EGFR (green) were identical to those used for unsorted samples. * denotes stimulation with EGF; media DS=destained with media only; mA9 DS=destained with 5 µM mA9. Antibody and unstained cells were destained with media only. Destained C36 and SA-C36 (2:1 C36:SA conjugate mix) samples (FIG. 11B) did not inhibit stimulation of cells relative to the unstained positive control, but C36 and SA-C36 samples did stimulate cells to slightly different degrees ($p=0.012$ for  vs. *). Unlike unsorted samples, destaining sorted E07 samples (FIG. 11C) with media was sufficient to restore stimulation to native levels. In contrast, sorted E07-SA samples (2:1 E07:SA conjugate mix) (FIG. 4M) still required antidote to rescue cell stimulability.

Discussion

The Examples provided herein demonstrate that aptamers and matched antidotes can be used to reversibly stain and sort cells, returning the sorted cells to their native. This technology, therefore, opens up new applications for the positive selection of cells for clinical and therapeutic applications.

Antidotes specifically enhanced the rate of destaining, and 2' OMe RNA antidote was more potent than its DNA counterpart. Unpurified aptamer-streptavidin conjugate mixtures exhibited higher valency, avidity and stability than monomeric aptamer, but higher antidote concentrations still readily destained conjugates from cells. High cell viability was maintained across all experimental conditions despite cells being subjected to a variety of stresses and kept cold for long durations. Importantly, inhibited stimulation of the receptor targeted by the aptamer was abolished upon antidote-mediated destaining, restoring native behavior of cells sorted with a function-compromising stain. Antibodies targeting the same receptor also provided good stability for sorting, but their permanence irreversibly crippled the ability of isolated cells to be stimulated.

It was found early in the study that E07 staining was only stable at low temperatures. While this was actually an asset for its removal, it was critical to keep E07-stained samples cold until completion of sorting to preserve a strong fluorescent signal that clearly identified the cell population of interest. Losses at 37° C. of the minimized E07 aptamer used in this study were also found to be virtually the same as for its full-length parent sequence (data not shown), implying its instability was not imparted through truncation. Additionally, other studies have reported high off-rates of aptamers that reduce their utility for several applications including cell purification and targeted delivery for therapeutics.

Maintenance of E07-stained samples at 4° C. was also important for inhibiting endocytosis of bound aptamer, a process that readily occurs at physiological temperature. The complex of E07 and its target EGFR is readily internalized upon binding, which would prevent its removal during destaining. In addition to improving the stability of bound E07, low temperatures also hinder endocytosis due to substantially reduced fluidity of the cell membrane. Sustaining samples at 4° C. thus kept E07 stable on the extracellular surface to (1) provide robust signal during sorting and (2) maximize downstream aptamer removal.

In line with this rationale, antidote screening experiments to neutralize or remove bound E07 were initially performed at 4° C. The low cost of commercially produced DNA (versus modified RNA) was well suited for initial screening experiments, especially given the extremely high concentrations (100 µM) ultimately used. Even at that excessive concentration, 15-mer antidotes that together sampled the entirety of the E07 sequence failed to substantially block binding or destain already-bound aptamer at 4° C. Lower concentrations had an even more muted effect (data not shown). As avoiding aptamer internalization was not paramount for the purposes of antidote screening, blocking was then performed at 37° C. with better results. These data and those acquired during cold screenings together indicated that antidotes targeting the predicted loop structures of E07 were most effective, with antidote A9 having been one of the most effective and chosen as the lead antidote moving forward. This finding of loop-targeting antidotes being highly effective was consistent with successful antidotes developed in previous work.

It was then realized that the antidotes may not have been functional in the cold assays due to being structured. Fifteen-to-twenty base antidotes had successfully been used in the past to rapidly neutralize aptamers at physiological temperature, but at 4° C. these antidotes are predicted to be structured. In fact, a cursory survey of potential antidotes against E07 revealed that antidotes greater than 10 bases long on average had structure at that temperature (data not shown).

This finding prompted the attempt of an alternative strategy to destain cells at 4° C. Instead of using a single larger antidote that would be folded when cold, combinations of smaller antidotes were tested that together targeted larger regions but whose individual small sizes avoided structuring when cold. Groups of two or three antidotes seven or eight bases long were screened, as DNA this length was predicted to be capable of annealing to its target while not forming secondary structure (data not shown). In theory, this system should have been able to destain cells at 4° C. by avoiding the pitfalls that plagued larger antidotes. Only partial success was observed in practice, as short antidote combinations were capable of blocking E07 binding when cold, but they only performed about as well as the best performing longer antidotes at the real test of removing already bound aptamer from cells (data not shown).

In light of this and the established effectiveness of antidote A9 at physiological temperature, short-term 37° C. destaining treatment was employed in attempt to remove bound aptamer prior to endocytosis. While heat alone did remove E07 from cells (79% after 30 min), the presence of antidote (100 µM) greatly accelerated removal (97% after 10 min). This enhancement was found to be specific, as a still-excessively high concentration of control antidote possessing a randomly scrambled A9 sequence did not impact the rate or extent of destaining relative to media+ only. Endocytosis was also assessed and found to be very minor at approximately 4% after 10 min in media+ and 3% in sA9. The relatively rapid rate of E07 removal in the presence of A9 and mA9 competed favorably with the rate of internalization, further reducing endocytosis to about 1.5% (data not shown).

Lower concentrations of antidote A9 and its 2'OMe RNA analog mA9 were also tested in order to seek conditions that conserve reagent but still maximize the destaining rate. The minimum concentration of A9 that preserved its best observed destaining power was 5 and mA9 was similarly effective at this concentration. However, its higher potency enabled mA9 to preserve this maximal effectiveness at concentrations up to 10 fold lower. This greater potency has been routinely harnessed in development of antidotes for regulating aptamer therapeutics in vivo and is due to the higher binding affinity of 2'OMe to complementary bases (0.5-0.7° C. higher $T_m$ per nucleotide) compared to DNA. Using modified RNA antidotes with non-canonical bases (e.g. 2'F, 2'OMe) is a necessity motivated by the significantly higher stability in plasma that these bases confer. For in vitro applications like the one demonstrated here where nucleases are not a concern, DNA antidotes offer a financially compelling alternative even if significantly more is needed to achieve the desired effect.

Aptamer instability was also combated by utilizing multimeric E07-streptavidin conjugate mixtures in addition to keeping samples cold. Conjugates were generated by reacting biotinylated E07 and control C36 with AF488-labeled tetrameric streptavidin that theoretically supports decoration with four aptamers. To avoid steric effects that might impact aptamer binding upon conjugation, "tailed" aptamers (bE07 and bC36) with biotinylated 5' extensions were used. Additional cushion was provided by a six-carbon spacer between the biotin and the first nucleotide of the tail.

Reactions of biotinylated aptamer with SA yielded mixtures of unreacted aptamer and conjugates possessing a range of valencies, with a bE07:SA molar ratio of 3:1 appearing as a threshold for the production of substantially more multivalent conjugate. This is consistent with other studies working with aptamer-SA constructs that found the 3:1 to be optimal (Maier, Jangra et al. 2016). It is theorized that, despite biotin-SA being the strongest non-covalent bond known and an excess of available aptamer binding sites, maximum valencies of only two to three are possible due to (1) steric crowding and (2) electrostatic repulsion on SA as aptamer is added (Maier, Jangra et al. 2016). This theory explains the large amount of unincorporated aptamer in even the 1:1 mixture, the spectrum of conjugate species afforded and the requirement of excess aptamer to drive the yield of multivalent constructs.

The compositions of the unpurified conjugate mixtures explain the apparent binding affinity and saturation observed when used to stain cells. Since the amount of bE07 was increased relative to a constant amount of SA to prepare conjugate mixtures, more unreacted bE07 was present in higher ratio mixtures despite better incorporation observed by EMSA. The greater fraction of non-fluorescent unreacted bE07 at higher ratios better competed for binding and consequently reduced the amount of bound fluorescent conjugates, lowering the apparent saturation. Unlabeled competitor should not have impacted apparent binding affinity, so the greater apparent affinities of higher ratio conjugate mixtures accurately reflected their increased content of higher avidity constructs. While a greater difference in affinity of 3:1 versus 2:1 mixtures was expected given its higher average valency, there are diminishing returns on avidity for greater than bivalent conjugates. As unpurified conjugate mixture stains were compared to E07 in subsequent experiments, a ratio of 2:1 was selected for its similar apparent affinity but reduced competition with unlabeled, lower affinity competitor bE07 that would greatly impact EGF stimulation assays.

Despite its composition, significantly improved stability approaching that of monoclonal EGFR antibodies was achieved using unpurified conjugate reaction mixture relative to monomeric E07. Destaining experiments reflected this as a substantial reduction in aptamer lost over time at 37° C., and functional assays revealed much more robust neutralization of EGFR that prevented stimulation by agonist EGF. This improved average stability granted by the conjugate mixture was even more apparent after cell sorting. Considering this, the observed results are quite impressive.

Yet, the greater average stability in media+ bestowed by the conjugate mixtures was entirely defeatable at higher antidote concentrations (5 Interestingly, observation that reduced antidote concentrations were less effective at destaining conjugates implies they are crosslinking EGFRs on the cell surface. bE07 conjugated to SA but not associated with EGFR at the time of antidote treatment should be neutralized and consequently the local concentration of aptamer available for rebinding should be reduced. Thus, only multivalent conjugates simultaneously bound to more than one EGFR receptor prior to antidote treatment should provide additional stability over the monomer. Such multivalency-enabled crosslinking is routinely observed for antibodies, and the dimerization of EGFR is well characterized.

It was also promising that extremely high cell viability was maintained after sorting and destaining regardless of the treatment type. The procedure of detaching, staining, sorting, and destaining involves many stresses including multiple centrifugation steps and samples being kept cold for several hours. While A431 cells may be relatively robust and the viability data are only for necrosis and not apoptosis, the results are still very favorable and speak to the gentle nature of reversible aptamer-based cell staining.

We claim:

1. An aptamer conjugate comprising a multiplicity of aptamers each comprising a binding label, wherein the binding label of each of the multiplicity of aptamers is complexed to a linker, the linker comprising a reporter label and/or a magnetic label.

2. The aptamer conjugate of claim 1, wherein the binding label comprises biotin and the linker comprises streptavidin.

3. The aptamer conjugate of claim 1, wherein the reporter label comprises a fluorophore moiety.

4. The aptamer conjugate of claim 1, wherein the multiplicity of aptamers comprises two aptamers each comprising a binding label complexed to the same linker.

5. The aptamer conjugate of claim 1, wherein the aptamer is a multivalent aptamer comprising a multiplicity of binding motifs.

6. The aptamer conjugate of claim 5, wherein each of the multiplicity of binding motifs are the same.

7. The aptamer conjugate of claim 5, wherein each of the multiplicity of binding motifs are different.

8. The aptamer conjugate of claim 1, wherein the reporter label comprises one or more of a fluorophore moiety, an optical moiety, a radiolabel moiety, an X-ray moiety; an ultrasound imaging moiety, a photoacoustic imaging moiety, a nanoparticle-based moiety.

9. The aptamer conjugate of claim 1, wherein the aptamer is unbound from its molecular target.

* * * * *

SEQUENCE LISTING

```
Sequence total quantity: 27
SEQ ID NO: 1              moltype = RNA   length = 47
FEATURE                   Location/Qualifiers
misc_feature              1..47
                          note = Modifications: 5' AF488, 3' idT
source                    1..47
                          mol_type = other RNA
                          organism = synthetic construct
SEQUENCE: 1
ggacggattt aatcgccgta gaaagcatgt caaagccgga accgtcc                        47

SEQ ID NO: 2              moltype = RNA   length = 36
FEATURE                   Location/Qualifiers
misc_feature              1..36
                          note = Synthetic: C36
misc_feature              1..36
                          note = Modifications: 5' AF488, 3' idT
source                    1..36
                          mol_type = other RNA
                          organism = synthetic construct
SEQUENCE: 2
ggcgtagtga ttatgaatcg tgtgctaata cacgcc                                    36

SEQ ID NO: 3              moltype = DNA   length = 50
FEATURE                   Location/Qualifiers
misc_feature              1..50
                          note = Synthetic: bE07 forward primer
source                    1..50
                          mol_type = other DNA
                          organism = synthetic construct
SEQUENCE: 3
gataatacga ctcactatag ggatttagga cggatttaat cgccgtagaa                     50

SEQ ID NO: 4              moltype = DNA   length = 55
FEATURE                   Location/Qualifiers
misc_feature              1..55
                          note = Synthetic: bE07 reverse primer
source                    1..55
                          mol_type = other DNA
                          organism = synthetic construct
SEQUENCE: 4
ggacggttcc ggctttgaca tgctttctac ggcgattaaa tccgtcctaa atccc               55

SEQ ID NO: 5              moltype = RNA   length = 55
FEATURE                   Location/Qualifiers
misc_feature              1..55
                          note = Synthetic: bE07
misc_feature              1..55
                          note = 5' biotin
source                    1..55
                          mol_type = other RNA
                          organism = synthetic construct
SEQUENCE: 5
gggatttagg acggatttaa tcgccgtaga aagcatgtca aagccggaac cgtcc               55

SEQ ID NO: 6              moltype = DNA   length = 48
FEATURE                   Location/Qualifiers
misc_feature              1..48
                          note = Synthetic: bC36 forward primer
source                    1..48
                          mol_type = other DNA
                          organism = synthetic construct
SEQUENCE: 6
gataatacga ctcactatag gaaataggc gtagtgatta tgaatcgt                        48

SEQ ID NO: 7              moltype = DNA   length = 44
FEATURE                   Location/Qualifiers
misc_feature              1..44
                          note = Synthetic: bC36 forward primer
source                    1..44
                          mol_type = other DNA
                          organism = synthetic construct
SEQUENCE: 7
ggcgtgtatt agcacacgat tcataatcac tacgcctatt ttcc                           44

SEQ ID NO: 8              moltype = RNA   length = 44
FEATURE                   Location/Qualifiers
misc_feature              1..44
```

```
                              note = Synthetic: bC36
misc_feature                  1..44
                              note = 5' biotin
source                        1..44
                              mol_type = other RNA
                              organism = synthetic construct
SEQUENCE: 8
ggaaaatagg cgtagtgatt atgaatcgtg tgctaataca cgcc                          44

SEQ ID NO: 9                  moltype = DNA  length = 15
FEATURE                       Location/Qualifiers
misc_feature                  1..15
                              note = Synthetic: A1
source                        1..15
                              mol_type = other DNA
                              organism = synthetic construct
SEQUENCE: 9
tacggcgatt aaatc                                                          15

SEQ ID NO: 10                 moltype = DNA  length = 15
FEATURE                       Location/Qualifiers
misc_feature                  1..15
                              note = Synthetic: A2
source                        1..15
                              mol_type = other DNA
                              organism = synthetic construct
SEQUENCE: 10
tctacggcga ttaaa                                                          15

SEQ ID NO: 11                 moltype = DNA  length = 15
FEATURE                       Location/Qualifiers
misc_feature                  1..15
                              note = Synthetic: A3
source                        1..15
                              mol_type = other DNA
                              organism = synthetic construct
SEQUENCE: 11
tttctacggc gatta                                                          15

SEQ ID NO: 12                 moltype = DNA  length = 15
FEATURE                       Location/Qualifiers
misc_feature                  1..15
                              note = Synthetic: A4
source                        1..15
                              mol_type = other DNA
                              organism = synthetic construct
SEQUENCE: 12
gctttctacg gcgat                                                          15

SEQ ID NO: 13                 moltype = DNA  length = 15
FEATURE                       Location/Qualifiers
misc_feature                  1..15
                              note = Synthetic: A5
source                        1..15
                              mol_type = other DNA
                              organism = synthetic construct
SEQUENCE: 13
atgctttcta cggcg                                                          15

SEQ ID NO: 14                 moltype = DNA  length = 15
FEATURE                       Location/Qualifiers
misc_feature                  1..15
                              note = Synthetic: A6
source                        1..15
                              mol_type = other DNA
                              organism = synthetic construct
SEQUENCE: 14
acatgctttc tacgg                                                          15

SEQ ID NO: 15                 moltype = DNA  length = 15
FEATURE                       Location/Qualifiers
misc_feature                  1..15
                              note = Synthetic: A7
source                        1..15
                              mol_type = other DNA
                              organism = synthetic construct
SEQUENCE: 15
tgacatgctt tctac                                                          15
```

```
SEQ ID NO: 16            moltype = DNA   length = 15
FEATURE                  Location/Qualifiers
misc_feature             1..15
                         note = Synthetic: A8
source                   1..15
                         mol_type = other DNA
                         organism = synthetic construct
SEQUENCE: 16
tttgacatgc tttct                                                       15

SEQ ID NO: 17            moltype = DNA   length = 15
FEATURE                  Location/Qualifiers
misc_feature             1..15
                         note = Synthetic: A9
source                   1..15
                         mol_type = other DNA
                         organism = synthetic construct
SEQUENCE: 17
gctttgacat gcttt                                                       15

SEQ ID NO: 18            moltype = RNA   length = 15
FEATURE                  Location/Qualifiers
misc_feature             1..15
                         note = Synthetic: mA9
source                   1..15
                         mol_type = other RNA
                         organism = synthetic construct
SEQUENCE: 18
gctttgacat gcttt                                                       15

SEQ ID NO: 19            moltype = DNA   length = 15
FEATURE                  Location/Qualifiers
misc_feature             1..15
                         note = Synthetic: A10
source                   1..15
                         mol_type = other DNA
                         organism = synthetic construct
SEQUENCE: 19
cggctttgac atgct                                                       15

SEQ ID NO: 20            moltype = DNA   length = 15
FEATURE                  Location/Qualifiers
misc_feature             1..15
                         note = Synthetic: A11
source                   1..15
                         mol_type = other DNA
                         organism = synthetic construct
SEQUENCE: 20
tccggctttg acatg                                                       15

SEQ ID NO: 21            moltype = DNA   length = 15
FEATURE                  Location/Qualifiers
misc_feature             1..15
                         note = Synthetic: A12
source                   1..15
                         mol_type = other DNA
                         organism = synthetic construct
SEQUENCE: 21
gttccggctt tgaca                                                       15

SEQ ID NO: 22            moltype = DNA   length = 15
FEATURE                  Location/Qualifiers
misc_feature             1..15
                         note = Synthetic: A13
source                   1..15
                         mol_type = other DNA
                         organism = synthetic construct
SEQUENCE: 22
cggttccggc tttga                                                       15

SEQ ID NO: 23            moltype = DNA   length = 15
FEATURE                  Location/Qualifiers
misc_feature             1..15
                         note = Synthetic: A14
source                   1..15
                         mol_type = other DNA
                         organism = synthetic construct
SEQUENCE: 23
gcgattaaat ccgtc                                                       15
```

```
SEQ ID NO: 24              moltype = DNA   length = 15
FEATURE                    Location/Qualifiers
misc_feature               1..15
                           note = Synthetic: A15
source                     1..15
                           mol_type = other DNA
                           organism = synthetic construct
SEQUENCE: 24
cggcgattaa atccg                                                                15

SEQ ID NO: 25              moltype = DNA   length = 15
FEATURE                    Location/Qualifiers
misc_feature               1..15
                           note = Synthetic: A16
source                     1..15
                           mol_type = other DNA
                           organism = synthetic construct
SEQUENCE: 25
gacggttccg gcttt                                                                15

SEQ ID NO: 26              moltype = DNA   length = 15
FEATURE                    Location/Qualifiers
misc_feature               1..15
                           note = Synthetic: A17
source                     1..15
                           mol_type = other DNA
                           organism = synthetic construct
SEQUENCE: 26
aggacggttc cggct                                                                15

SEQ ID NO: 27              moltype = DNA   length = 15
FEATURE                    Location/Qualifiers
misc_feature               1..15
                           note = Synthetic: sA9
source                     1..15
                           mol_type = other DNA
                           organism = synthetic construct
SEQUENCE: 27
atctattgtg ttcgc                                                                15
```